United States Patent
Horvath et al.

(10) Patent No.: US 9,808,373 B2
(45) Date of Patent: Nov. 7, 2017

(54) INTRAOCULAR SHUNT IMPLANTATION

(71) Applicant: AqueSys, Inc., Aliso Viejo, CA (US)

(72) Inventors: Christopher Horvath, Mission Viejo, CA (US); Laszlo O. Romoda, San Clemente, CA (US); Richard A. Lewis, Sacramento, CA (US)

(73) Assignee: AqueSys, Inc., Aliso Viejo, CA (US)

( * ) Notice: Subject to any disclaimer, the term of this patent is extended or adjusted under 35 U.S.C. 154(b) by 372 days.

(21) Appl. No.: 14/317,676

(22) Filed: Jun. 27, 2014

(65) Prior Publication Data
US 2015/0005689 A1 Jan. 1, 2015

Related U.S. Application Data

(60) Provisional application No. 61/841,224, filed on Jun. 28, 2013, provisional application No. 61/895,341, filed on Oct. 24, 2013.

(51) Int. Cl.
A61F 9/00 (2006.01)
A61F 9/007 (2006.01)

(52) U.S. Cl.
CPC ................. *A61F 9/00781* (2013.01)

(58) Field of Classification Search
CPC .................................. A61F 9/00781
See application file for complete search history.

(56) References Cited

U.S. PATENT DOCUMENTS

| | | |
|---|---|---|
| 3,788,327 A | 1/1974 | Donowitz et al. |
| 3,960,150 A | 6/1976 | Hussain et al. |
| 4,090,530 A | 5/1978 | Lange |
| 4,402,308 A | 9/1983 | Scott |
| 4,562,463 A | 12/1985 | Lipton |
| 4,583,117 A | 4/1986 | Lipton et al. |
| 4,700,692 A | 10/1987 | Baumgartner |
| 4,722,724 A | 2/1988 | Schocket |
| 4,744,362 A | 5/1988 | Grundler |
| 4,750,901 A | 6/1988 | Molteno |
| 4,787,885 A | 11/1988 | Binder |
| 4,804,382 A | 2/1989 | Turina et al. |
| 4,820,626 A | 4/1989 | Williams et al. |
| 4,826,478 A | 5/1989 | Schocket |

(Continued)

FOREIGN PATENT DOCUMENTS

| | | |
|---|---|---|
| GB | 2 296 663 A | 7/1996 |
| WO | WO 94/13234 A1 | 6/1994 |

(Continued)

OTHER PUBLICATIONS

U.S. Appl. No. 14/541,070, filed Nov. 13, 2014, entitled "Intraocular Shunt Inserter".

(Continued)

*Primary Examiner* — Tatyana Zalukaeva
*Assistant Examiner* — Benjamin Klein
(74) *Attorney, Agent, or Firm* — Nathan S. Smith; McDermott Will & Emery LLP

(57) ABSTRACT

Implanting an intraocular shunt into an eye can involve creating an opening in the cornea and positioning a shunt in the anterior chamber of the eye such that the shunt terminates between layers of Tenon's capsule, thereby facilitating fluid flow out of the anterior chamber into a space between the layers of Tenon's capsule.

24 Claims, 64 Drawing Sheets

(56) References Cited

U.S. PATENT DOCUMENTS

| | | |
|---|---|---|
| 4,836,201 A | 6/1989 | Patton et al. |
| 4,848,340 A | 7/1989 | Bille et al. |
| 4,863,457 A | 9/1989 | Lee |
| 4,902,292 A | 2/1990 | Joseph |
| 4,911,161 A | 3/1990 | Schechter |
| 4,915,684 A | 4/1990 | MacKeen et al. |
| 4,934,363 A | 6/1990 | Smith et al. |
| 4,936,825 A | 6/1990 | Ungerleider |
| 4,946,436 A | 8/1990 | Smith |
| 4,968,296 A | 11/1990 | Ritch et al. |
| 4,978,352 A | 12/1990 | Fedorov et al. |
| 5,041,081 A | 8/1991 | Odrich |
| 5,057,098 A | 10/1991 | Zelman |
| 5,071,408 A | 12/1991 | Ahmed |
| 5,092,837 A | 3/1992 | Ritch et al. |
| 5,098,426 A | 3/1992 | Sklar et al. |
| 5,098,443 A | 3/1992 | Parel et al. |
| 5,162,641 A | 11/1992 | Fountain |
| 5,178,604 A | 1/1993 | Baerveldt et al. |
| 5,180,362 A | 1/1993 | Worst |
| 5,201,750 A | 4/1993 | Hocherl et al. |
| 5,207,660 A | 5/1993 | Lincoff |
| 5,275,622 A | 1/1994 | Lazarus et al. |
| 5,290,295 A | 3/1994 | Querals et al. |
| 5,300,020 A | 4/1994 | L'Esperance, Jr. |
| 5,333,619 A | 8/1994 | Burgio |
| 5,338,291 A | 8/1994 | Speckman et al. |
| 5,342,370 A | 8/1994 | Simon et al. |
| 5,360,339 A | 11/1994 | Rosenberg |
| 5,368,015 A | 11/1994 | Wilk |
| 5,370,607 A | 12/1994 | Memmen |
| 5,399,951 A | 3/1995 | Lavallee et al. |
| 5,410,638 A | 4/1995 | Colgate et al. |
| 5,443,505 A | 8/1995 | Wong et al. |
| 5,476,445 A | 12/1995 | Baerveldt et al. |
| 5,516,522 A | 5/1996 | Peyman et al. |
| 5,520,631 A | 5/1996 | Nordquist et al. |
| 5,558,629 A | 9/1996 | Baerveldt et al. |
| 5,558,630 A | 9/1996 | Fisher |
| 5,601,094 A | 2/1997 | Reiss |
| 5,656,026 A | 8/1997 | Joseph |
| 5,665,093 A | 9/1997 | Atkins et al. |
| 5,665,114 A | 9/1997 | Weadock et al. |
| 5,670,161 A | 9/1997 | Healy et al. |
| 5,688,562 A | 11/1997 | Hsiung |
| 5,695,474 A | 12/1997 | Daugherty |
| 5,704,907 A | 1/1998 | Nordquist et al. |
| 5,707,376 A | 1/1998 | Kavteladze et al. |
| 5,722,948 A | 3/1998 | Gross |
| 5,763,491 A | 6/1998 | Brandt et al. |
| 5,868,697 A | 2/1999 | Richter et al. |
| 5,908,449 A | 6/1999 | Bruchman et al. |
| 5,932,299 A | 8/1999 | Katoot |
| 5,938,583 A | 8/1999 | Grimm |
| 6,007,511 A | 12/1999 | Prywes |
| 6,007,578 A | 12/1999 | Schachar |
| 6,050,970 A | 4/2000 | Baerveldt |
| 6,086,543 A | 7/2000 | Anderson et al. |
| 6,102,045 A | 8/2000 | Nordquist et al. |
| 6,146,366 A | 11/2000 | Schachar |
| 6,165,210 A | 12/2000 | Lau et al. |
| 6,203,513 B1 | 3/2001 | Yaron et al. |
| 6,228,023 B1 | 5/2001 | Zaslavsky et al. |
| 6,228,873 B1 | 5/2001 | Brandt et al. |
| 6,261,256 B1 | 7/2001 | Ahmed |
| 6,264,665 B1 | 7/2001 | Yu et al. |
| 6,280,468 B1 | 8/2001 | Schachar |
| 6,413,540 B1 | 7/2002 | Yaacobi |
| 6,450,937 B1 | 9/2002 | Mercereau et al. |
| 6,471,666 B1 | 10/2002 | Odrich |
| 6,483,930 B1 | 11/2002 | Musgrave et al. |
| 6,524,275 B1 | 2/2003 | Lynch et al. |
| 6,533,768 B1 | 3/2003 | Hill |
| 6,544,249 B1 | 4/2003 | Yu et al. |
| 6,558,342 B1 | 5/2003 | Yaron et al. |
| 6,595,945 B2 | 7/2003 | Brown |
| 6,638,239 B1 | 10/2003 | Bergheim et al. |
| 6,699,210 B2 | 3/2004 | Williams et al. |
| 6,726,664 B2 | 4/2004 | Yaron et al. |
| D490,152 S | 5/2004 | Myall et al. |
| 6,736,791 B1 | 5/2004 | Tu et al. |
| 6,752,753 B1 | 6/2004 | Hoskins et al. |
| 6,881,198 B2 | 4/2005 | Brown |
| 6,936,053 B1 | 8/2005 | Weiss |
| 6,939,298 B2 | 9/2005 | Brown et al. |
| 7,008,396 B1 | 3/2006 | Straub |
| 7,037,335 B2 | 5/2006 | Freeman et al. |
| 7,041,077 B2 | 5/2006 | Shields |
| 7,094,225 B2 | 8/2006 | Tu et al. |
| 7,118,547 B2 | 10/2006 | Dahan |
| 7,135,009 B2 | 11/2006 | Tu et al. |
| 7,163,543 B2 | 1/2007 | Smedley et al. |
| 7,186,232 B1 | 3/2007 | Smedley et al. |
| 7,207,980 B2 | 4/2007 | Christian et al. |
| 7,291,125 B2 | 11/2007 | Coroneo |
| 7,331,984 B2 | 2/2008 | Tu et al. |
| 7,431,709 B2 | 10/2008 | Pinchuk et al. |
| 7,431,710 B2 | 10/2008 | Tu et al. |
| 7,458,953 B2 | 12/2008 | Peyman |
| 7,488,303 B1 | 2/2009 | Haffner et al. |
| 7,594,899 B2 | 9/2009 | Pinchuk et al. |
| 7,625,384 B2 | 12/2009 | Eriksson et al. |
| 7,708,711 B2 | 5/2010 | Tu et al. |
| 7,722,549 B2 | 5/2010 | Nakao |
| 7,837,644 B2 | 11/2010 | Pinchuk et al. |
| 7,867,186 B2 | 1/2011 | Haffner et al. |
| 8,109,896 B2 | 2/2012 | Nissan et al. |
| 8,267,882 B2 | 9/2012 | Euteneuer et al. |
| 8,277,437 B2 | 10/2012 | Saal et al. |
| 8,308,701 B2 | 11/2012 | Horvath et al. |
| 8,313,454 B2 | 11/2012 | Yaron et al. |
| 8,337,393 B2 | 12/2012 | Silverstrini et al. |
| 8,337,509 B2 | 12/2012 | Schieber et al. |
| 8,377,122 B2 | 2/2013 | Silvestrini et al. |
| 8,425,449 B2 | 4/2013 | Wardle et al. |
| 8,444,589 B2 | 5/2013 | Silvestrini |
| 8,486,000 B2 | 7/2013 | Coroneo |
| 8,506,515 B2 | 8/2013 | Burns et al. |
| 8,512,404 B2 | 8/2013 | Frion et al. |
| 8,529,492 B2 | 9/2013 | Clauson et al. |
| 8,535,333 B2 | 9/2013 | de Juan, Jr. et al. |
| 8,545,430 B2 | 10/2013 | Silvestrini |
| 8,585,629 B2 | 11/2013 | Grabner et al. |
| 8,663,303 B2 | 3/2014 | Horvath et al. |
| 8,721,702 B2 | 5/2014 | Romoda et al. |
| 8,758,290 B2 | 6/2014 | Horvath et al. |
| 8,765,210 B2 | 7/2014 | Romoda et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,974,511 B2 | 3/2015 | Horvath et al. |
| 9,017,276 B2 | 4/2015 | Horvath et al. |
| 9,095,411 B2 | 8/2015 | Horvath et al. |
| 9,095,413 B2 | 8/2015 | Romoda et al. |
| 9,192,516 B2 | 11/2015 | Horvath et al. |
| 9,271,869 B2 | 3/2016 | Horvath et al. |
| 9,283,116 B2 | 3/2016 | Romoda et al. |
| 9,326,891 B2 | 5/2016 | Horvath et al. |
| 9,393,153 B2 | 7/2016 | Horvath |
| 2001/0025150 A1 | 9/2001 | De Juan, Jr. et al. |
| 2001/0056254 A1 | 12/2001 | Cragg et al. |
| 2002/0099434 A1 | 7/2002 | Buscemi et al. |
| 2002/0133168 A1 | 9/2002 | Smedley et al. |
| 2003/0015203 A1 | 1/2003 | Makower et al. |
| 2003/0050574 A1 | 3/2003 | Krueger |
| 2003/0060752 A1 | 3/2003 | Bergheim et al. |
| 2003/0093084 A1 | 5/2003 | Nissan et al. |
| 2003/0097053 A1 | 5/2003 | Itoh |
| 2003/0187383 A1 | 10/2003 | Weber et al. |
| 2003/0236483 A1 | 12/2003 | Ren |
| 2003/0236484 A1 | 12/2003 | Lynch et al. |
| 2004/0077987 A1 | 4/2004 | Rapacki et al. |

(56) References Cited

U.S. PATENT DOCUMENTS

| | | |
|---|---|---|
| 2004/0147870 A1 | 7/2004 | Burns et al. |
| 2004/0210209 A1 | 10/2004 | Yeung et al. |
| 2004/0215133 A1 | 10/2004 | Weber et al. |
| 2004/0216749 A1 | 11/2004 | Tu |
| 2004/0236343 A1 | 11/2004 | Taylor et al. |
| 2004/0254521 A1 | 12/2004 | Simon |
| 2004/0260227 A1 | 12/2004 | Lisk, Jr. et al. |
| 2005/0049578 A1 | 3/2005 | Tu et al. |
| 2005/0101967 A1 | 5/2005 | Weber |
| 2005/0143363 A1 | 6/2005 | De Juan et al. |
| 2005/0246023 A1 | 11/2005 | Yeung |
| 2005/0267398 A1 | 12/2005 | Protopsaltis et al. |
| 2005/0271704 A1 | 12/2005 | Tu et al. |
| 2005/0277864 A1 | 12/2005 | Haffner et al. |
| 2006/0052721 A1 | 3/2006 | Dunker et al. |
| 2006/0064112 A1 | 3/2006 | Perez |
| 2006/0106370 A1 | 5/2006 | Baerveldt et al. |
| 2006/0116625 A1 | 6/2006 | Renati et al. |
| 2006/0149194 A1 | 7/2006 | Conston et al. |
| 2006/0155238 A1 | 7/2006 | Shields |
| 2006/0173397 A1 | 8/2006 | Tu et al. |
| 2006/0173446 A1 | 8/2006 | Dacquay et al. |
| 2006/0200113 A1 | 9/2006 | Haffner et al. |
| 2006/0241411 A1 | 10/2006 | Field et al. |
| 2007/0093783 A1 | 4/2007 | Kugler et al. |
| 2007/0118065 A1 | 5/2007 | Pinchuk et al. |
| 2007/0141116 A1 | 6/2007 | Pinchuk et al. |
| 2007/0172903 A1 | 7/2007 | Toner et al. |
| 2007/0191863 A1 | 8/2007 | de Juan, Jr. et al. |
| 2007/0263172 A1 | 11/2007 | Mura |
| 2007/0293872 A1 | 12/2007 | Peyman |
| 2008/0057106 A1 | 3/2008 | Erickson et al. |
| 2008/0108933 A1 | 5/2008 | Yu et al. |
| 2008/0147001 A1 | 6/2008 | Al-Marashi et al. |
| 2008/0181929 A1 | 7/2008 | Robinson et al. |
| 2008/0249467 A1 | 10/2008 | Burnett et al. |
| 2008/0281277 A1 | 11/2008 | Thyzel |
| 2008/0312661 A1 | 12/2008 | Downer et al. |
| 2009/0036818 A1 | 2/2009 | Grahn et al. |
| 2009/0043321 A1 | 2/2009 | Conston et al. |
| 2009/0124973 A1 | 5/2009 | D'Agostino et al. |
| 2009/0182421 A1 | 7/2009 | Silvestrini et al. |
| 2009/0209910 A1 | 8/2009 | Kugler et al. |
| 2009/0216106 A1 | 8/2009 | Takii |
| 2009/0264813 A1 | 10/2009 | Chang |
| 2009/0270890 A1 | 10/2009 | Robinson et al. |
| 2009/0281520 A1 | 11/2009 | Highley et al. |
| 2009/0287136 A1 | 11/2009 | Castillejos |
| 2010/0004581 A1 | 1/2010 | Brigatti et al. |
| 2010/0063478 A1 | 3/2010 | Selkee |
| 2010/0098772 A1 | 4/2010 | Robinson et al. |
| 2010/0100104 A1 | 4/2010 | Yu et al. |
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0134759 A1 | 6/2010 | Silvestrini et al. |
| 2010/0137981 A1 | 6/2010 | Silvestrini et al. |
| 2010/0173866 A1 | 7/2010 | Hee et al. |
| 2010/0191103 A1 | 7/2010 | Stamper et al. |
| 2010/0249691 A1* | 9/2010 | Van Der Mooren ............ A61F 9/00781 604/9 |
| 2010/0328606 A1 | 12/2010 | Peyman |
| 2011/0009874 A1 | 1/2011 | Wardle et al. |
| 2011/0046536 A1 | 2/2011 | Stegmann et al. |
| 2011/0098627 A1 | 4/2011 | Wilcox |
| 2011/0105990 A1 | 5/2011 | Silvestrini |
| 2011/0118745 A1 | 5/2011 | Yu et al. |
| 2011/0118835 A1 | 5/2011 | Silvestrini et al. |
| 2011/0230890 A1 | 9/2011 | Thyzel |
| 2011/0234976 A1 | 9/2011 | Kocaoglu et al. |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123430 A1 | 5/2012 | Horvath et al. |
| 2012/0123433 A1 | 5/2012 | Horvath et al. |
| 2012/0123434 A1 | 5/2012 | Grabner et al. |
| 2012/0123435 A1 | 5/2012 | Romoda et al. |
| 2012/0123436 A1 | 5/2012 | Reitsamer et al. |
| 2012/0123437 A1 | 5/2012 | Horvath et al. |
| 2012/0123438 A1* | 5/2012 | Horvath ............ A61F 9/00781 606/108 |
| 2012/0123439 A1 | 5/2012 | Romoda et al. |
| 2012/0123440 A1 | 5/2012 | Horvath et al. |
| 2012/0165720 A1 | 6/2012 | Horvath et al. |
| 2012/0165721 A1 | 6/2012 | Grabner et al. |
| 2012/0165722 A1 | 6/2012 | Horvath et al. |
| 2012/0165723 A1 | 6/2012 | Horvath et al. |
| 2012/0165933 A1 | 6/2012 | Haffner et al. |
| 2012/0197175 A1 | 8/2012 | Horvath et al. |
| 2012/0226150 A1 | 9/2012 | Balicki et al. |
| 2012/0310137 A1 | 12/2012 | Silvestrini |
| 2013/0149429 A1 | 6/2013 | Romoda et al. |
| 2013/0150770 A1 | 6/2013 | Horvath et al. |
| 2013/0158462 A1 | 6/2013 | Wardle et al. |
| 2013/0184631 A1 | 7/2013 | Pinchuk |
| 2013/0245573 A1 | 9/2013 | de Juan, Jr. et al. |
| 2013/0253406 A1 | 9/2013 | Horvath et al. |
| 2013/0253528 A1* | 9/2013 | Haffner ............... A61F 9/0017 606/107 |
| 2013/0281817 A1 | 10/2013 | Schaller et al. |
| 2013/0281908 A1 | 10/2013 | Schaller et al. |
| 2014/0018720 A1 | 1/2014 | Horvath et al. |
| 2014/0066833 A1 | 3/2014 | Yaron et al. |
| 2014/0081195 A1 | 3/2014 | Clauson et al. |
| 2014/0135916 A1 | 5/2014 | Clauson et al. |
| 2014/0180189 A1 | 6/2014 | Horvath et al. |
| 2014/0213958 A1 | 7/2014 | Clauson et al. |
| 2014/0236065 A1 | 8/2014 | Romoda et al. |
| 2014/0236066 A1 | 8/2014 | Horvath et al. |
| 2014/0236067 A1 | 8/2014 | Horvath et al. |
| 2014/0243730 A1 | 8/2014 | Horvath et al. |
| 2014/0272102 A1 | 9/2014 | Romoda et al. |
| 2014/0275923 A1 | 9/2014 | Haffner et al. |
| 2014/0276332 A1 | 9/2014 | Crimaldi et al. |
| 2014/0277349 A1 | 9/2014 | Vad |
| 2014/0287077 A1 | 9/2014 | Romoda et al. |
| 2014/0303544 A1 | 10/2014 | Haffner et al. |
| 2014/0323995 A1 | 10/2014 | Clauson et al. |
| 2014/0371651 A1 | 12/2014 | Pinchuk |
| 2015/0011926 A1 | 1/2015 | Reitsamer et al. |
| 2015/0038893 A1 | 2/2015 | Haffner et al. |
| 2015/0045714 A1 | 2/2015 | Horvath et al. |
| 2015/0057591 A1 | 2/2015 | Horvath et al. |
| 2015/0374545 A1 | 12/2015 | Horvath et al. |
| 2016/0135993 A1 | 5/2016 | Horvath et al. |
| 2016/0135994 A1 | 5/2016 | Romoda et al. |
| 2016/0158063 A1 | 6/2016 | Romoda et al. |

FOREIGN PATENT DOCUMENTS

| | | |
|---|---|---|
| WO | WO 94/21205 A1 | 9/1994 |
| WO | WO 95/08310 A1 | 3/1995 |
| WO | WO 98/23237 A1 | 6/1998 |
| WO | WO-00/56255 | 9/2000 |
| WO | WO-00/56255 A1 | 9/2000 |
| WO | WO 02/074052 A2 | 9/2002 |
| WO | WO 2007/087061 A2 | 8/2007 |
| WO | WO 2008/005873 A1 | 1/2008 |

OTHER PUBLICATIONS

U.S. Appl. No. 14/697,295, filed Apr. 27, 2015, entitled "Shunt Placement Through the Sclera".

* cited by examiner

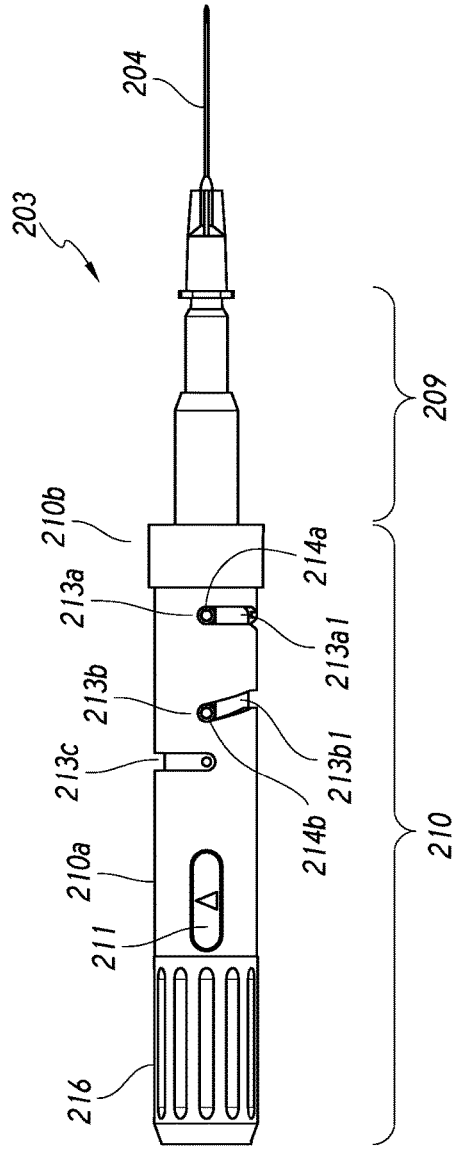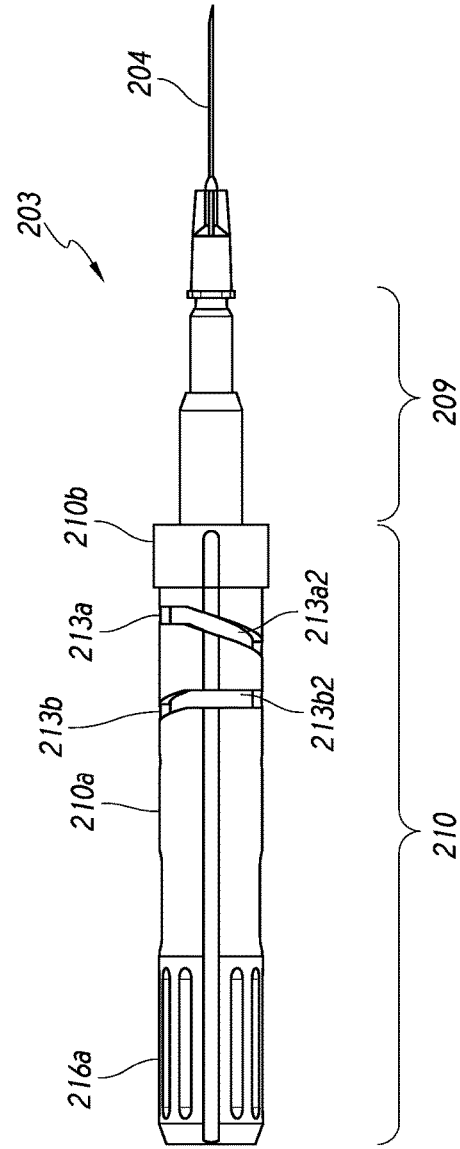

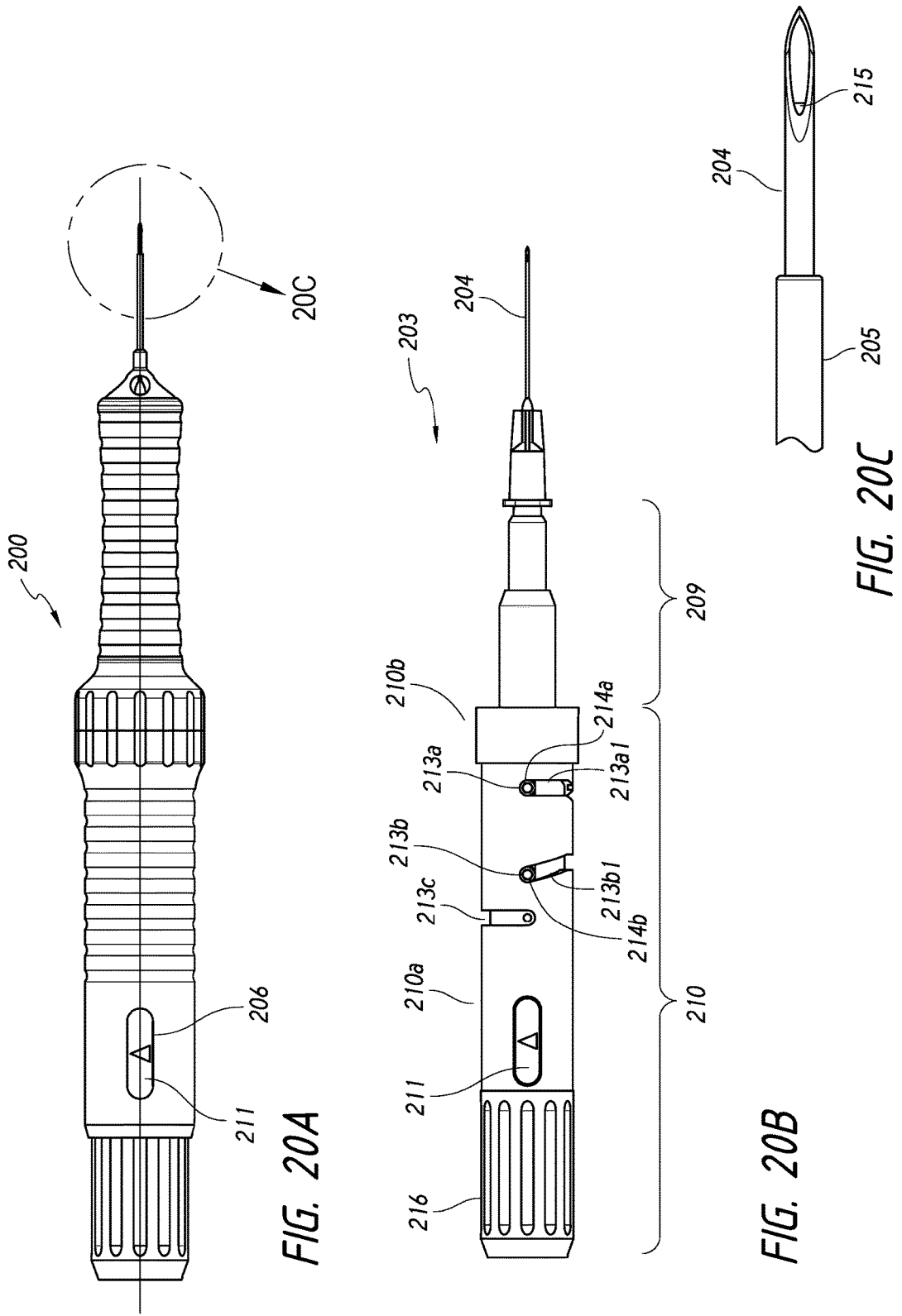

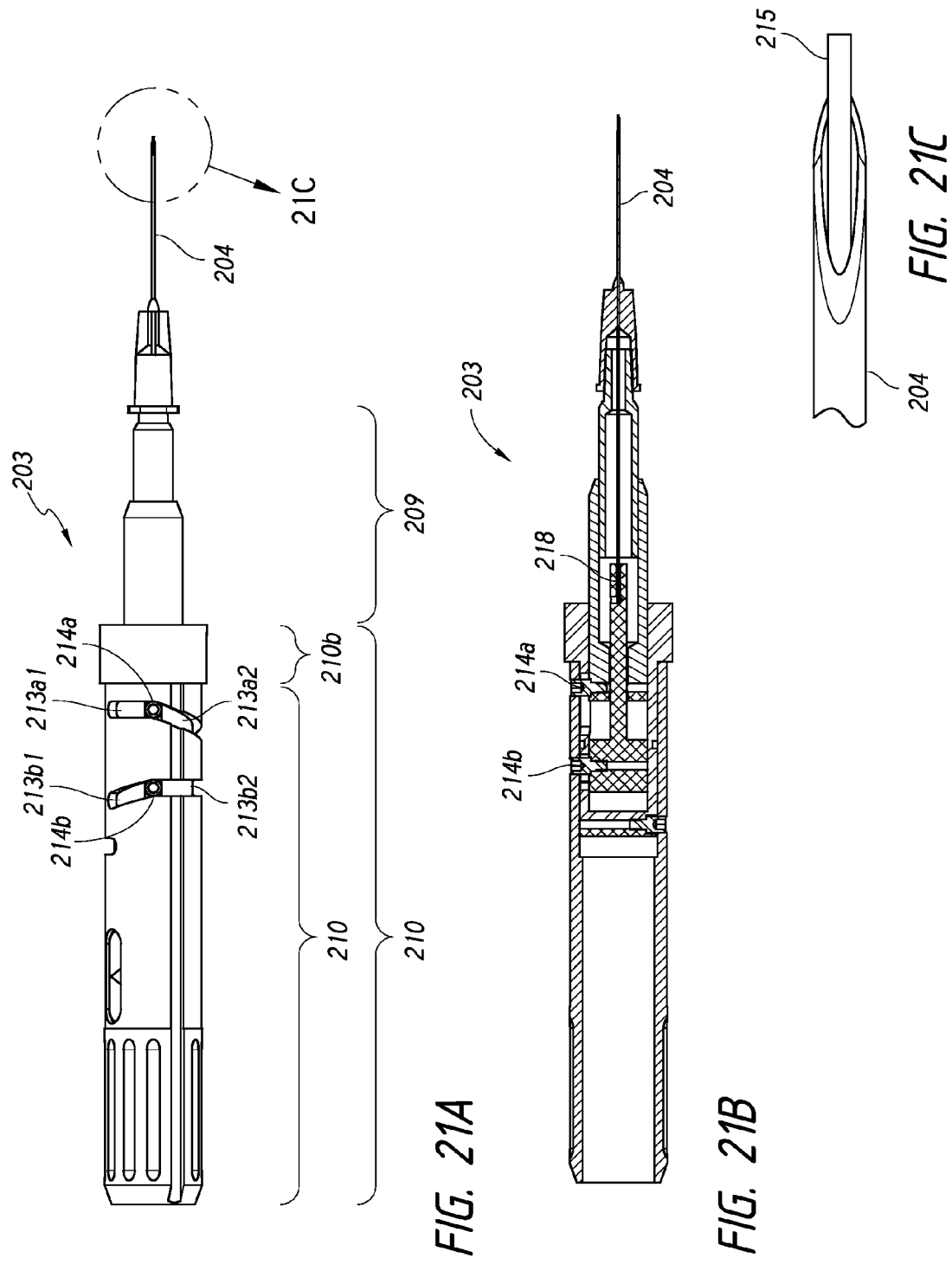

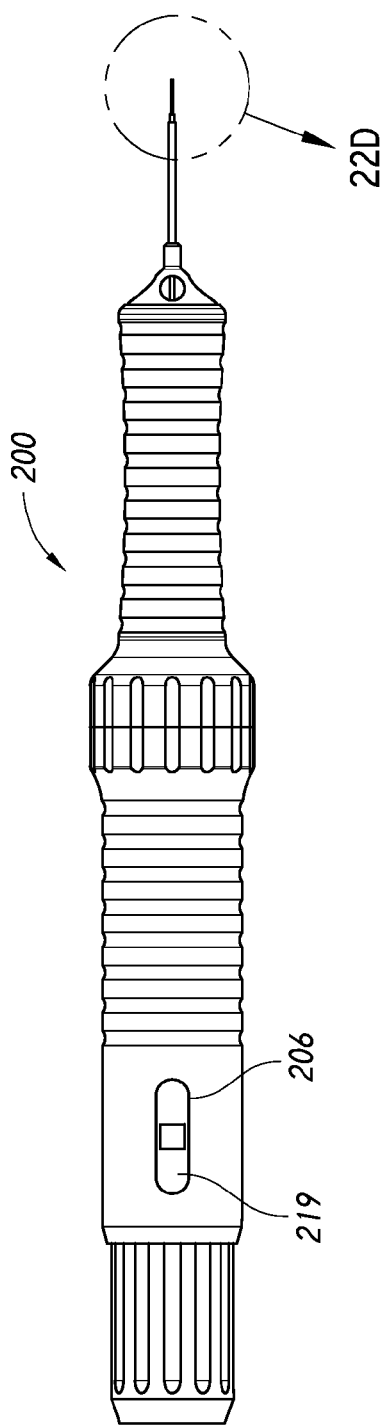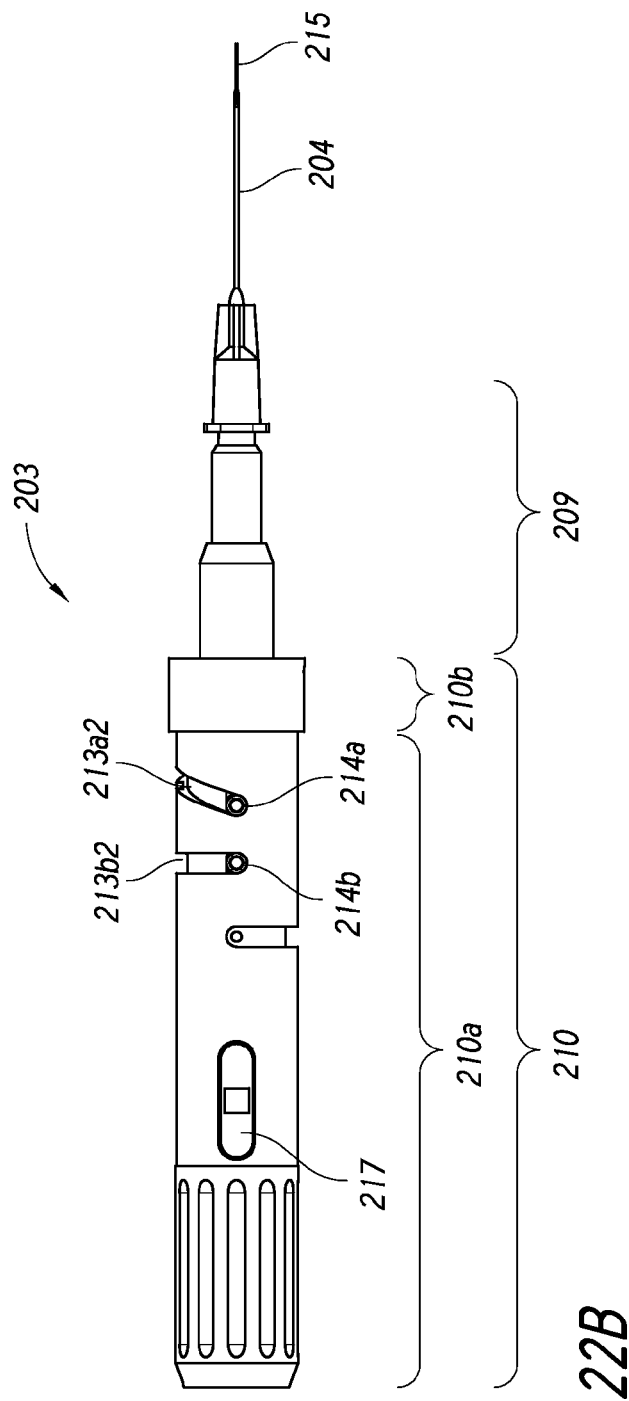
FIG. 22A
FIG. 22B

INTRAOCULAR SHUNT IMPLANTATION

CROSS-REFERENCE TO RELATED APPLICATIONS

This application claims the priority benefit of U.S. Provisional Application No. 61/841,224, filed on Jun. 28, 2013, and U.S. Provisional Application No. 61/895,341, filed on Oct. 24, 2013, the entirety of each of which is incorporated herein by reference.

BACKGROUND

Field of the Inventions

The present disclosure generally relates to devices and methods of implanting an intraocular shunt into an eye.

Description of the Related Art

Glaucoma is a disease in which the optic nerve is damaged, leading to progressive, irreversible loss of vision. It is typically associated with increased pressure of the fluid (i.e., aqueous humor) in the eye. Untreated glaucoma leads to permanent damage of the optic nerve and resultant visual field loss, which can progress to blindness. Once lost, this damaged visual field cannot be recovered. Glaucoma is the second leading cause of blindness in the world, affecting 1 in 200 people under the age of fifty, and 1 in 10 over the age of eighty for a total of approximately 70 million people worldwide.

The importance of lowering intraocular pressure (IOP) in delaying glaucomatous progression has been well documented. When drug therapy fails, or is not tolerated, surgical intervention is warranted. Surgical filtration methods for lowering intraocular pressure by creating a fluid flow-path between the anterior chamber and an area of lower pressure have been described. Intraocular shunts can be positioned in the eye to drain fluid from the anterior chamber to locations such as the sub-Tenon's space, the subconjunctival space, the episcleral vein, the suprachoroidal space, Schlemm's canal, and the intrascleral space.

Positioning of an intraocular shunt to drain fluid into the intrascleral space is promising because it avoids contact with the conjunctiva and the supra-choroidal space. Avoiding contact with the conjunctiva and supra-choroid is important because it reduces irritation, inflammation and tissue reaction that can lead to fibrosis and reduce the outflow potential of the subconjunctival and suprachoroidal space. The conjunctiva itself plays a critical role in glaucoma filtration surgery. A less irritated and healthy conjunctiva allows drainage channels to form and less opportunity for inflammation and scar tissue formation. intrascleral shunt placement safeguards the integrity of the conjunctiva and choroid, but may provide only limited outflow pathways that may affect the long term IOP lowering efficacy.

SUMMARY

According to some embodiments, methods and devices are provided for positioning an intraocular shunt within the eye to treat glaucoma. Various methods are disclosed herein which allow a clinician to create a fluid pathway from the anterior chamber to an area of lower pressure within the eye. Although methods may be discussed in the context of positioning an outflow end of a shunt in a particular location (e.g., between layers of Tenon's capsule), the methods disclosed herein can be used to create a fluid pathway in which the outflow end of the shunt is positioned in other areas of low pressure, such as the supraciliary space, supra-choroidal space, the intrascleral space (i.e., between layers of sclera), intra-Tenon's adhesion space (i.e., between layers of Tenon's capsule), or subconjunctival space.

For example, a method of treating glaucoma is disclosed that can comprise inserting an intraocular shunt into eye tissue such that an inflow end of the shunt is positioned in the anterior chamber of the eye and an outflow end of the shunt is positioned between layers of Tenon's capsule. The shunt can comprise a lumen that extends between the inflow and outflow ends and that is configured to permit flow of aqueous humor from the inflow end through the shunt to the outflow end.

In accordance with some embodiments, the shunt can be introduced into the eye through the cornea. After introducing the shunt through the cornea, the shunt can be advanced into the sclera. For example, the shunt can be advanced into the sclera through the anterior chamber angle tissue.

In some embodiments, the device comprises a shaft that can be advanced into the sclera until reaching and no further than a first position at which a bevel of the shaft is positioned between the layers of Tenon's capsule.

In some embodiments, after the shaft is positioned within the sclera (e.g., after the shaft reaches the first position), a pusher component of the device can be advanced relative to the shaft such that the shunt is pushed distally out of the shaft. Although the entire shunt can be advanced out of the shaft by the pusher component, the method can be implemented such that less than an entire length of the shunt is pushed distally out of the shaft.

The device can comprise a sleeve having a lumen and a distal end. The shaft can be received within the lumen of the sleeve.

In some embodiments, after the shaft is positioned within the sclera (e.g., after the shaft reaches the first position), the pusher component can be advanced to a distalmost position at which a distal end of the pusher component is positioned longitudinally proximal to the sleeve distal end. Further, the pusher component can also be advanced to a distalmost position at which a distal end of the pusher component is positioned longitudinally adjacent to the sleeve distal end.

Further, in some embodiments, the shaft can be positioned within the sclera (e.g., after the shaft reaches the first position) such that a distal end of the sleeve is spaced apart from the eye tissue. Once the shaft is in place, the pusher component can be advanced until a distal end of the pusher component is positioned longitudinally proximal to or adjacent to the sleeve distal end or the bevel. Furthermore, after the shunt has been at least partially advanced out of the bevel, the shaft can be proximally retracted into the sleeve. Proximal retraction of the shaft into the sleeve can be performed with the shaft maintaining its position relative to and within the sclera or with the sleeve maintaining its position relative to the sclera (whether spaced apart from the eye tissue or abutting the eye tissue), as discussed herein.

Moreover, as noted herein, some embodiments of the methods can be performed whether the outflow end of the shunt is positioned between layers of Tenon's capsule or whether the outflow end of the shunt is positioned in another area of low pressure.

For example, referring to embodiments in which the shunt outflow end is positioned between layers of Tenon's capsule, the device can be at the first position and a distal end of the sleeve can be spaced apart from the eye tissue, such as the anterior chamber angle tissue. Thereafter, while maintaining the position of the shaft relative to the sclera, the sleeve can be advanced distally over the shaft until the distal end of the sleeve contacts eye tissue, such as the anterior chamber angle tissue. After the sleeve distal end contacts the tissue, the shaft can be proximally withdrawn from the sclera until the bevel is received within a lumen of the sleeve. However, in some embodiments, the sleeve distal end can be maintained at a given position relative to the eye tissue (whether the sleeve distal end is spaced apart from or abutting the eye tissue) while the shaft is withdrawn into the sleeve.

In some embodiments, a method of treating glaucoma is provided that can comprise inserting an intraocular shunt into eye tissue such that the shunt conducts fluid from the anterior chamber of the eye to a region between layers of Tenon's capsule. Further, in some embodiments, the method can comprise inserting an intraocular shunt into eye tissue such that the shunt conducts fluid from the anterior chamber of the eye to the intra-Tenon's adhesion space of the eye.

The method can also be performed such that a hollow shaft is inserted into the eye through the cornea. The shaft can be configured to hold the shunt. For example, the shaft can be enter the eye through the cornea. The intra-Tenon's adhesion space can comprise a deep layer and a superficial layer, and an outflow end of the shunt can be positioned between the deep and superficial layers.

Further, a bevel of a shaft can be advanced to a position between the deep and superficial layers, and while maintaining the bevel stationary relative to the eye tissue, the shunt can be distally advanced from the shaft into the intra-Tenon's adhesion space.

In accordance with some embodiments, a method of treating glaucoma is disclosed that can comprise advancing a shaft of a device into eye tissue until a bevel of the shaft reaches a target area. Then, while maintaining the bevel substantially stationary relative to the target area, the sleeve of the device can be advanced distally over the shaft until a distal end of the sleeve contacts the eye tissue. Thereafter, upon contacting the sleeve distal end with the eye tissue, the shaft can be proximally withdrawn from the eye tissue.

Additionally, while maintaining the bevel substantially stationary relative to the target area, a plunger can be advanced within the shaft to advance a shunt until the shunt extends into the target area. For example, less than an entire length of the shunt can be pushed distally out of the shaft. The plunger can be advanced until a distal end of the plunger is positioned longitudinally adjacent to the sleeve distal end. The shunt can be introduced into the eye through the cornea. The target area can be selected from supraciliary space, suprachoroidal space, a space between layers of sclera (i.e., intrascleral space), a space between layers of Tenon's capsule (i.e., intra-Tenon's adhesion space), or subconjunctival space. The sleeve can be advanced between about 1 mm to about 4 mm. Further, in some embodiments, the sleeve can be advanced between about 2 mm to about 3 mm.

For example, in some embodiments, a method of deploying an intraocular shunt into an eye is provided. The method can comprise the steps of: inserting into the eye a hollow shaft configured to hold the intraocular shunt; and advancing the shunt from the hollow shaft such that the shunt forms a passage from the anterior chamber of the eye to the intra-Tenon's adhesion space of the eye.

The inserting step can further comprise the step of injecting an aqueous solution into the eye. For example, the aqueous solution can be injected below Tenon's capsule. The inserting step can also comprise ab interno insertion of the hollow shaft into the eye. Ab interno insertion can comprise inserting the hollow shaft into the eye above the corneal limbus. Further, ab interno insertion can comprise inserting the hollow shaft into the eye below the corneal limbus.

Additionally, some methods can comprise: inserting into the eye a hollow shaft configured to hold the intraocular shunt, a portion of the hollow shaft extending linearly along a longitudinal axis, and at least one other portion of the hollow shaft extending off the longitudinal axis; and advancing the shunt from the hollow shaft such that the shunt forms a passage from the anterior chamber of the eye to the intra-Tenon's adhesion space.

In accordance with some embodiments, a method of treating glaucoma can also comprise inserting an intraocular shunt into eye tissue such that an inflow end of the shunt is positioned in the anterior chamber of the eye and an outflow end of the shunt is positioned between layers of Tenon's capsule. The layers of Tenon's capsule can comprise a deep layer and a superficial layer.

Some embodiments of the methods disclosed herein such that the inserting step can further comprise the step of injecting an aqueous solution into the eye. For example, an aqueous solution can be injected below Tenon's capsule. The inserting step can also comprise ab interno insertion of the hollow shaft into the eye. Ab interno insertion can comprise inserting the hollow shaft into the eye above the corneal limbus. Ab interno insertion can comprise inserting the hollow shaft into the eye below the corneal limbus.

Some embodiments of the methods disclosed herein can be implemented such that the inserting step comprises ab interno insertion of the hollow shaft into the eye.

Some embodiments of the methods disclosed herein can be implemented such that the hollow shaft is inserted into the eye without removing an anatomical feature of the eye.

The anatomical feature of the eye can be selected from the group consisting of: the trabecular meshwork, the iris, the cornea, and the aqueous humor. In accordance with some embodiments, the method can be performed without inducing subconjunctival blebbing or endophthalmitis.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments are described below with reference to the drawings. The illustrated embodiments are intended to illustrate, but not to limit, the inventions. The drawings contain the following figures:

FIGS. 17A-17D are schematics showing different enlarged views of the deployment mechanism of the deployment device, according to some embodiments.

FIGS. 20A-20B show schematics of the deployment mechanism in a pre-deployment configuration, according to some embodiments.

FIG. 20C shows an enlarged view of the distal portion of the deployment device of FIG. 20A, with an intraocular shunt loaded within a hollow shaft of the deployment device, according to some embodiments.

FIGS. 21A-21B show schematics of the deployment mechanism at the end of the first stage of deployment of the shunt from the deployment device, according to some embodiments.

FIG. 21C shows an enlarged view of the distal portion of the deployment device of FIG. 21A, with an intraocular shunt partially deployed from within a hollow shaft of the deployment device, according to some embodiments.

FIG. 22A shows a schematic of the deployment device after deployment of the shunt from the device, according to some embodiments.

FIG. 22B show a schematic of the deployment mechanism at the end of the second stage of deployment of the shunt from the deployment device, according to some embodiments.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Additionally, it is contemplated that although some embodiments may be disclosed or shown in the context of ab interno procedures, such embodiments can be used in ab externo procedures. Furthermore, various applications of such embodiments and modifications thereto, which may occur to those who are skilled in the art, are also encompassed by the general concepts described herein.

Glaucoma is a disease in which the optic nerve is damaged, leading to progressive, irreversible loss of vision. It is typically associated with increased pressure of the fluid (i.e., aqueous humor) in the eye. Untreated glaucoma leads to permanent damage of the optic nerve and resultant visual field loss, which can progress to blindness. Once lost, this damaged visual field cannot be recovered.

In conditions of glaucoma, the pressure of the aqueous humor in the eye (anterior chamber) increases and this resultant increase of pressure can cause damage to the vascular system at the back of the eye and especially to the optic nerve. The treatment of glaucoma and other diseases that lead to elevated pressure in the anterior chamber involves relieving pressure within the anterior chamber to a normal level.

Glaucoma filtration surgery is a surgical procedure typically used to treat glaucoma. The procedure involves placing a shunt in the eye to relieve intraocular pressure by creating a pathway for draining aqueous humor from the anterior chamber of the eye. The shunt is typically positioned in the eye such that it creates a drainage pathway between the anterior chamber of the eye and a region of lower pressure. Various structures and/or regions of the eye having lower pressure that have been targeted for aqueous humor drainage include Schlemm's canal, the subconjunctival space, the episcleral vein, the suprachoroidal space, or the subarachnoid space. Methods of implanting intraocular shunts are known in the art. Shunts may be implanted using an ab externo approach (entering through the conjunctiva and inwards through the sclera) or an ab interno approach (entering through the cornea, across the anterior chamber, through the trabecular meshwork and sclera).

Figure 1:
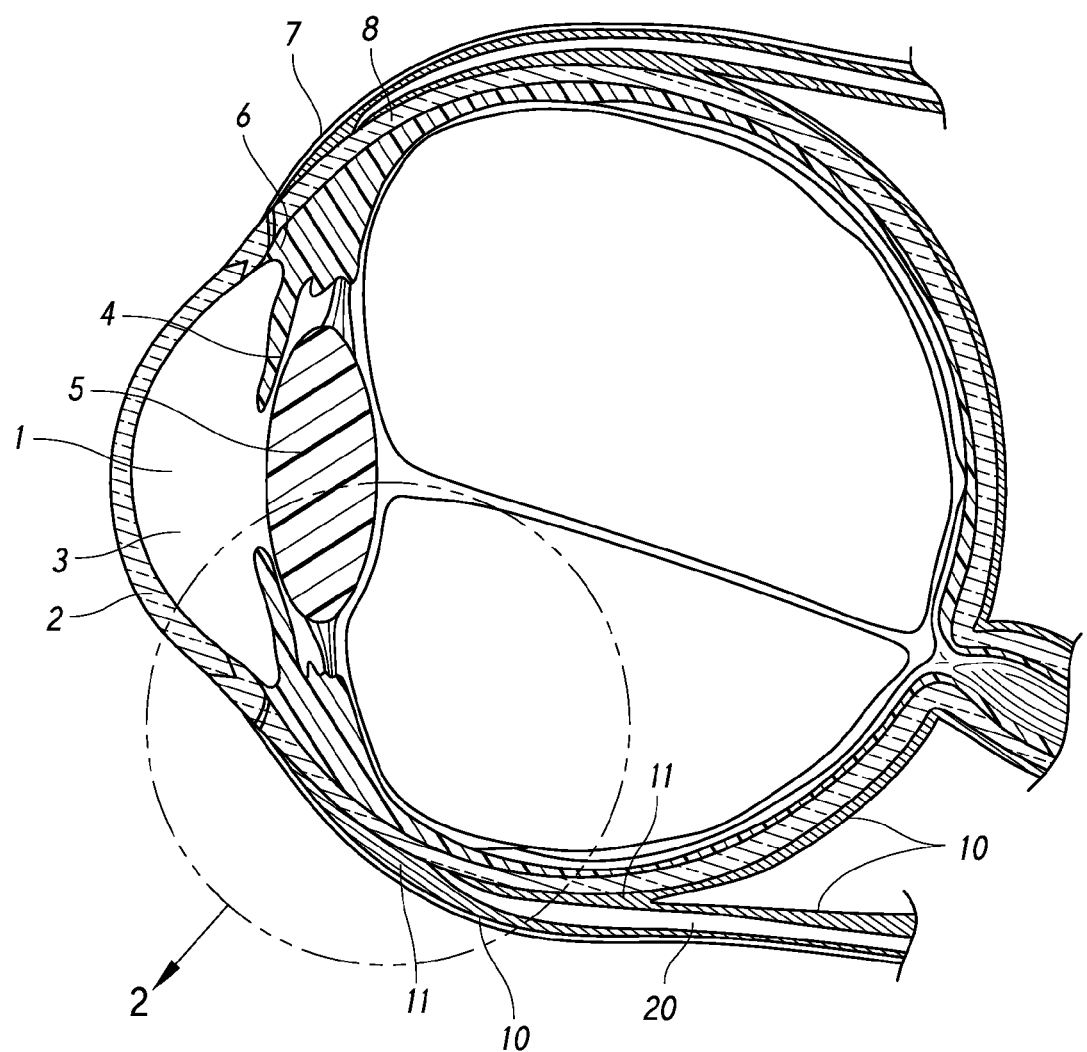
FIG. 1 provides a cross-sectional diagram of the general anatomy of the eye.

FIG. 1 provides a schematic diagram of the general anatomy of the eye. An anterior aspect of the anterior chamber 1 of the eye is the cornea 2, and a posterior aspect of the anterior chamber 1 of the eye is the iris 4. Beneath the iris 4 is the lens 5. The anterior chamber 1 is filled with aqueous humor 3. The aqueous humor 3 drains into a space(s) 6 deep to the conjunctiva 7 through the trabecular meshwork (not shown in detail) of the sclera 8. The aqueous humor is drained from the space(s) 6 deep to the conjunctiva 7 through a venous drainage system (not shown).

Figure 2:
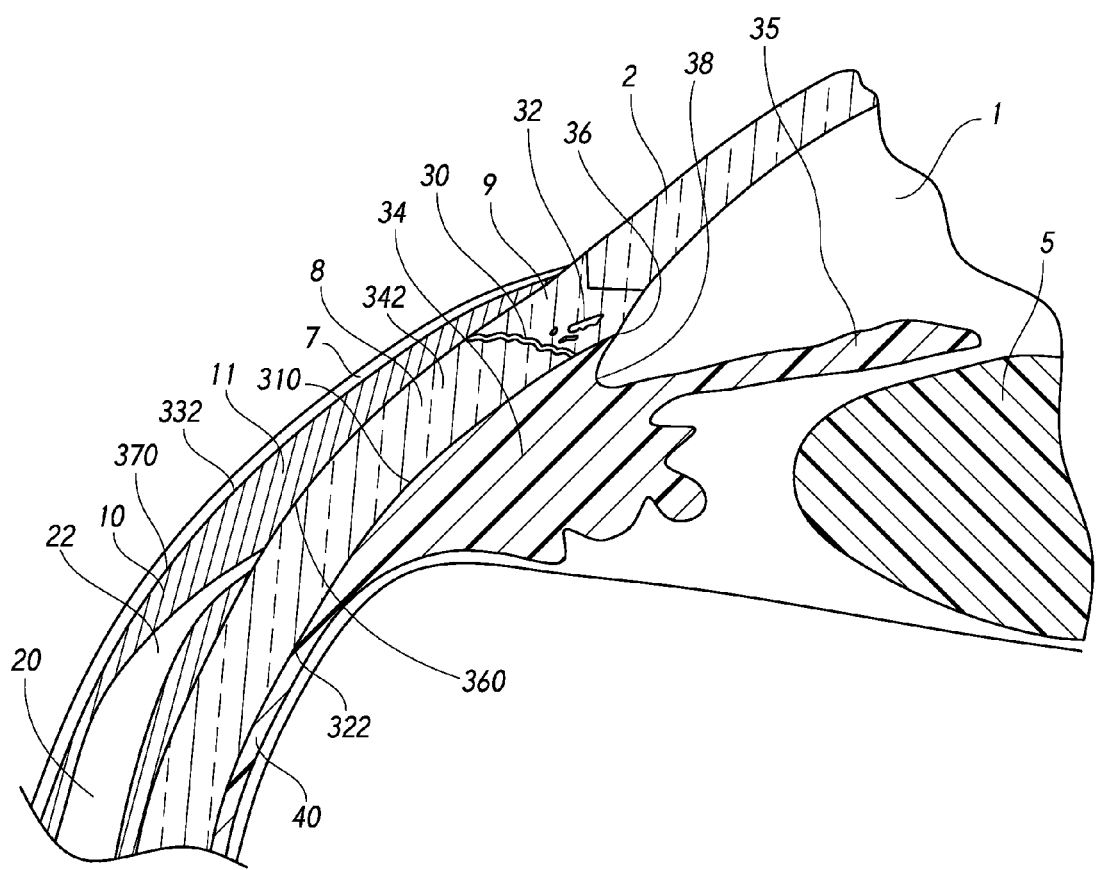
FIG. 2 is an enlarged cross-sectional diagram of the eye taken along section lines 2-2 of FIG. 1.

FIG. 2 is an enlarged view of the schematic diagram of FIG. 1 taken along section lines 2-2. FIG. 2 illustrates a detail view of the sclera 8 and surrounding tissue. As shown, the conjunctiva 7 attaches to the sclera 8 at the limbus 9.

Deep to the conjunctiva 7 is Tenon's capsule 10, sometimes referred to as Tenon's membrane or Tenon's tendon. Tenon's capsule 10 comprises two layers (i.e., superficial and deep layers) and an intra-Tenon's adhesion space 10 that extends between the superficial and deep layers of Tenon's capsule 10. The intra-Tenon's adhesion space 11 surrounds the eye circumferentially. The intra-Tenon's adhesion space 11 can extend around the eye posterior to the limbus 9.

In the view of FIG. 2, deep to the intra-Tenon's adhesion space 11 is a rectus muscle 20. The eye has four rectus muscles (superior, inferior, lateral, and medial) that attach to sclera via a rectus tendon. FIG. 2 illustrates that the rectus muscle 20 attaches to the sclera 8 via a rectus tendon 22. For illustration purposes, the rectus tendon 22 is shown inserting onto the sclera 8. In some cases, there may not be a clear insertion point of the rectus tendon 22 onto the sclera 8, but there will be a gradual transition between the rectus tendon 22 and the intra-Tenon's adhesion space 11.

Additionally, as illustrated in FIG. 1, Tenon's capsule 10 and the intra-Tenon's adhesion space 11 is illustrated extending anteriorly relative to and superficial to the rectus muscle 20. As also shown, posterior to the rectus tendon, Tenon's capsule 10 and the intra-Tenon's adhesion space 11 also extend deep to and around the rectus muscle 20. In this region, there is a reflection of Tenon's capsule 10 and the intra-Tenon's adhesion space 11 from the rectus muscle 20 onto the globe or sclera 8. Thus, Tenon's capsule 10 and the intra-Tenon's adhesion space 11 envelop or encapsulate the rectus muscle 20.

FIG. 2 illustrates that in some locations, Tenon's capsule 10, and thus, the intra-Tenon's adhesion space 11, surrounds a rectus muscle 20. According to some embodiments of the methods disclosed herein, the intra-Tenon's adhesion space 11 can be accessed from the anterior chamber 1. Tenon's capsule 10 and the intra-Tenon's adhesion space 11 surround the eye circumferentially.

FIG. 2 also illustrates the drainage channels of the eye, including Schlemm's canal 30 and the trabecular meshwork 32, which extend through the sclera 8. Further, deep to the sclera 8, the ciliary body 34 is also shown. The ciliary body 34 transitions posteriorly to the choroid 40. Deep to the limbus 9 is a scleral spur 36. The scleral spur 36 extends circumferentially within the anterior chamber 1 of the eye. Further, the scleral spur 36 is disposed anteriorly to the anterior chamber angle 38. Furthermore, "anterior chamber angle tissue" can refer to the eye tissue in the region extending along and/or including one or more of the cornea 2, the sclera 8, Schlemm's canal 30, the trabecular meshwork 32, the ciliary body 34, the iris 35, or the scleral spur 36.

Accordingly, for definitional purposes, the space between the conjunctiva 7 and Tenon's capsule or the intra-Tenon's adhesion space 11 is referred to herein as subconjunctival space 332 (here shown as a potential space). Further, the space within a deep layer 360 and a superficial layer 370 of Tenon's capsule 10 is referred to herein as the intra-Tenon's adhesion space 11. Additionally, the space within the sclera 8 (i.e., between the superficial and deep layers of the sclera 8) is referred to herein as intrascleral space 342 (here shown as a potential space). The space between the sclera 8 and the ciliary body 34 is referred to herein as supraciliary space 310 (here shown as a potential space). Finally, the space between the sclera 8 and the choroid 40 is referred to as suprachoroidal space 322 (here shown as a potential space). The supraciliary space 310 can be continuous with the suprachoroidal space 322.

Figure 3:
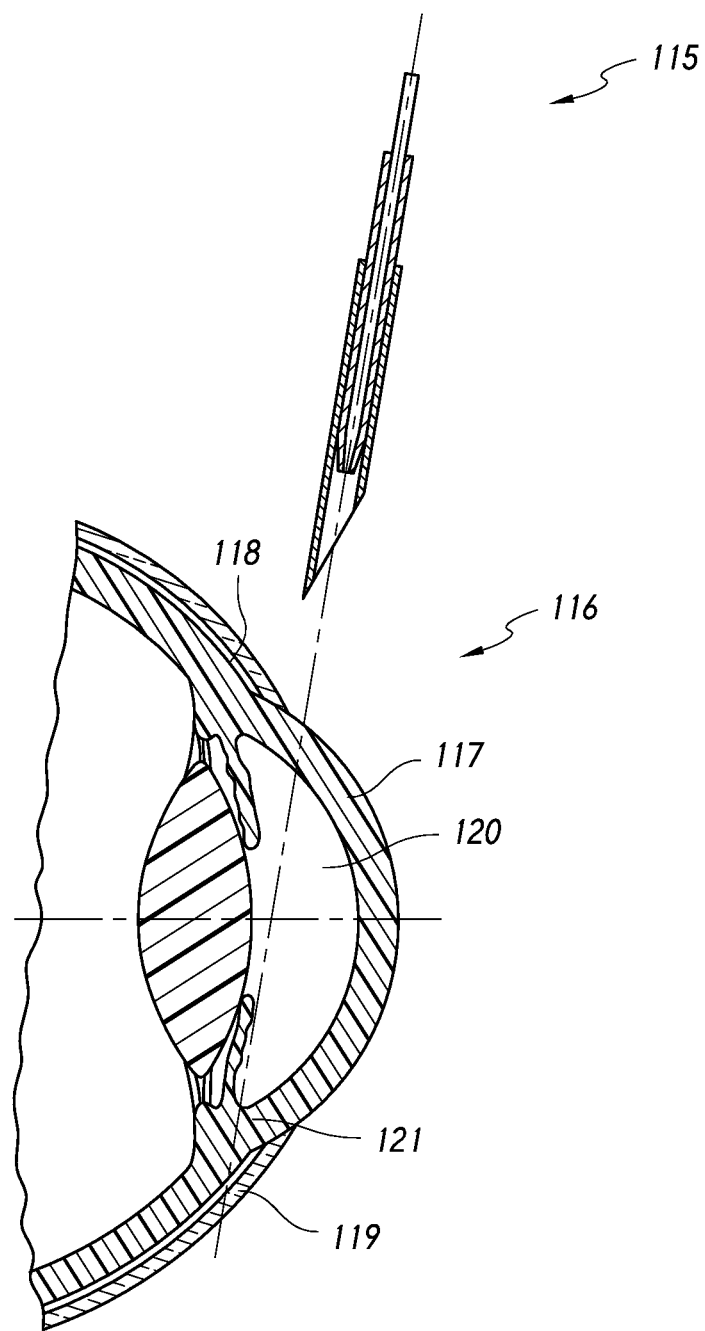
FIG. 3 depicts, implantation of an intraocular shunt with a distal end of a deployment device holding a shunt, shown in cross-section, according to some embodiments.

Ab interno approaches for implanting an intraocular shunt in the subconjunctival space are shown for example in Yu et al. (U.S. Pat. No. 6,544,249 and U.S. Patent Publication No. 2008/0108933) and Prywes (U.S. Pat. No. 6,007,511), the contents of each of which are incorporated by reference herein in its entirety. Briefly and with reference to FIG. 3, a surgical intervention to implant the shunt involves inserting into the eye a deployment device 115 that holds an intraocular shunt, and deploying the shunt within the eye 116. A deployment device 115 holding the shunt enters the eye 116 through the cornea 117 (ab interno approach). The deployment device 115 is advanced across the anterior chamber 120 (as depicted by the broken line) in what is referred to as a transpupil implant insertion. The deployment device 115 is advanced through the sclera 121 until a distal portion of the device is in proximity to the subconjunctival space 118 deep to the conjunctiva 119. The shunt is then deployed from the deployment device, producing a conduit between the anterior chamber and the subconjunctival space to allow aqueous humor to drain through the conjunctival lymphatic system.

While such ab interno subconjunctival filtration procedures have been successful in relieving intraocular pressure, there is a substantial risk that the intraocular shunt may be deployed too close to the conjunctiva, resulting in irritation and subsequent inflammation and/or scarring of the conjunctiva, which can cause the glaucoma filtration procedure to fail (See Yu et al., Progress in Retinal and Eye Research, 28:303-325 (2009)). Additionally, commercially available shunts that are currently utilized in such procedures are not ideal for ab interno subconjunctival placement due to the length of the shunt (i.e., too long) and/or the materials used to make the shunt (e.g., gold, polymer, titanium, or stainless steel), and can cause significant irritation to the tissue surrounding the shunt, as well as the conjunctiva, if deployed too close.

The present disclosure provides methods for implanting intraocular shunts within the sclera (i.e., intrascleral implantation) and are thus suitable for use in an glaucoma filtration procedure (ab interno or ab externo). In some embodiments of the methods disclosed herein, the implanted shunt forms a passage from the anterior chamber of the eye into the sclera (i.e., intrascleral space). Design and/or deployment of an intraocular shunt such that the inlet terminates in the anterior chamber and the outlet terminates intrascleral safeguard the integrity of the conjunctiva to allow subconjunctival drainage pathways to successfully form. Additionally, drainage into the intrascleral space provides access to more lymphatic channels than just the conjunctival lymphatic system, such as the episcleral lymphatic network.

Additionally, some embodiments of the methods disclosed herein recognize that while intrascleral shunt placement avoids contact with the conjunctiva, fluid outflow from the shunt into the intrascleral space may overwhelm the natural drainage structures (e.g., the episcleral vessel complex) proximate the intrascleral space. According to some embodiments, the present disclosure can combine intrascleral shunt placement with creation of a passageway through the sclera, thereby facilitating fluid drainage from the intrascleral space. Such a passageway facilitates diffusion of fluid into the subconjunctival and suprachoroidal spaces. Accordingly, the advantages of intrascleral shunt placement are recognized and the additional drainage passageway prevents the natural drainage structures proximate the intrascleral space from becoming overwhelmed with fluid output from the shunt.

Embodiments of Intraocular Shunts

According to some embodiments, the present disclosure provides intraocular shunts that are configured to form a drainage pathway from the anterior chamber of the eye to the intrascleral space. In particular, according to some embodiments, the intraocular shunts have a length that is sufficient to form a drainage pathway from the anterior chamber of the eye to the intrascleral space. The length of the shunt is important for achieving placement specifically in the intrascleral space. A shunt that is too long will extend beyond the intrascleral space and irritate the conjunctiva which can cause the filtration procedure to fail, as previously described. A shunt that is too short will not provide sufficient access to drainage pathways such as the episcleral lymphatic system or the conjunctival lymphatic system.

According to some embodiments, shunts used in methods disclosed herein may be any length that allows for drainage of aqueous humor from an anterior chamber of an eye to the intrascleral space. Exemplary shunts range in length from about 1 mm to about 10 mm or between about 2 mm to about 6 mm, or any specific value within said ranges. In certain embodiments, the length of the shunt is between about 2 mm to about 4 mm, or any specific value within said range. According to some embodiments, the intraocular shunts disclosed herein can be particularly suitable for use in an ab intern glaucoma filtration procedure. Commercially available shunts that are currently used in ab intern filtration procedures are typically made of a hard, inflexible material such as gold, polymer, titanium, or stainless steel, and cause substantial irritation of the eye tissue, resulting in ocular inflammation such as subconjunctival blebbing or endophthalmitis. Some embodiments of the methods disclosed herein may be conducted using any commercially available shunts, such as the Optonol Ex-PRESS™ mini Glaucoma shunt, and the Solx DeepLight Gold™ Micro-Shunt.

In some embodiments, the intraocular shunts disclosed herein can be flexible, and have an elasticity modulus that is substantially identical to the elasticity modulus of the surrounding tissue in the implant site. As such, some embodiments of the intraocular shunts disclosed herein can be easily bendable, do not erode or cause a tissue reaction, and do not migrate once implanted. Thus, when implanted in the eye using an ab interno procedure, such as the methods described herein, some embodiments of the intraocular shunts disclosed herein do not induce substantial ocular inflammation such as subconjunctival blebbing or endophthalmitis. Additional exemplary features of some embodiments of intraocular shunts are discussed in further detail below.

Tissue Compatible Shunts

In certain aspects, the present disclosure generally provides shunts composed of a material that has an elasticity modulus that is compatible with an elasticity modulus of tissue surrounding the shunt. In this manner, some embodiments of the shunts can be flexibility matched with the surrounding tissue, and thus will remain in place after implantation without the need for any type of anchor that interacts with the surrounding tissue. Consequently, some embodiments of the shunt will maintain fluid flow away for an anterior chamber of the eye after implantation without causing irritation or inflammation to the tissue surrounding the eye.

Elastic modulus, or modulus of elasticity, is a mathematical description of an object or substance's tendency to be deformed elastically when a force is applied to it. The elastic modulus of an object is defined as the slope of its stress-strain curve in the elastic deformation region:

$$\lambda \stackrel{def}{=} \frac{\text{Stress}}{\text{Strain}}$$

where lambda ($\lambda$) is the elastic modulus, stress is the force causing the deformation divided by the area to which the force is applied; and strain is the ratio of the change caused by the stress to the original state of the object. The elasticity modulus may also be known as Young's modulus (E), which describes tensile elasticity, or the tendency of an object to deform along an axis when opposing forces are applied along that axis. Young's modulus is defined as the ratio of tensile stress to tensile strain. For further description regarding elasticity modulus and Young's modulus, see for example Gere (Mechanics of Materials, 6th Edition, 2004, Thomson), the content of which is incorporated by reference herein in its entirety.

The elasticity modulus of any tissue can be determined by one of skill in the art. See for example Samani et al. (Phys. Med. Biol. 48:2183, 2003); Erkamp et al. (Measuring The Elastic Modulus Of Small Tissue Samples, Biomedical Engineering Department and Electrical Engineering and Computer Science Department University of Michigan Ann Arbor, Mich. 48109-2125; and Institute of Mathematical Problems in Biology Russian Academy of Sciences, Pushchino, Moscow Region 142292 Russia); Chen et al. (IEEE Trans. Ultrason. Ferroelec. Freq. Control 43:191-194, 1996); Hall, (In 1996 Ultrasonics Symposium Proc., pp. 1193-1196, IEEE Cat. No. 96CH35993, IEEE, New York, 1996); and Parker (Ultrasound Med. Biol. 16:241-246, 1990), each of which provides methods of determining the elasticity modulus of body tissues. The content of each of these is incorporated by reference herein in its entirety.

The elasticity modulus of tissues of different organs is known in the art. For example, Pierscionek et al. (Br J Ophthalmol, 91:801-803, 2007) and Friberg (Experimental Eye Research, 473:429-436, 1988) show the elasticity modulus of the cornea and the sclera of the eye. The content of each of these references is incorporated by reference herein in its entirety. Chen, Hall, and Parker show the elasticity modulus of different muscles and the liver. Erkamp shows the elasticity modulus of the kidney.

Some embodiments of the shunts can be composed of a material that is compatible with an elasticity modulus of tissue surrounding the shunt. In certain embodiments, the material has an elasticity modulus that is substantially identical to the elasticity modulus of the tissue surrounding the shunt. In other embodiments, the material has an elasticity modulus that is greater than the elasticity modulus of the tissue surrounding the shunt. Exemplary materials includes biocompatible polymers, such as polycarbonate, polyethylene, polyethylene terephthalate, polyimide, polystyrene, polypropylene, poly(styrene-b-isobutylene-b-styrene), or silicone rubber.

In some embodiments, the shunt can be composed of a material that has an elasticity modulus that is compatible with the elasticity modulus of tissue in the eye, particularly scleral tissue. In certain embodiments, compatible materials are those materials that are softer than scleral tissue or marginally harder than scleral tissue, yet soft enough to prohibit shunt migration. The elasticity modulus for anterior scleral tissue is about 2.9±1.4×106 N/m2, and 1.8±1.1×106 N/m2 for posterior scleral tissue. See Friberg (Experimental Eye Research, 473:429-436, 1988). An exemplary material is cross linked gelatin derived from Bovine or Porcine Collagen.

The present disclosure encompasses shunts of different shapes and different dimensions, and some embodiments of the shunts disclosed herein may be any shape or any dimension that may be accommodated by the eye. In certain embodiments, the intraocular shunt is of a cylindrical shape and has an outside cylindrical wall and a hollow interior. The shunt may have an inside diameter from about 10 μm to about 250 μm, an outside diameter from about 100 μm to about 450 μm, and a length from about 2 mm to about 10 mm.

Shunts Reactive to Pressure

Figure 5:
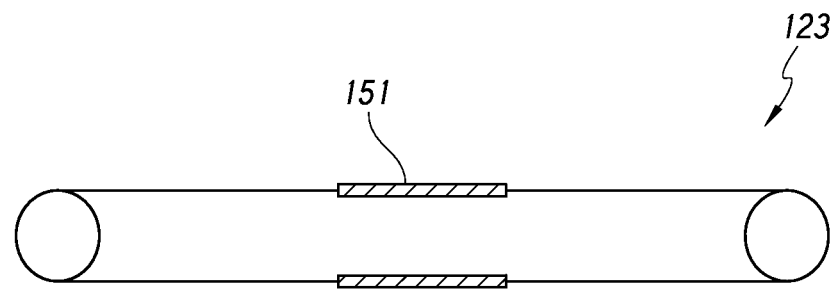
FIG. 5 provides a schematic of a shunt having a flexible portion, according to some embodiments.

In other aspects, the present disclosure generally provides shunts in which a portion of the shunt is composed of a flexible material that is reactive to pressure, i.e., the diameter of the flexible portion of the shunt fluctuates depending upon the pressures exerted on that portion of the shunt. FIG. 5 provides a schematic of a shunt 123 having a flexible portion 151. In this figure, the flexible portion 151 is shown in the middle of the shunt 123. However, the flexible portion 151 may be located in any portion of the shunt, such as the proximal or distal portion of the shunt. In certain embodiments, the entire shunt is composed of the flexible material, and thus the entire shunt is flexible and reactive to pressure.

The flexible portion 151 of the shunt 123 acts as a valve that regulates fluid flow through the shunt. The human eye produces aqueous humor at a rate of about 2 μl/min for about 3 ml/day. The entire aqueous volume is about 0.25 ml. When the pressure in the anterior chamber falls after surgery to about 7 mmHg to about 8 mmHg, it is assumed the majority of the aqueous humor is exiting the eye through the implant since venous backpressure prevents any significant outflow through normal drainage structures (e.g., the trabecular meshwork).

After implantation, intraocular shunts have pressure exerted upon them by tissues surrounding the shunt (e.g., scleral tissue such as the sclera channel and the sclera exit) and pressure exerted upon them by aqueous humor flowing through the shunt. The flow through the shunt, and thus the pressure exerted by the fluid on the shunt, is calculated by the equation:

$$\Phi = \frac{dV}{dT} = v\pi R^2 = \frac{\pi R^4}{8\eta}\left(\frac{-\Delta P}{\Delta x}\right) = \frac{\pi R^4}{8\eta}\frac{|\Delta P|}{L}$$

where Φ is the volumetric flow rate; V is a volume of the liquid poured (cubic meters); t is the time (seconds); v is mean fluid velocity along the length of the tube (meters/second); x is a distance in direction of flow (meters); R is the internal radius of the tube (meters); ΔP is the pressure difference between the two ends (pascals); η is the dynamic fluid viscosity (pascal-second (Pa·s)); and L is the total length of the tube in the x direction (meters).

Figure 6A:
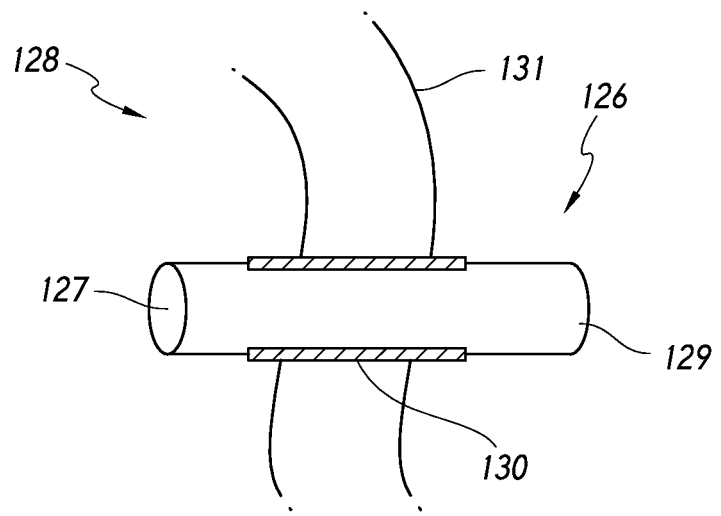
FIGS. 6A-6C provide schematics of a shunt implanted into an eye for regulation of fluid flow from the anterior chamber of the eye to a drainage structure of the eye, according to some embodiments.

FIG. 6A provides a schematic of a shunt 126 implanted into an eye for regulation of fluid flow from the anterior chamber of the eye to an area of lower pressure (e.g., the intrascleral space). The shunt is implanted such that a proximal end 127 of the shunt 126 resides in the anterior chamber 128 of the eye, and a distal end 129 of the shunt 126 resides outside of the anterior chamber to conduct aqueous humor from the anterior chamber to an area of lower pressure. A flexible portion 130 of the shunt 126 spans at least a portion of the sclera of the eye. As shown in FIG. 6A, the flexible portion spans an entire length of the sclera 131.

Figure 6B:
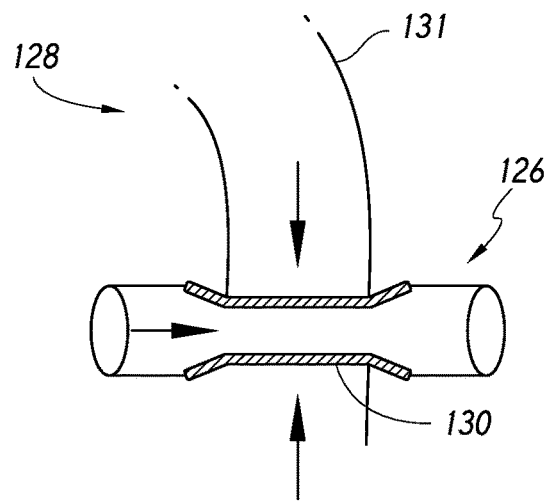

When the pressure exerted on the flexible portion 130 of the shunt 126 by sclera 131 (vertical arrows) is greater than the pressure exerted on the flexible portion 130 of the shunt 126 by the fluid flowing through the shunt (horizontal arrow), the flexible portion 130 decreases in diameter, restricting flow through the shunt 126 (FIG. 6B). The restricted flow results in aqueous humor leaving the anterior chamber 128 at a reduced rate.

Figure 6C:
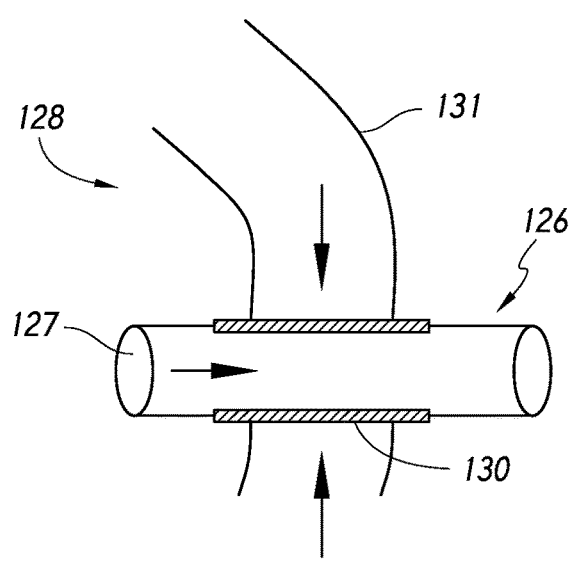

When the pressure exerted on the flexible portion 130 of the shunt 126 by the fluid flowing through the shunt (horizontal arrow) is greater than the pressure exerted on the flexible portion 130 of the shunt 126 by the sclera 131 (vertical arrows), the flexible portion 130 increases in diameter, increasing flow through the shunt 126 (FIG. 6C). The increased flow results in aqueous humor leaving the anterior chamber 128 at an increased rate.

The present disclosure encompasses shunts of different shapes and different dimensions, and some embodiments of the shunts disclosed herein may be any shape or any dimension that may be accommodated by the eye. In certain embodiments, the intraocular shunt is of a cylindrical shape and has an outside cylindrical wall and a hollow interior. The shunt may have an inside diameter from about 10 μm to about 250 μm, an outside diameter from about 100 μm to about 450 μm, and a length from about 2 mm to about 10 mm.

In some embodiments, the shunt has a length of about 6 mm and an inner diameter of about 64 μm. With these dimensions, the pressure difference between the proximal end of the shunt that resides in the anterior chamber and the distal end of the shunt that resides outside the anterior chamber is about 4.3 mmHg. Such dimensions thus allow the implant to act as a controlled valve and protect the integrity of the anterior chamber.

It will be appreciated that different dimensioned implants may be used. For example, shunts that range in length from about 2 mm to about 10 mm and have a range in inner diameter from about 10 μm to about 100 μm allow for pressure control from about 0.5 mmHg to about 20 mmHg.

The material of the flexible portion and the thickness of the wall of the flexible portion will determine how reactive the flexible portion is to the pressures exerted upon it by the surrounding tissue and the fluid flowing through the shunt. Generally, with a certain material, the thicker the flexible portion, the less responsive the portion will be to pressure. In certain embodiments, the flexible portion is a gelatin or other similar material, and the thickness of the gelatin material forming the wall of the flexible portion ranges from about 10 μm thick to about 100 μm thick.

In a certain embodiment, the gelatin used for making the flexible portion is known as gelatin Type B from bovine skin. An exemplary gelatin is PB Leiner gelatin from bovine skin, Type B, 225 Bloom, USP. Another material that may be used in the making of the flexible is available from Sigma Chemical Company of St. Louis, Mo. under Code G-9382. Still other suitable gelatins include bovine bone gelatin, porcine bone gelatin and human-derived gelatins. In addition to gelatins, the flexible portion may be made of hydroxypropyl methylcellulose (HPMC), collagen, polylactic acid, polyglycolic acid, hyaluronic acid and glycosaminoglycans.

In certain embodiments, the gelatin is cross-linked. Cross-linking increases the inter- and intramolecular binding of the gelatin substrate. Any method for cross-linking the gelatin may be used. In some embodiments, the formed gelatin is treated with a solution of a cross-linking agent such as, but not limited to, glutaraldehyde. Other suitable compounds for cross-linking include 1-ethyl-3-(3-(dimethylaminopropyl) carbodiimide (EDC). Cross-linking by radiation, such as gamma or electron beam (e-beam) may be alternatively employed.

In one embodiment, the gelatin is contacted with a solution of about 25% glutaraldehyde for a selected period of time. One suitable form of glutaraldehyde is a grade 1G5882 glutaraldehyde available from Sigma Aldridge Company of Germany, although other glutaraldehyde solutions may also be used. The pH of the glutaraldehyde solution should be in the range of about 7 to about 7.8 and, more particularly, about 7.35 to about 7.44 and typically about 7.4+/−0.01. If necessary, the pH may be adjusted by adding a suitable amount of a base such as sodium hydroxide as needed.

Methods for forming the flexible portion of the shunt are shown for example in Yu et al. (U.S. patent application number 2008/0108933), the content of which is incorporated by reference herein in its entirety. In an exemplary protocol, the flexible portion may be made by dipping a core or substrate such as a wire of a suitable diameter in a solution of gelatin. The gelatin solution is typically prepared by dissolving a gelatin powder in de-ionized water or sterile water for injection and placing the dissolved gelatin in a water bath at a temperature of about 55° C. with thorough mixing to ensure complete dissolution of the gelatin. In one embodiment, the ratio of solid gelatin to water is about 10% to about 50% gelatin by weight to about 50% to about 90% by weight of water. In an embodiment, the gelatin solution includes about 40% by weight, gelatin dissolved in water. The resulting gelatin solution should be devoid of air bubbles and has a viscosity that is between about 200 centipoise ("cp") to about 500 cp and more particularly between about 260 cp and about 410 cp.

Once the gelatin solution has been prepared, in accordance with the method described above, supporting structures such as wires having a selected diameter are dipped into the solution to form the flexible portion. Stainless steel wires coated with a biocompatible, lubricious material such as polytetrafluoroethylene (Teflon) are preferred.

Typically, the wires are gently lowered into a container of the gelatin solution and then slowly withdrawn. The rate of movement is selected to control the thickness of the coat. In addition, it is preferred that the tube be removed at a constant rate in order to provide the desired coating. To ensure that the gelatin is spread evenly over the surface of the wire, in one embodiment, the wires may be rotated in a stream of cool air which helps to set the gelatin solution and affix film onto the wire. Dipping and withdrawing the wire supports may be repeated several times to further ensure even coating of the gelatin. Once the wires have been sufficiently coated with gelatin, the resulting gelatin films on the wire may be dried at room temperature for at least 1 hour, and more preferably, about 10 hours to about 24 hours. Apparatus for forming gelatin tubes are described in Yu et al. (U.S. patent application number 2008/0108933).

Once dried, the formed flexible portions may be treated with a cross-linking agent. In one embodiment, the formed flexible portion may be cross-linked by dipping the wire (with film thereon) into the 25% glutaraldehyde solution, at pH of from about 7.0 to about 7.8 and more preferably from about 7.35 to about 7.44 at room temperature for at least about 4 hours and preferably from about 10 to about 36 hours, depending on the degree of cross-linking desired. In one embodiment, the formed flexible portion is contacted with a cross-linking agent such as glutaraldehyde for at least about 16 hours. Cross-linking can also be accelerated when it is performed a high temperatures. It is believed that the degree of cross-linking is proportional to the bioabsorption time of the shunt once implanted. In general, the more cross-linking, the longer the survival of the shunt in the body.

The residual glutaraldehyde or other cross-linking agent is removed from the formed flexible portion by soaking the tubes in a volume of sterile water for injection. The water may optionally be replaced at regular intervals, circulated or re-circulated to accelerate diffusion of the unbound glutaraldehyde from the tube. The tubes are washed for a period of a few hours to a period of a few months with the ideal time being from about 3 days to about 14 days. The now cross-linked gelatin tubes may then be dried (cured) at ambient temperature for a selected period of time. It has been observed that a drying period of from about 48 to about 96 hours and more typically 3 days (i.e., 72 hours) may be preferred for the formation of the cross-linked gelatin tubes.

Where a cross-linking agent is used, it may be desirable to include a quenching agent in the method of making the flexible portion. Quenching agents remove unbound molecules of the cross-linking agent from the formed flexible portion. In certain cases, removing the cross-linking agent may reduce the potential toxicity to a patient if too much of the cross-linking agent is released from the flexible portion. In certain embodiments, the formed flexible portion is contacted with the quenching agent after the cross-linking treatment and, may be included with the washing/rinsing solution. Examples of quenching agents include glycine or sodium borohydride.

After the requisite drying period, the formed and cross-linked flexible portion is removed from the underlying supports or wires. In one embodiment, wire tubes may be cut at two ends and the formed gelatin flexible portion slowly removed from the wire support. In another embodiment, wires with gelatin film thereon may be pushed off using a plunger or tube to remove the formed gelatin flexible portion.

Multi-Port Shunts

Other aspects of the present disclosure generally provide multi-port shunts. Such shunts reduce probability of the shunt clogging after implantation because fluid can enter or exit the shunt even if one or more ports of the shunt become clogged with particulate. In certain embodiments, the shunt includes a hollow body defining a flow path and more than two ports, in which the body is configured such that a proximal portion receives fluid from the anterior chamber of an eye and a distal portion directs the fluid to drainage structures associated with the intrascleral space.

Figure 7A:
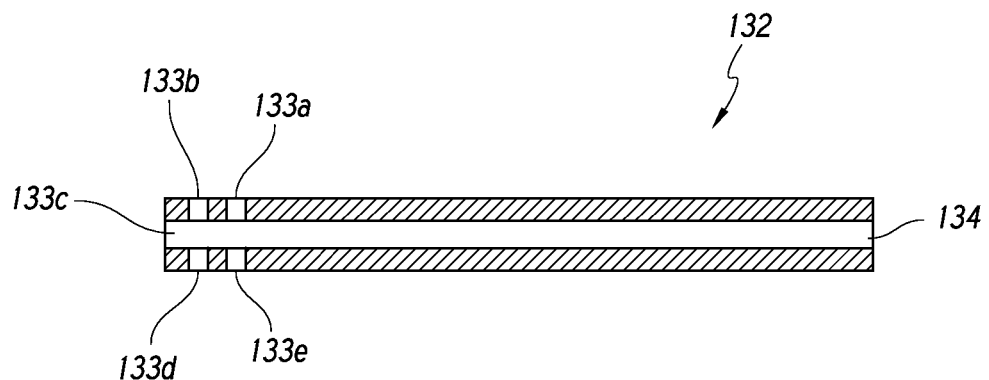
FIG. 7A shows an embodiment of a shunt in which the proximal portion of the shunt includes more than one port and the distal portion of the shunt includes a single port.
Figure 7B:
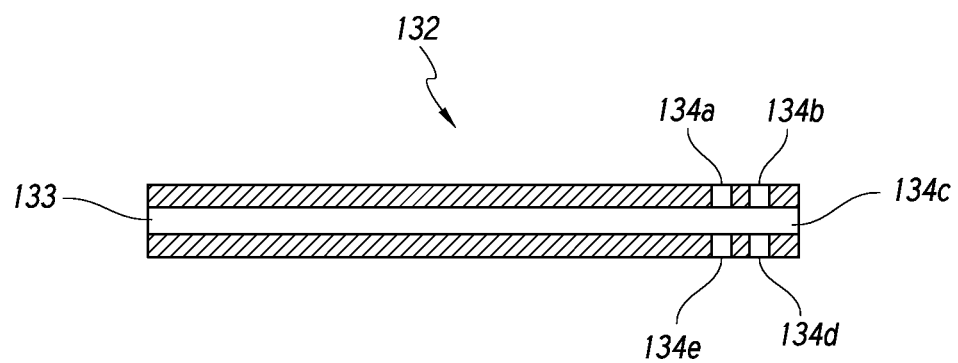
FIG. 7B shows another embodiment of a shunt in which the proximal portion includes a single port and the distal portion includes more than one port.
Figure 7C:
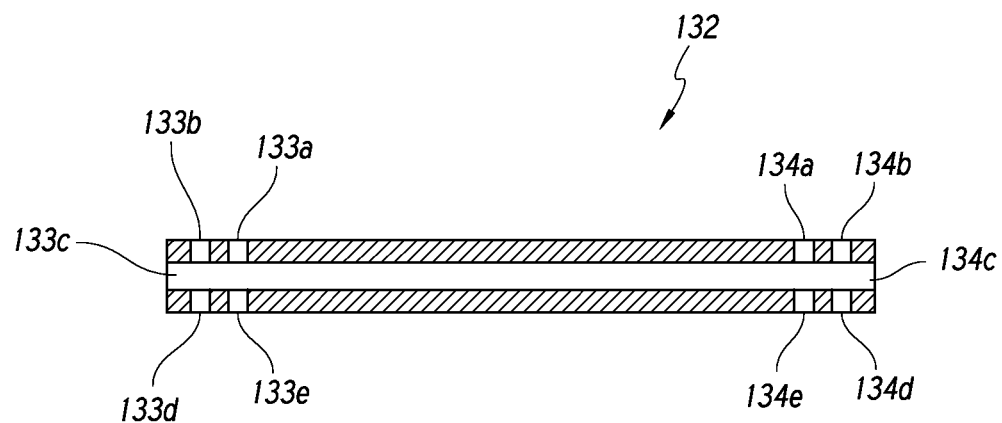
FIG. 7C shows another embodiment of a shunt in which the proximal portions include more than one port and the distal portions include more than one port.

The shunt may have many different configurations. FIG. 7A shows an embodiment of a shunt 132 in which the proximal portion of the shunt (i.e., the portion disposed within the anterior chamber of the eye) includes more than one port (designated as numbers 133a to 133e) and the distal portion of the shunt (i.e., the portion that is located in the intrascleral space) includes a single port 134. FIG. 7B shows another embodiment of a shunt 132 in which the proximal portion includes a single port 133 and the distal portion includes more than one port (designated as numbers 134a to 134e). FIG. 7C shows another embodiment of a shunt 132 in which the proximal portions include more than one port (designated as numbers 133a to 133e) and the distal portions include more than one port (designated as numbers 134a to 134e). While FIGS. 7A-7C show shunts having ports at the proximal portion, distal portion, or both, those shunts are only exemplary embodiments. The ports may be located along any portion of the shunt, and some embodiments of the shunts disclosed herein include all shunts having more than two ports. For example, some embodiments of the shunts disclosed herein may include at least three ports, at least four ports, at least five ports, at least 10 ports, at least 15 ports, or at least 20 ports.

The ports may be positioned in various different orientations and along various different portions of the shunt. In certain embodiments, at least one of the ports is oriented at an angle to the length of the body. In certain embodiments, at least one of the ports is oriented 90° to the length of the body. See for example FIG. 7A, which depicts ports 133a, 133b, 133d, and 133e as being oriented at a 90° angle to port 133c.

Figure 8A:
FIGS. 8A-8B show different embodiments of multi-port shunts having different diameter ports.
Figure 8B:

The ports may have the same or different inner diameters. In certain embodiments, at least one of the ports has an inner diameter that is different from the inner diameters of the other ports. FIGS. 8A and 8B show an embodiment of a shunt 132 having multiple ports (133a and 133b) at a proximal end and a single port 134 at a distal end. FIG. 8A shows that port 133b has an inner diameter that is different from the inner diameters of ports 133a and 134. In this figure, the inner diameter of port 133b is less than the inner diameter of ports 133a and 134. An exemplary inner diameter of port 133b is from about 20 μm to about 40 μm, particularly about 30 μm. In other embodiments, the inner diameter of port 133b is greater than the inner diameter of ports 133a and 134. See, for example, FIG. 8B.

The present disclosure encompasses shunts of different shapes and different dimensions, and the some embodiments of the shunts disclosed herein may be any shape or any dimension that may be accommodated by the eye. In certain embodiments, the intraocular shunt is of a cylindrical shape and has an outside cylindrical wall and a hollow interior. The shunt may have an inside diameter from about 10 μm to about 250 μm, an outside diameter from about 100 μm to about 450 μm, and a length from about 0.5 mm to about 20 mm. Some embodiments of the shunts disclosed herein may be made from any biocompatible material. An exemplary material is gelatin. Methods of making shunts composed of gelatin are described above.

Shunts with Overflow Ports

Other aspects of the present disclosure generally provide shunts with overflow ports. Those shunts are configured such that the overflow port remains partially or completely closed until there is a pressure build-up within the shunt sufficient to force open the overflow port. Such pressure build-up typically results from particulate partially or fully clogging an entry or an exit port of the shunt. Such shunts reduce probability of the shunt clogging after implantation because fluid can enter or exit the shunt by the overflow port even if one port of the shunt becomes clogged with particulate.

Figure 9A:
FIGS. 9A-9C provide schematics of shunts having a slit located along a portion of the length of the shunt, according to some embodiments.
Figure 9B:
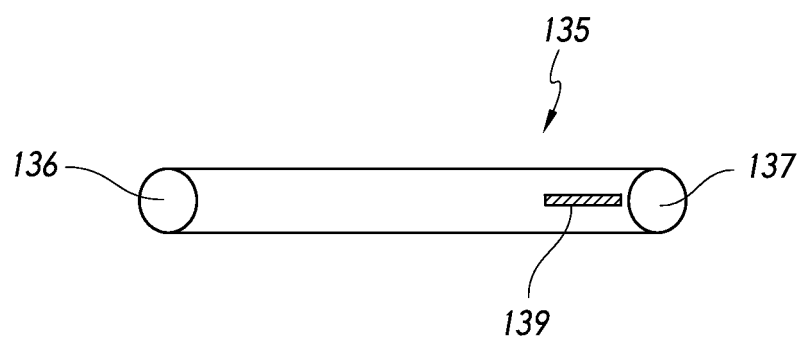
Figure 9C:
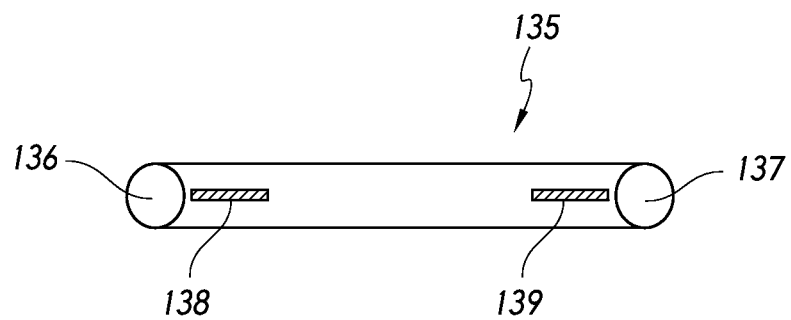

In certain embodiments, the shunt includes a hollow body defining an inlet configured to receive fluid from an anterior chamber of an eye and an outlet configured to direct the fluid to the intrascleral space, the body further including at least one slit. The slit may be located at any place along the body of the shunt. FIG. 9A shows a shunt 135 having an inlet 136, an outlet 137, and a slit 138 located in proximity to the inlet 136. FIG. 9B shows a shunt 135 having an inlet 136, an outlet 137, and a slit 139 located in proximity to the outlet 137. FIG. 9C shows a shunt 135 having an inlet 136, an outlet 137, a slit 138 located in proximity to the inlet 136, and a slit 139 located in proximity to the outlet 137.

Figure 10:
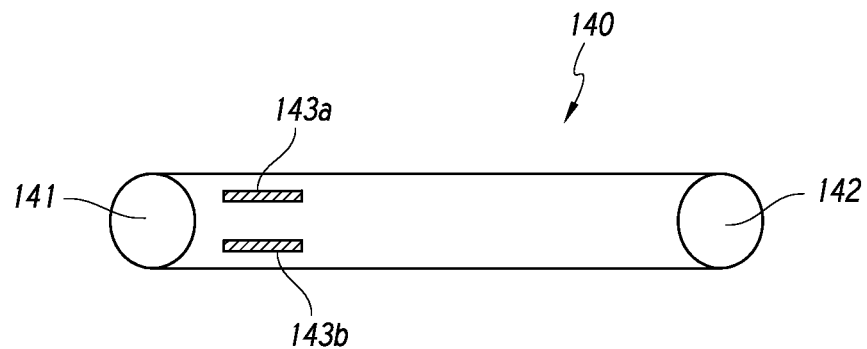
FIG. 10 depicts a shunt having multiple slits along a length of the shunt, according to some embodiments.

While FIGS. 9A-9C show shunts have only a single overflow port at the proximal portion, the distal portion, or both the proximal and distal portions, those shunts are only exemplary embodiments. The overflow port(s) may be located along any portion of the shunt, and some embodiments of the shunts disclosed herein include shunts having more than one overflow port. In certain embodiments, some embodiments of the shunts disclosed herein include more than one overflow port at the proximal portion, the distal portion, or both. For example, FIG. 10 shows a shunt 140 having an inlet 141, an outlet 142, and slits 143a and 143b located in proximity to the inlet 141. Some embodiments of the shunts disclosed herein may include at least two overflow ports, at least three overflow ports, at least four overflow ports, at least five overflow ports, at least 10 overflow ports, at least 15 overflow ports, or at least 20 overflow ports. In certain embodiments, some embodiments of the shunts disclosed herein include two slits that overlap and are oriented at 90° to each other, thereby forming a cross.

Figure 11:
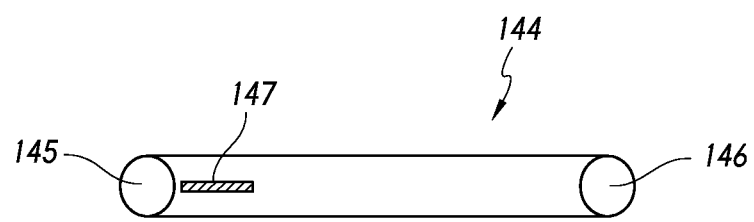
FIG. 11 depicts a shunt having a slit at a proximal end of the shunt, according to some embodiments.

In certain embodiments, the slit may be at the proximal or the distal end of the shunt, producing a split in the proximal or the distal end of the implant. FIG. 11 shows an embodiment of a shunt 144 having an inlet 145, outlet 146, and a slit 147 that is located at the proximal end of the shunt, producing a split in the inlet 145 of the shunt.

In certain embodiments, the slit has a width that is substantially the same or less than an inner diameter of the inlet. In other embodiments, the slit has a width that is substantially the same or less than an inner diameter of the outlet. In certain embodiments, the slit has a length that ranges from about 0.05 mm to about 2 mm, and a width that ranges from about 10 µm to about 200 µm. Generally, the slit does not direct the fluid unless the outlet is obstructed. However, the shunt may be configured such that the slit does direct at least some of the fluid even if the inlet or outlet is not obstructed.

The present disclosure encompasses shunts of different shapes and different dimensions, and some embodiments of the shunts disclosed herein may be any shape or any dimension that may be accommodated by the eye. In certain embodiments, the intraocular shunt is of a cylindrical shape and has an outside cylindrical wall and a hollow interior. The shunt may have an inside diameter from about 10 µm to about 250 µm, an outside diameter from about 100 µm to about 450 µm, and a length from about 2 mm to about 10 mm. Some embodiments of the shunts disclosed herein may be made from any biocompatible material. An exemplary material is gelatin. Methods of making shunts composed of gelatin are described above.

Shunts Having a Variable Inner Diameter

In other aspects, the present disclosure generally provides a shunt having a variable inner diameter. In some embodiments, the diameter increases from inlet to outlet of the shunt. By having a variable inner diameter that increases from inlet to outlet, a pressure gradient is produced and particulate that may otherwise clog the inlet of the shunt is forced through the inlet due to the pressure gradient. Further, the particulate will flow out of the shunt because the diameter only increases after the inlet.

Figure 12:
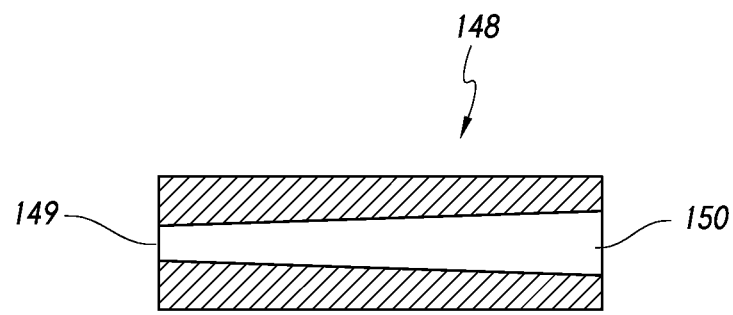
FIG. 12 provides a schematic of a shunt that has a variable inner diameter, according to some embodiments.

FIG. 12 shows an embodiment of a shunt 148 having an inlet 149 configured to receive fluid from an anterior chamber of an eye and an outlet 150 configured to direct the fluid to a location of lower pressure with respect to the anterior chamber, in which the body further includes a variable inner diameter that increases along the length of the body from the inlet 149 to the outlet 150. In certain embodiments, the inner diameter continuously increases along the length of the body, for example as shown in FIG. 12. In other embodiments, the inner diameter remains constant along portions of the length of the body.

In exemplary embodiments, the inner diameter may range in size from about 10 µm to about 200 µm, and the inner diameter at the outlet may range in size from about 15 µm to about 300 µm. The present disclosure encompasses shunts of different shapes and different dimensions, and some embodiments of the shunts disclosed herein may be any shape or any dimension that may be accommodated by the eye. In certain embodiments, the intraocular shunt is of a cylindrical shape and has an outside cylindrical wall and a hollow interior. The shunt may have an inside diameter from about 10 µm to about 250 µm, an outside diameter from about 100 µm to about 450 µm, and a length from about 2 mm to about 10 mm. Shunts of the invention may be made from any biocompatible material. An exemplary material is gelatin. Methods of making shunts composed of gelatin are described above.

Shunts Having Pronged Ends

In other aspects, the present disclosure generally provides shunts for facilitating conduction of fluid flow away from an organ, the shunt including a body, in which at least one end of the shunt is shaped to have a plurality of prongs. Such shunts reduce probability of the shunt clogging after implantation because fluid can enter or exit the shunt by any space between the prongs even if one portion of the shunt becomes clogged with particulate.

FIGS. 13A-13D show embodiments of a shunt 152 in which at least one end of the shunt 152 includes a plurality of prongs 153a-153d. FIGS. 13A-13D show embodiments in which both a proximal end and a distal end of the shunt are shaped to have the plurality of prongs. However, numerous different configurations are envisioned. For example, in certain embodiments, only the proximal end of the shunt is shaped to have the plurality of prongs. In other embodiments, only the distal end of the shunt is shaped to have the plurality of prongs.

Figure 13A:
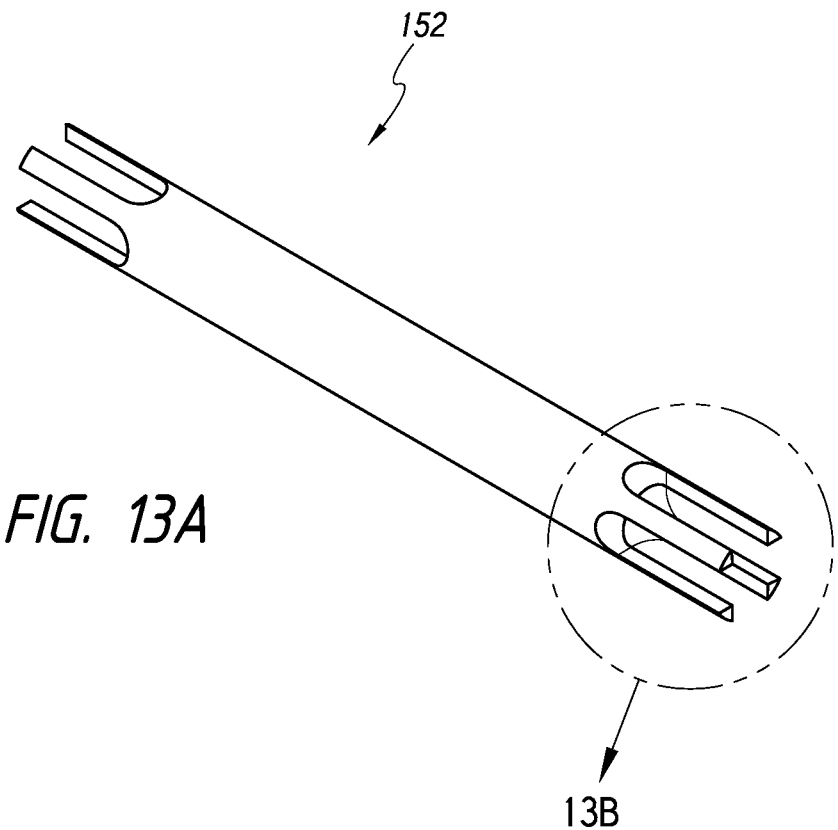
FIGS. 13A-13D depict a shunt having multiple prongs at a distal and/or proximal end, according to some embodiments.
Figure 13B:
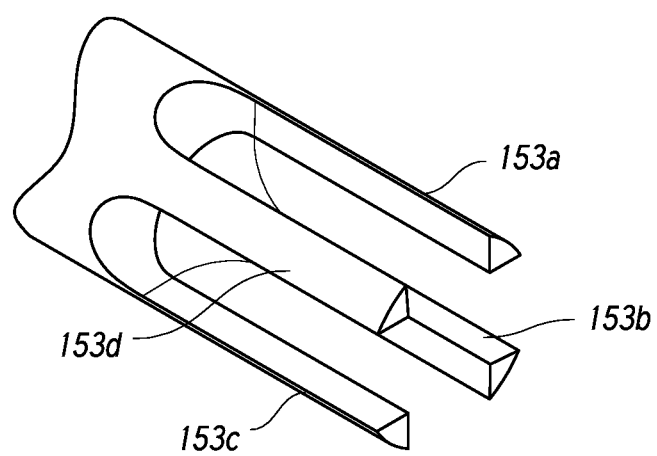
Figure 13C:
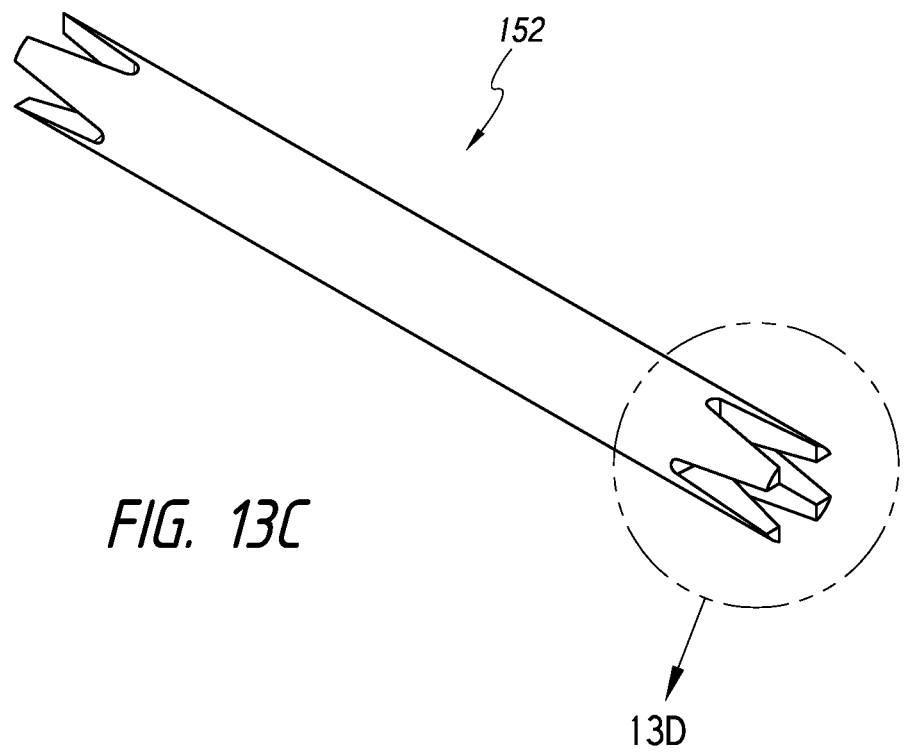
Figure 13D:
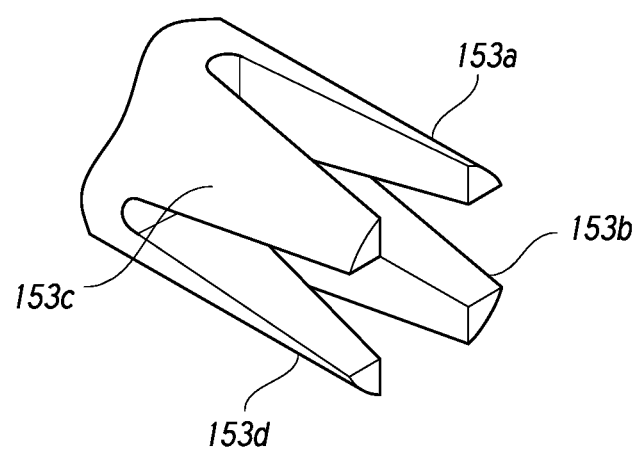

Prongs 153a-153d can have any shape (i.e., width, length, height). FIGS. 13A-13B show prongs 153a-153d as straight prongs. In this embodiment, the spacing between the prongs 153a-153d is the same. In another embodiment shown in FIGS. 13C-13D, prongs 153a-153d are tapered. In this embodiment, the spacing between the prongs increases toward a proximal and/or distal end of the shunt 152.

FIGS. 13A-13D show embodiments that include four prongs. However, some embodiments of the shunts disclosed herein may accommodate any number of prongs, such as two prongs, three prongs, four prongs, five prongs, six prongs, seven prongs, eight prongs, nine prongs, ten prongs, etc. The number of prongs chosen will depend on the desired flow characteristics of the shunt.

The present disclosure encompasses shunts of different shapes and different dimensions, and some embodiments of the shunts disclosed herein may be any shape or any dimension that may be accommodated by the eye. In certain embodiments, the intraocular shunt is of a cylindrical shape and has an outside cylindrical wall and a hollow interior. The shunt may have an inside diameter from about 10 µm to about 250 µm, an outside diameter from about 100 µm to about 450 µm, and a length from about 2 mm to about 10 mm. Some embodiments of the shunts disclosed herein may be made from any biocompatible material. An exemplary material is gelatin. Methods of making shunts composed of gelatin are described above.

Shunts Having a Longitudinal Slit

In other aspects, the present disclosure generally provides a shunt for draining fluid from an anterior chamber of an eye that includes a hollow body defining an inlet configured to receive fluid from an anterior chamber of the eye and an outlet configured to direct the fluid to a location of lower pressure with respect to the anterior chamber; the shunt being configured such that at least one end of the shunt includes a longitudinal slit. Such shunts reduce probability of the shunt clogging after implantation because the end(s) of the shunt can more easily pass particulate which would generally clog a shunt lacking the slits.

FIGS. 14A-14D show embodiments of a shunt 154 in which at least one end of the shunt 154 includes a longitudinal slit 155 that produces a top portion 156a and a bottom portion 156b in a proximal and/or distal end of the shunt 154. FIGS. 14A-14D show an embodiment in which both a proximal end and a distal end include a longitudinal slit 155 that produces a top portion 156a and a bottom portion 156b in both ends of the shunt 154. However, numerous different configurations are envisioned. For example, in certain embodiments, only the proximal end of the shunt includes longitudinal slit 155. In other embodiments, only the distal end of the shunt includes longitudinal slit 155.

Figure 14A:
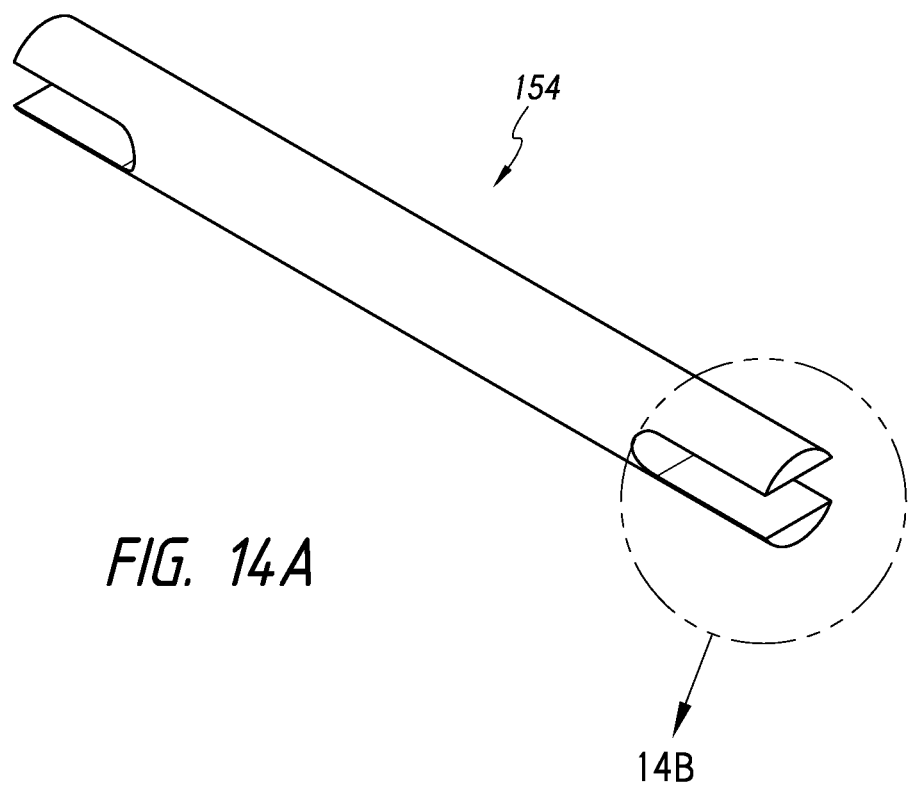
FIGS. 14A-14D depict a shunt having a longitudinal slit at a distal and/or proximal end, according to some embodiments.
Figure 14B:
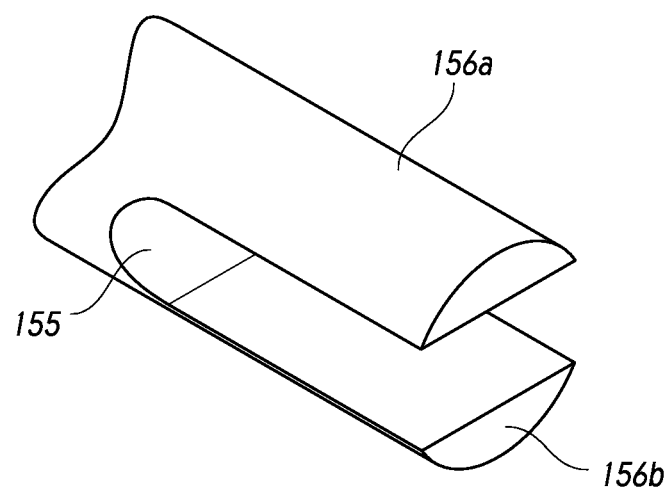
Figure 14C:
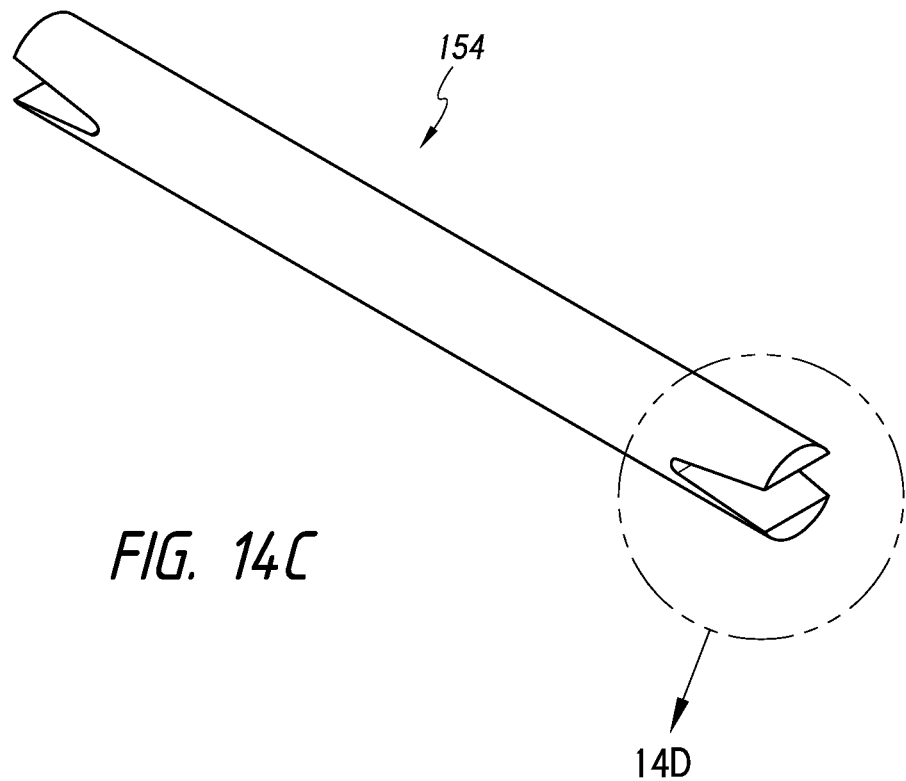
Figure 14D:
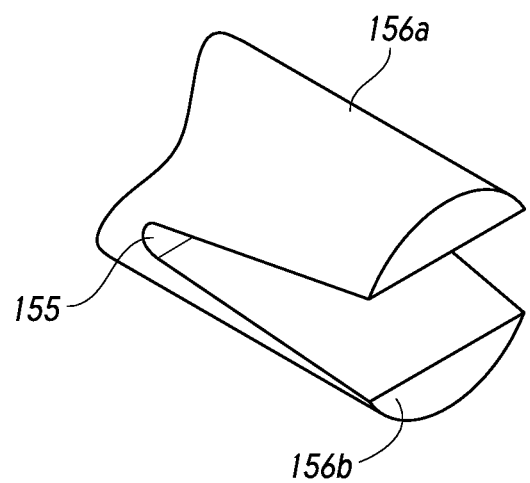

Longitudinal slit 155 can have any shape (i.e., width, length, height). FIGS. 14A-14B show a longitudinal slit 155 that is straight such that the space between the top portion 156a and the bottom portion 156b remains the same along the length of the slit 155. In another embodiment shown in FIGS. 14C-14D, longitudinal slit 155 is tapered. In this embodiment, the space between the top portion 145a and the bottom portion 156b increases toward a proximal and/or distal end of the shunt 154.

The present disclosure encompasses shunts of different shapes and different dimensions, and the some embodiments of the shunts disclosed herein may be any shape or any dimension that may be accommodated by the eye. In certain embodiments, the intraocular shunt is of a cylindrical shape and has an outside cylindrical wall and a hollow interior. The shunt may have an inside diameter from about 10 µm to about 250 µm, an outside diameter from about 100 µm to about 450 µm, and a length from about 2 mm to about 10 mm. Some embodiments of the shunts disclosed herein may be made from any biocompatible material. An exemplary material is gelatin. Methods of making shunts composed of gelatin are described above.

Pharmaceutical Agents

In certain embodiments, some embodiments of the shunts disclosed herein may be coated or impregnated with at least one pharmaceutical and/or biological agent or a combination thereof. The pharmaceutical and/or biological agent may coat or impregnate an entire exterior of the shunt, an entire interior of the shunt, or both. Alternatively, the pharmaceutical or biological agent may coat and/or impregnate a portion of an exterior of the shunt, a portion of an interior of the shunt, or both. Methods of coating and/or impregnating an intraocular shunt with a pharmaceutical and/or biological agent are known in the art. See for example, Darouiche (U.S. Pat. Nos. 7,790,183; 6,719,991; 6,558,686; 6,162,487; 5,902,283; 5,853,745; and 5,624,704) and Yu et al. (U.S. Patent App. No. 2008/0108933). The content of each of these references is incorporated by reference herein its entirety.

In certain embodiments, the exterior portion of the shunt that resides in the anterior chamber after implantation (e.g., about 1 mm of the proximal end of the shunt) is coated and/or impregnated with the pharmaceutical or biological agent. In other embodiments, the exterior of the shunt that resides in the scleral tissue after implantation of the shunt is coated and/or impregnated with the pharmaceutical or biological agent. In other embodiments, the exterior portion of the shunt that resides in the intrascleral space after implantation is coated and/or impregnated with the pharmaceutical or biological agent. In embodiments in which the pharmaceutical or biological agent coats and/or impregnates the interior of the shunt, the agent may be flushed through the shunt and into the area of lower pressure (e.g., the intrascleral space).

Any pharmaceutical and/or biological agent or combination thereof may be used with some embodiments of the shunts disclosed herein. The pharmaceutical and/or biological agent may be released over a short period of time (e.g., seconds) or may be released over longer periods of time (e.g., days, weeks, months, or even years). Exemplary agents include anti-mitotic pharmaceuticals such as Mitomycin-C or 5-Fluorouracil, anti-VEGF (such as Lucentis, Macugen, Avastin, VEGF or steroids).

Deployment Devices

Any deployment device or system known in the art may be used with some embodiments of the methods disclosed herein. In certain embodiments, deployment into the eye of an intraocular shunt according to some embodiments can be achieved using a hollow shaft configured to hold the shunt, as described herein. The hollow shaft can be coupled to a deployment device or part of the deployment device itself. Deployment devices that are suitable for deploying shunts according to some embodiments include, but are not limited to the deployment devices described in U.S. Pat. No. 6,007,511, U.S. Pat. No. 6,544,249, U.S. Publication No. 2008/0108933, U.S. Patent App. No. 61/904,429, filed on Nov. 14, 2013, and U.S. patent application Ser. No. 14/313,970, filed on Jun. 24, 2013, the contents of which are each incorporated herein by reference in their entireties. In other embodiments, the deployment devices are devices as described in co-pending and co-owned U.S. patent application Ser. No. 12/946,222 filed on Nov. 15, 2010, or deployment devices described in co-pending and co-owned U.S. patent application Ser. No. 12/946,645 filed on Nov. 15, 2010, the entire content of each of which is incorporated by reference herein.

A shunt deployment device, such as those disclosed herein, can be used to implant the shunt in accordance with a variety of potential procedures, which can be modified or updated, according to aspects of the disclosure herein, as well as future methodologies and device features. For example, as discussed and shown below with regard to FIGS. 52A-54E, a shunt deployment device can be used to implant a shunt using a variety of different procedures. The deployment device can be manual or automatic and can include features of one or more of the devices discussed or mentioned herein.

Figure 15:
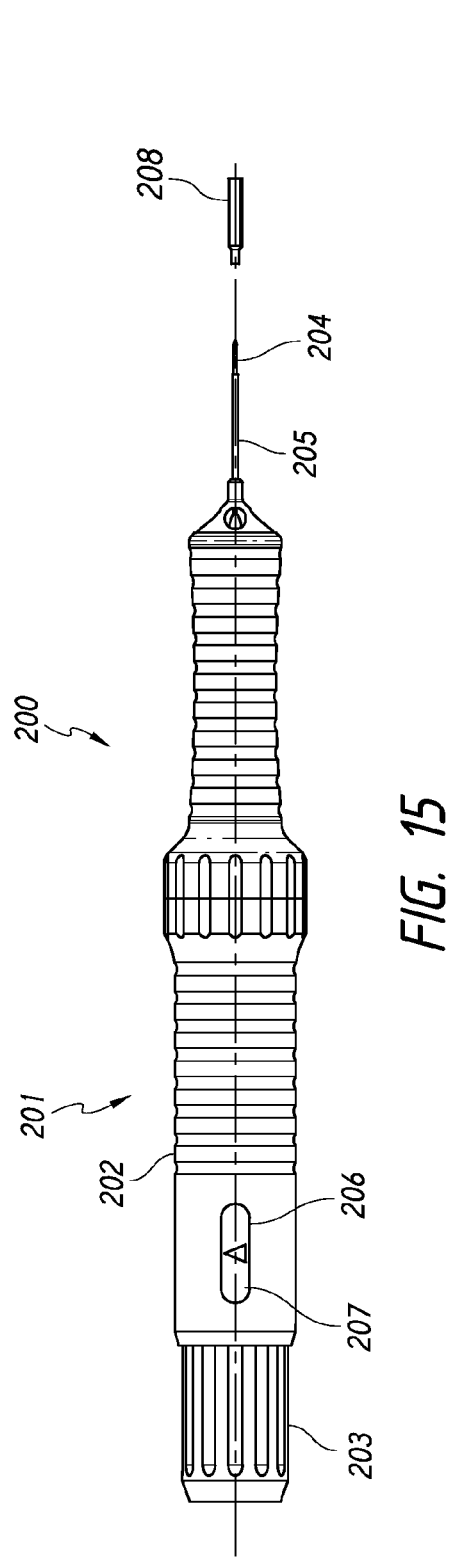
FIG. 15 is a schematic showing an embodiment of a shunt deployment device.

For example, in some embodiments, the shunts can be deployed into the eye using the deployment device 200 depicted in FIG. 15. While FIG. 15 shows a handheld, manually operated shunt deployment device, it will be appreciated that devices according to some embodiments may be coupled with robotic systems and may be completely or partially automated. As shown in FIG. 15, deployment device 200 includes a generally cylindrical body or housing 201; however, the body shape of housing 201 could be other than cylindrical. Housing 201 may have an ergonomical shape, allowing for comfortable grasping by an operator. Housing 201 is shown with optional grooves 202 to allow for easier gripping by a surgeon.

According to some embodiments, the shunt can be advanced into the eye tissue at a rate of between about 0.15 mm/sec to about 0.85 mm/sec. Further, in some embodiments, the shunt can be advanced into the eye tissue at a rate of between about 0.25 mm/sec to about 0.65 mm/sec.

Housing 201 is shown having a larger proximal portion that tapers to a distal portion. The distal portion includes a hollow sleeve 205. The hollow sleeve 205 is configured for insertion into an eye and to extend into an anterior chamber of an eye. The hollow sleeve 205 is visible within an anterior chamber of an eye. According to some embodiment, the sleeve 205 can provide a visual preview or guide for an operator as to placement of the proximal portion of the shunt within the anterior chamber of an eye, as discussed below with regard to FIGS. 52A-52E. The sleeve 205 can provide a visual reference point that may be used by an operator to hold device 100 steady during the shunt deployment process, thereby assuring optimal longitudinal placement of the shunt within the eye.

According to some embodiments, the sleeve 205 may also include an edge 231 at a distal end that provides resistance feedback to an operator upon insertion of the deployment device 200 within an eye 232 of a person during delivery of the shunt 215, as discussed below with regard to FIGS. 53A-54E. Upon advancement of the device 200 across an anterior chamber 233 of the eye 232, the hollow sleeve 205 will eventually contact the anterior chamber angle tissue, and may abut sclera 234, providing resistance feedback to an operator that no further advancement of the device 200 is necessary. A temporary guard 208 is configured to fit around sleeve 205 and extend beyond an end of sleeve 205. The edge 231 of the sleeve 205 prevents the shaft 204 from accidentally being pushed too far through the sclera 234. The guard is used during shipping of the device and protects an operator from a distal end of a hollow shaft 204 that extends beyond the end of the sleeve 205. The guard is removed prior to use of the device.

Housing 201 is open at its proximal end, such that a portion of a deployment mechanism 203 may extend from the proximal end of the housing 201. A distal end of housing 201 is also open such that at least a portion of a hollow shaft 204 may extend through and beyond the distal end of the housing 201. Housing 201 further includes a slot 206 through which an operator, such as a surgeon, using the device 200 may view an indicator 207 on the deployment mechanism 203.

Housing 201 may be made of any material that is suitable for use in medical devices. For example, housing 201 may be made of a lightweight aluminum or a biocompatible plastic material. Examples of such suitable plastic materials include polycarbonate and other polymeric resins such as DELRIN and ULTEM. In certain embodiments, housing 201 is made of a material that may be autoclaved, and thus allow for housing 201 to be re-usable. Alternatively, device 200 may be sold as a one-time-use device, and thus the material of the housing does not need to be a material that is autoclavable.

Figure 16:
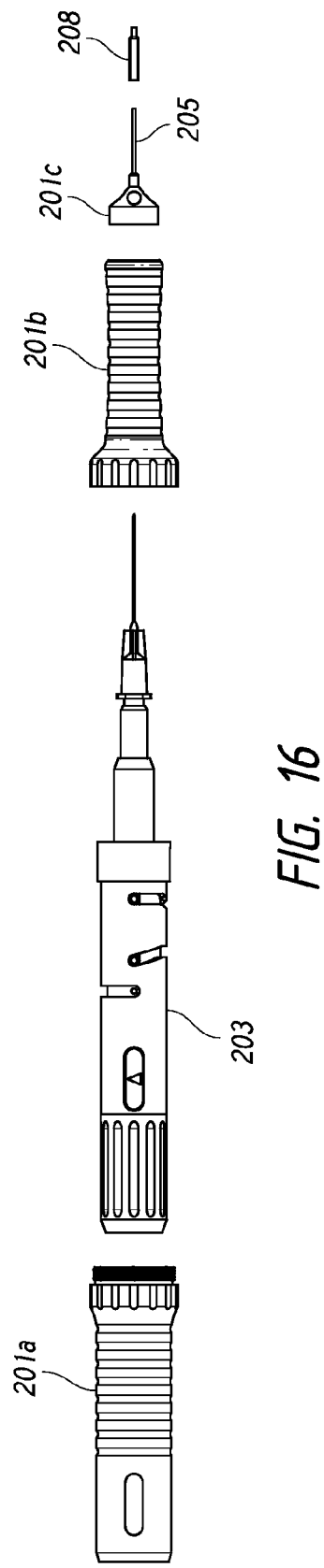
FIG. 16 shows an exploded view of the device shown in FIG. 16.

Housing 201 may be made of multiple components that connect together to form the housing. FIG. 16 shows an exploded view of deployment device 200. In this figure, housing 201 is shown having three components 201a, 201b, and 201c. The components are designed to screw together to form housing 201. FIGS. 17A-17D also show deployment mechanism 203. The housing 201 is designed such that deployment mechanism 203 fits within assembled housing 201. Housing 201 is designed such that components of deployment mechanism 203 are movable within housing 201.

FIGS. 17A-17D show different enlarged views of the deployment mechanism 203. Deployment mechanism 203 may be made of any material that is suitable for use in medical devices. For example, deployment mechanism 203 may be made of a lightweight aluminum or a biocompatible plastic material. Examples of such suitable plastic materials include polycarbonate and other polymeric resins such as DELRIN and ULTEM. In certain embodiments, deployment mechanism 203 is made of a material that may be autoclaved, and thus allow for deployment mechanism 203 to be re-usable. Alternatively, device 200 may be sold as a one-time-use device, and thus the material of the deployment mechanism does not need to be a material that is autoclavable.

Deployment mechanism 203 includes a distal portion 209 and a distal portion 210. The deployment mechanism 203 is configured such that distal portion 209 is movable within distal portion 210. More particularly, distal portion 209 is capable of partially retracting to within proximal portion 210.

In this embodiment, the distal portion 209 is shown to taper to a connection with a hollow shaft 204. This embodiment is illustrated such that the connection between the hollow shaft 204 and the distal portion 209 of the deployment mechanism 203 occurs inside the housing 201. In other embodiments, the connection between hollow shaft 204 and the distal portion 209 of the deployment mechanism 203 may occur outside of the housing 201. Hollow shaft 204 may be removable from the distal portion 209 of the deployment mechanism 203. Alternatively, the hollow shaft 204 may be permanently coupled to the distal portion 209 of the deployment mechanism 203.

Generally, hollow shaft 204 is configured to hold an intraocular shunt, such as the intraocular shunts according to some embodiments. The shaft 204 may be any length. A usable length of the shaft may be anywhere from about 5 mm to about 40 mm, and is about 15 mm in certain embodiments. In certain embodiments, the shaft is straight. In other embodiments, shaft is of a shape other than straight, for example a shaft having a bend along its length.

Figure 17C:
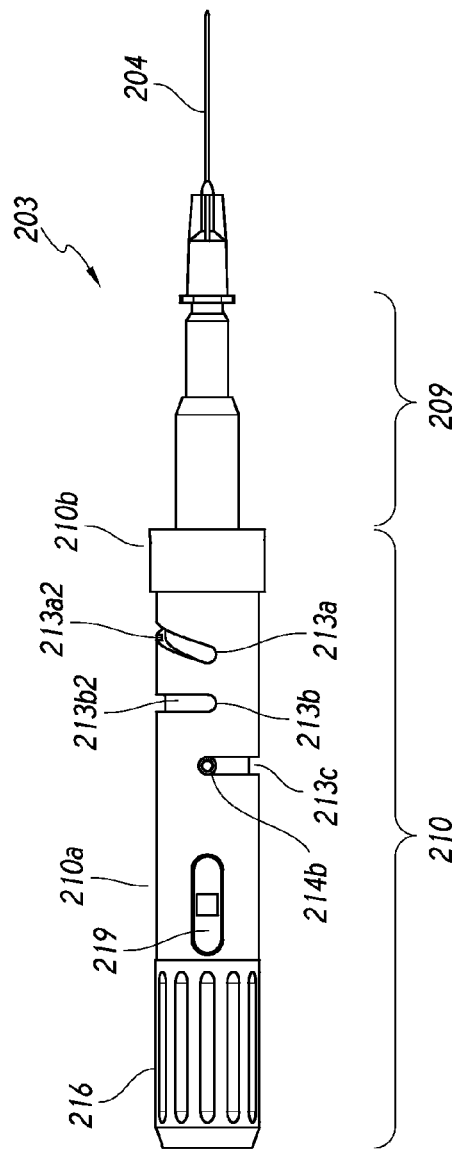
Figure 17D:
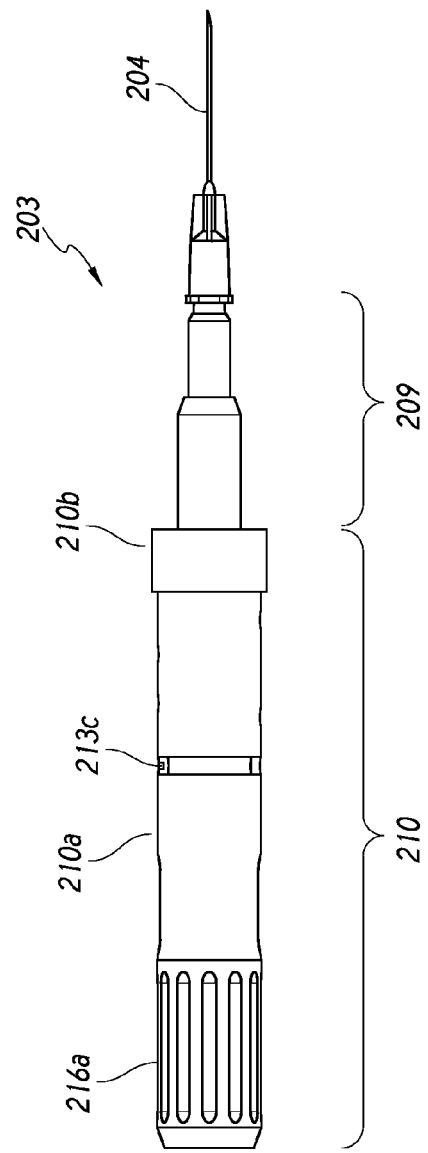

A proximal portion of the deployment mechanism includes optional grooves 216 to allow for easier gripping by an operator for easier rotation of the deployment mechanism, which will be discussed in more detail below. The proximal portion 210 of the deployment mechanism also includes at least one indicator that provides feedback to an operator as to the state of the deployment mechanism. The indicator may be any type of indicator known in the art, for example a visual indicator, an audio indicator, or a tactile indicator. FIGS. 17A and 17C show a deployment mechanism having two indicators, a ready indicator 211 and a deployed indicator 219. Ready indicator 211 provides feedback to an operator that the deployment mechanism is in a configuration for deployment of an intraocular shunt from the deployment device 200. The ready indicator 211 is shown in this embodiment as a green oval having a triangle within the oval. Deployed indicator 219 provides feedback to the operator that the deployment mechanism has been fully engaged and has deployed the shunt from the deployment device 200. The deployed indicator 219 is shown in this embodiment as a yellow oval having a black square within the oval. The indicators are located on the deployment mechanism such that when assembled, the indicators 211 and 219 may be seen through slot 206 in housing 201.

Figure 18A:
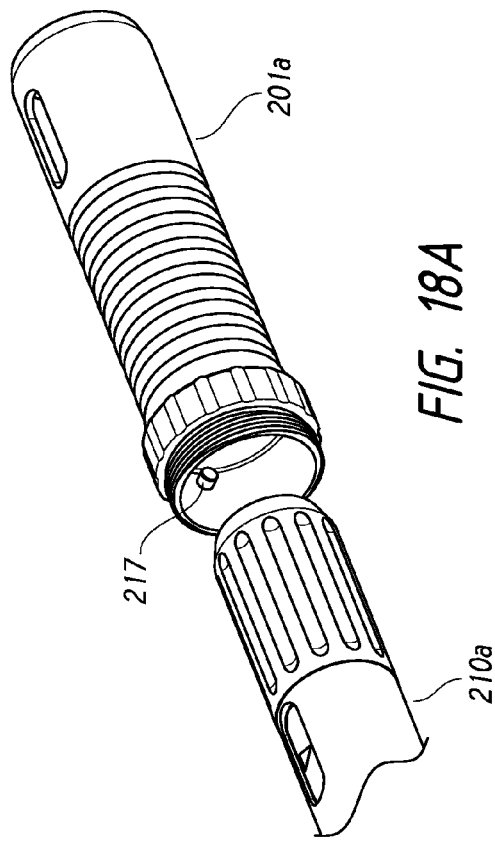
FIGS. 18A-18C are schematics showing interaction of the deployment mechanism with a portion of the housing of the deployment device, according to some embodiments.
Figure 18B:
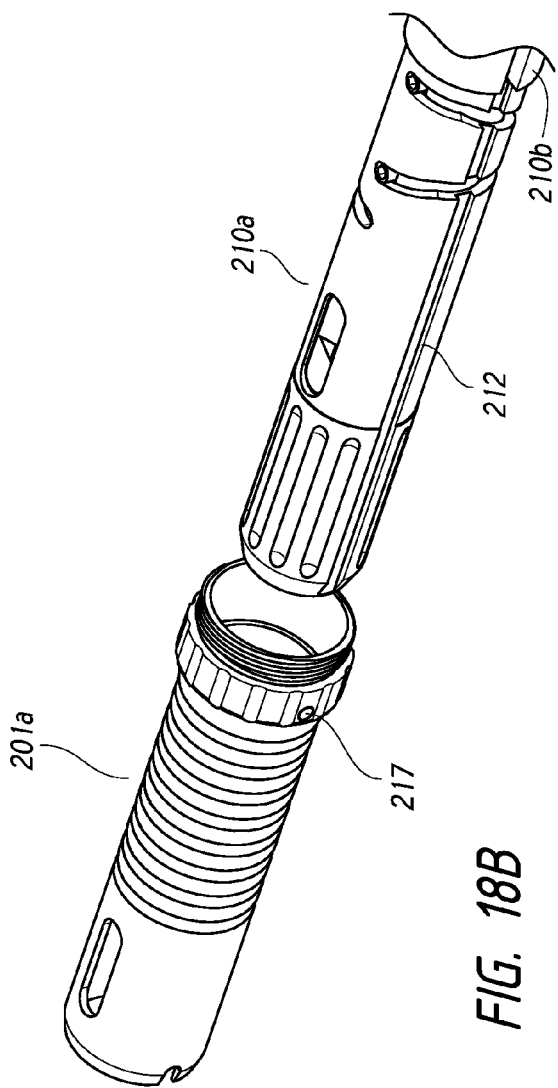
Figure 18C:
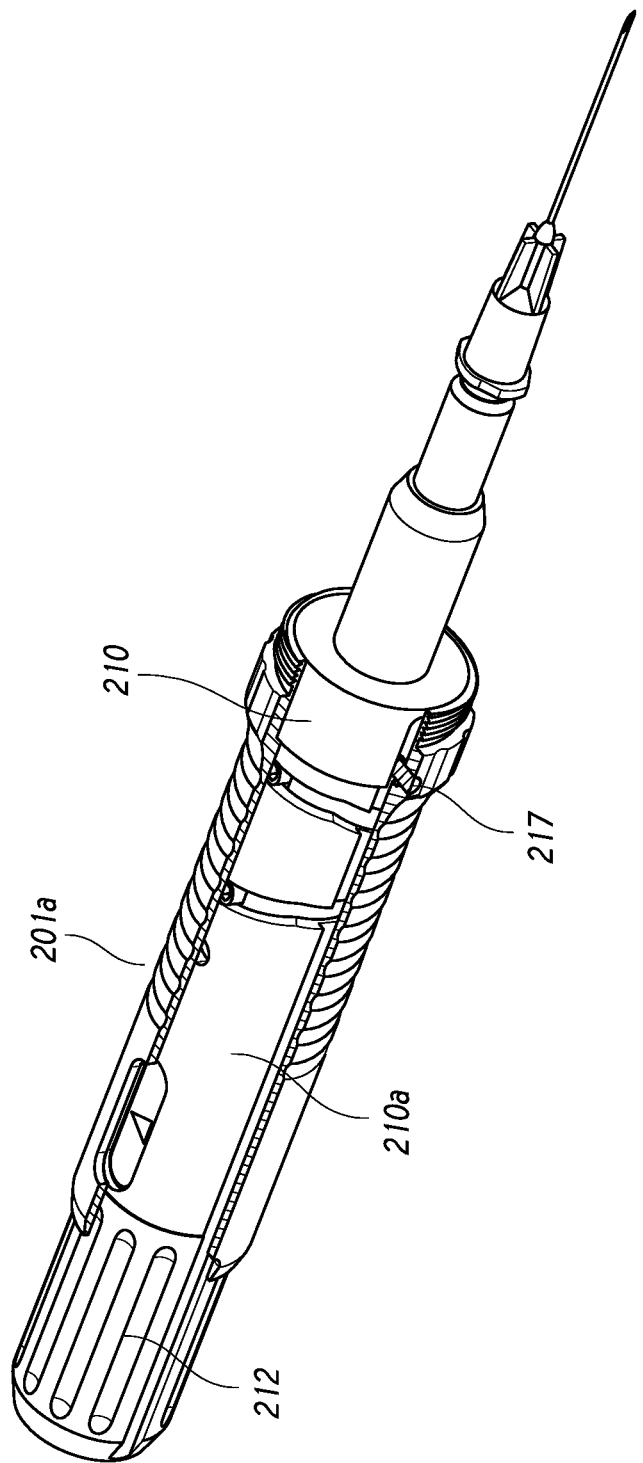

The proximal portion 210 includes a stationary portion 210b and a rotating portion 210a. The proximal portion 210 includes a channel 212 that runs part of the length of stationary portion 210b and the entire length of rotating portion 210a. The channel 212 is configured to interact with a protrusion 217 on an interior portion of housing component 201a (FIGS. 18A and 18B). During assembly, the protrusion 217 on housing component 201a is aligned with channel 212 on the stationary portion 210b and rotating portion 210a of the deployment mechanism 203. The proximal portion 210 of deployment mechanism 203 is slid within housing component 201a until the protrusion 217 sits within stationary portion 210b (FIG. 18C). Assembled, the protrusion 217 interacts with the stationary portion 210b of the deployment mechanism 203 and prevents rotation of stationary portion 210b. In this configuration, rotating portion 210a is free to rotate within housing component 201a.

Referring back to FIGS. 17A-17D, the rotating portion 210a of proximal portion 210 of deployment mechanism 203 also includes channels 213a, 213b, and 213c. Channel 213a includes a first portion 213a1 that is straight and runs perpendicular to the length of the rotating portion 210a, and a second portion 213a2 that runs diagonally along the length of rotating portion 210a, downwardly toward a proximal end of the deployment mechanism 203. Channel 213b includes a first portion 213b1 that runs diagonally along the length of the rotating portion 210a, downwardly toward a distal end of the deployment mechanism 203, and a second portion that is straight and runs perpendicular to the length of the rotating portion 210a. The point at which first portion 213a1 transitions to second portion 213a2 along channel 213a, is the same as the point at which first portion 213b1 transitions to second portion 213b2 along channel 213b. Channel 213c is straight and runs perpendicular to the length of the rotating portion 210a. Within each of channels 213a, 213b, and 213c, sit members 214a, 214b, and 214c respectively. Members 214a, 214b, and 214c are movable within channels 213a, 213b, and 213c. Members 214a, 214b, and 214c also act as stoppers that limit movement of rotating portion 210a, which thereby limits axial movement of the shaft 204.

Figure 19:
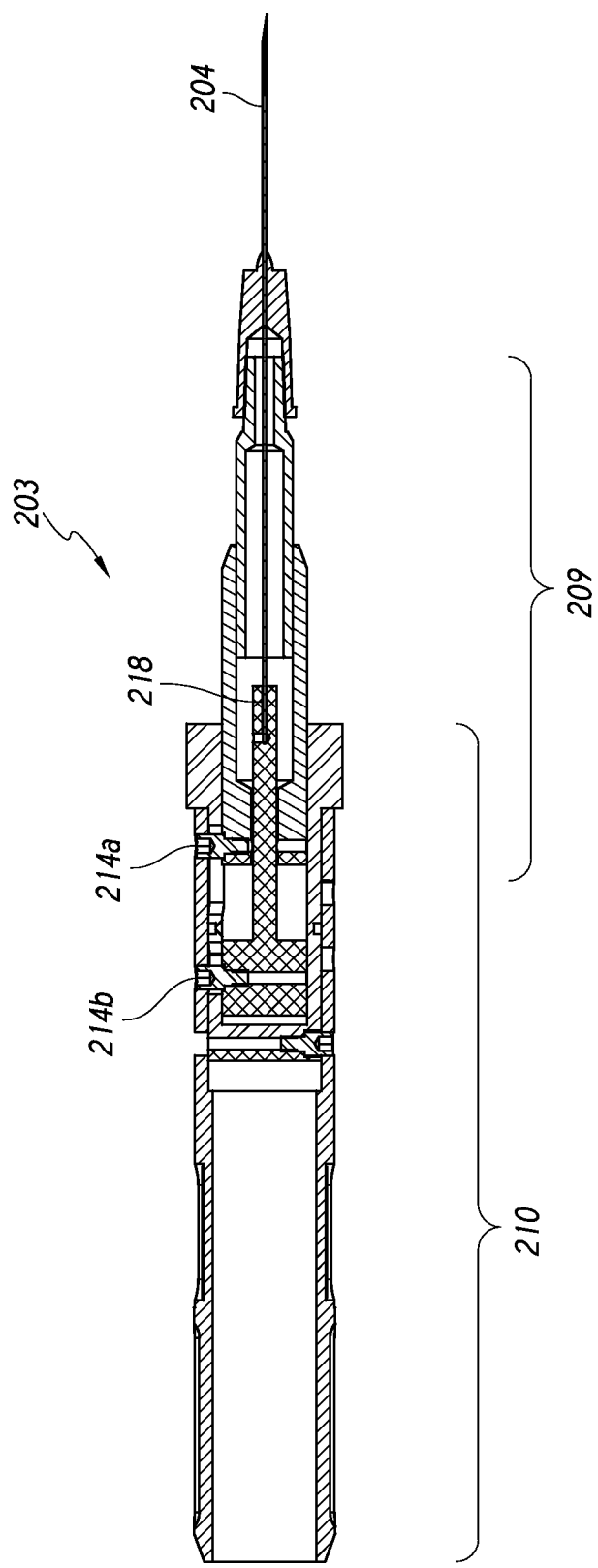
FIG. 19 shows a cross-sectional view of the deployment mechanism of the deployment device, according to some embodiments.

FIG. 19 shows a cross-sectional view of deployment mechanism 203. Member 214a is connected to the distal portion 209 of the deployment mechanism 203. Movement of member 214a results in retraction of the distal portion 209 of the deployment mechanism 203 to within the proximal portion 210 of the deployment mechanism 203. Member 214b is connected to a pusher component 218. The pusher component 218 extends through the distal portion 209 of the deployment mechanism 203 and extends into a portion of hollow shaft 204. The pusher component is involved in deployment of a shunt from the hollow shaft 204. An exemplary pusher component is a plunger. Movement of member 214b engages pusher 218 and results in pusher 218 advancing within hollow shaft 204.

Reference is now made to FIGS. 20A-22D, which accompany the following discussion regarding deployment of a shunt 215 from deployment device 200. FIG. 20A shows deployment device 200 in a pre-deployment configuration. In this configuration, shunt 215 is loaded within hollow shaft 204 (FIG. 20C). As shown in FIG. 20C, shunt 215 is only partially within shaft 204, such that a portion of the shunt is exposed. However, the shunt 215 does not extend beyond the end of the shaft 204. In other embodiments, the shunt 215 is completely disposed within hollow shaft 204. The shunt 215 is loaded into hollow shaft 204 such that the shunt abuts pusher component 218 within hollow shaft 204. A distal end of shaft 204 is beveled to assist in piercing tissue of the eye.

Additionally, in the pre-deployment configuration, a portion of the shaft 204 extends beyond the sleeve 205 (FIG. 20C). The deployment mechanism is configured such that member 214a abuts a distal end of the first portion 213a1 of channel 213a, and member 214b abuts a proximal end of the first portion 213b1 of channel 213b (FIG. 20B). In this configuration, the ready indicator 211 is visible through slot 206 of the housing 201, providing feedback to an operator that the deployment mechanism is in a configuration for deployment of an intraocular shunt from the deployment device 200 (FIG. 20A). In this configuration, the device 200 is ready for insertion into an eye (insertion configuration or pre-deployment configuration). Methods for inserting and implanting shunts are discussed in further detail below.

Once the device has been inserted into the eye and advanced to a location to where the shunt will be deployed, the shunt 215 may be deployed from the device 200. The deployment mechanism 203 is a two-stage system. The first stage is engagement of the pusher component 218 and the second stage is retraction of the distal portion 209 to within the proximal portion 210 of the deployment mechanism 203. Rotation of the rotating portion 210a of the proximal portion 210 of the deployment mechanism 203 sequentially engages the pusher component and then the retraction component.

In the first stage of shunt deployment, the pusher component is engaged and the pusher partially deploys the shunt from the deployment device. During the first stage, rotating portion 210a of the proximal portion 210 of the deployment mechanism 203 is rotated, resulting in movement of members 214a and 214b along first portions 213a1 and 213b1 in channels 213a and 213b. Since the first portion 213a1 of channel 213a is straight and runs perpendicular to the length of the rotating portion 210a, rotation of rotating portion 210a does not cause axial movement of member 214a. Without axial movement of member 214a, there is no retraction of the distal portion 209 to within the proximal portion 210 of the deployment mechanism 203. Since the first portion 213b1 of channel 213b runs diagonally along the length of the rotating portion 210a, upwardly toward a distal end of the deployment mechanism 203, rotation of rotating portion 210a causes axial movement of member 214b toward a distal end of the device. Axial movement of member 214b toward a distal end of the device results in forward advancement of the pusher component 218 within the hollow shaft 204. Such movement of pusher component 218 results in partial deployment of the shunt 215 from the shaft 204.

FIGS. 21A-21C show schematics of the deployment mechanism at the end of the first stage of deployment of the shunt from the deployment device. As is shown FIG. 21A, members 214a and 214b have finished traversing along first portions 213a1 and 213b1 of channels 213a and 213b. Additionally, pusher component 218 has advanced within hollow shaft 204 (FIG. 21B), and shunt 215 has been partially deployed from the hollow shaft 204 (FIG. 21C). As is shown in these figures, a portion of the shunt 215 extends beyond an end of the shaft 204.

In the second stage of shunt deployment, the retraction component is engaged and the distal portion of the deployment mechanism is retracted to within the proximal portion of the deployment mechanism, thereby completing deployment of the shunt from the deployment device. During the second stage, rotating portion 210a of the proximal portion 210 of the deployment mechanism 203 is further rotated, resulting in movement of members 214a and 214b along second portions 213a2 and 213b2 in channels 213a and 213b. Since the second portion 213b2 of channel 213b is straight and runs perpendicular to the length of the rotating portion 210a, rotation of rotating portion 210a does not cause axial movement of member 214b. Without axial movement of member 214b, there is no further advancement of pusher component 218. Since the second portion 213a2 of channel 213a runs diagonally along the length of the rotating portion 210a, downwardly toward a proximal end of the deployment mechanism 203, rotation of rotating portion 210a causes axial movement of member 214a toward a proximal end of the device. Axial movement of member 214a toward a proximal end of the device results in retraction of the distal portion 209 to within the proximal portion 210 of the deployment mechanism 203. Retraction of the distal portion 209, results in retraction of the hollow shaft 204. Since the shunt 215 abuts the pusher component 218, the shunt remains stationary as the hollow shaft 204 retracts from around the shunt 215 (FIG. 21C). The shaft 204 retracts almost completely to within the sleeve 205. During both stages of the deployment process, the sleeve 205 remains stationary and in a fixed position.

Figure 22C:
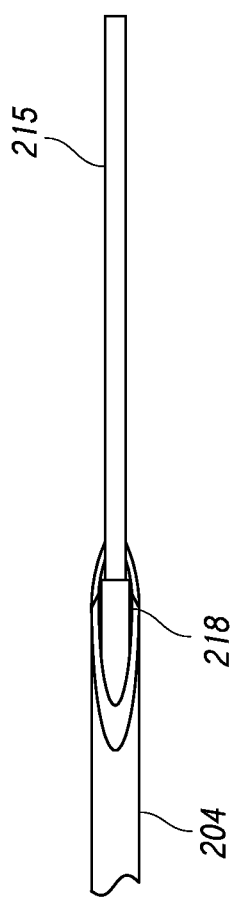
FIG. 22C shows an enlarged view of the distal portion of the deployment device after retraction of the shaft with the pusher abutting the shunt, according to some embodiments.
Figure 22D:
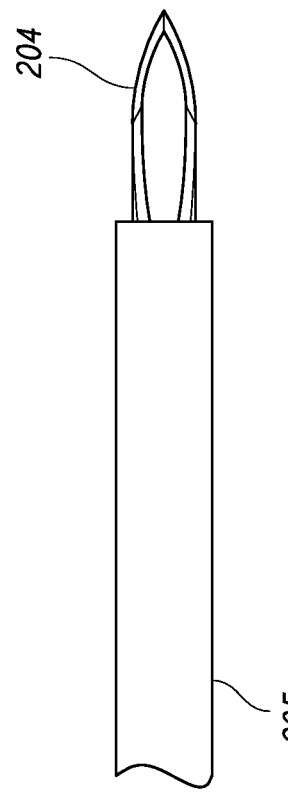
FIG. 22D shows an enlarged view of the distal portion of the deployment device after deployment of the shunt, according to some embodiments.
Figure 23:
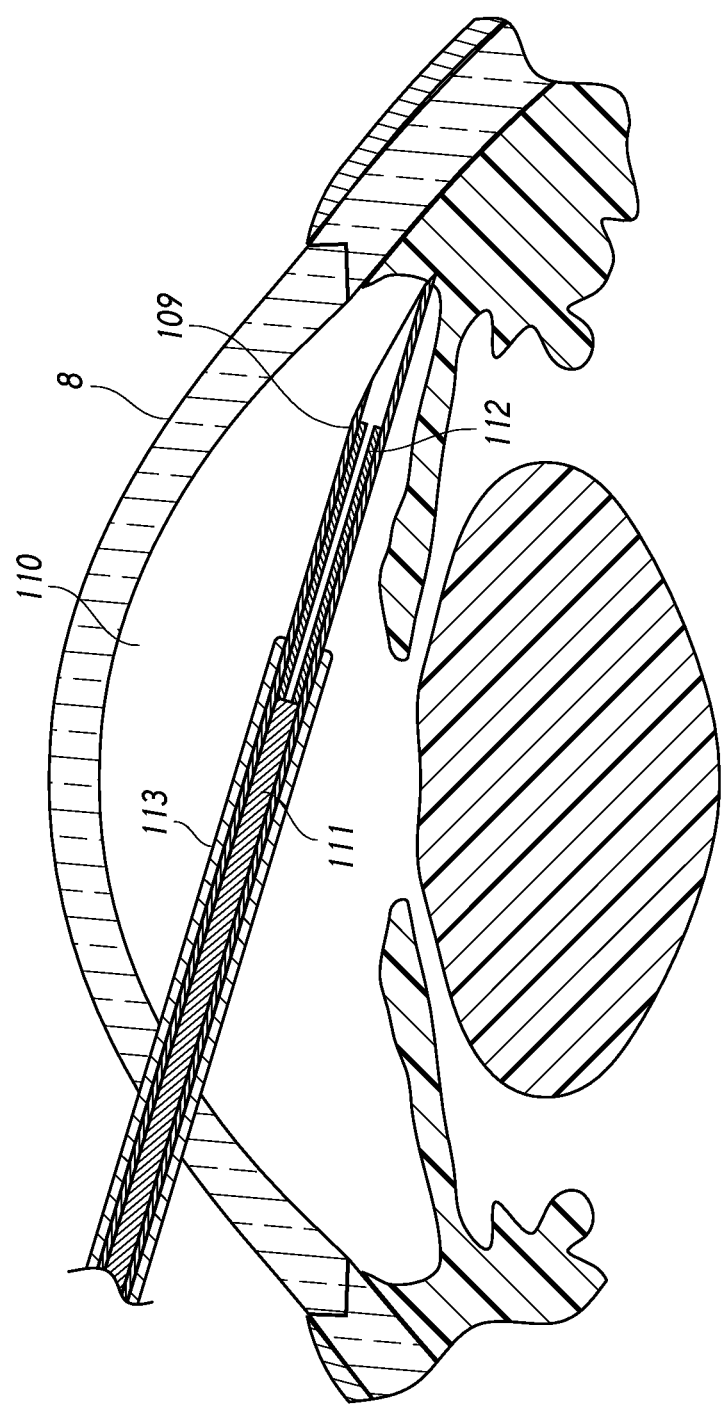
FIGS. 23-30 depict a sequence for ab interno shunt placement, according to some embodiments.

FIGS. 22A-22D show schematics of the device 200 after deployment of the shunt 215 from the device 200. FIG. 22B shows a schematic of the deployment mechanism at the end of the second stage of deployment of the shunt from the deployment device. As is shown in FIG. 22B, members 214a and 214b have finished traversing along second portions 213a1 and 213b1 of channels 213a and 213b. Additionally, distal portion 209 has retracted to within proximal portion 210, thus resulting in retraction of the hollow shaft 204 to within the sleeve 205. FIG. 22D shows an enlarged view of the distal portion of the deployment device after deployment of the shunt. This figure shows that the hollow shaft 204 is not fully retracted to within the sleeve 205 of the deployment device 200. However, in certain embodiments, the shaft 204 may completely retract to within the sleeve 205.

Methods for Intrascleral Shunt Placement

Some embodiments of the methods disclosed herein can involve creating an opening in the sclera (e.g., by piercing the sclera with a delivery device), and positioning a shunt in the anterior chamber of the eye such that the shunt terminates adjacent an opening formed in the sclera. In some embodiments, such placement can permit flow through the shunt to reach the intrascleral space, thereby facilitating fluid flow through both the opening and the intrascleral space. The outlet of the shunt may be positioned in different places within the intrascleral space. For example, the outlet of the shunt may be positioned within the sclera (e.g., within deep and superficial layers or tissue of the sclera). Alternatively, the outlet of the shunt may be positioned such that the outlet is even with or superficial to the opening through the sclera.

Methods of implanting intraocular shunts are known in the art. Shunts may be implanted using an ab externo approach (entering through the conjunctiva and inwards through the sclera) or an ab interno approach (entering through the cornea, across the anterior chamber, through the trabecular meshwork and sclera). The deployment device may be any device that is suitable for implanting an intraocular shunt into an eye. Such devices generally include a shaft connected to a deployment mechanism. In some devices, a shunt is positioned over an exterior of the shaft and the deployment mechanism works to deploy the shunt from an exterior of the shaft. In other devices, the shaft is hollow and the shunt is at least partially disposed in the shaft. In those devices, the deployment mechanism works to deploy the shunt from within the shaft. Depending on the device, a distal portion of the shaft may be sharpened or blunt, or straight or curved.

Ab-Interno Approach

Ab interno approaches for implanting an intraocular shunt in the subconjunctival space are shown for example in Yu et al. (U.S. Pat. No. 6,544,249 and U.S. Patent Publication No. 2008/0108933) and Prywes (U.S. Pat. No. 6,007,511), the contents of each of which are incorporated by reference herein in its entirety. An exemplary ab-interno method employs a transpupil approach and involves creating a first opening in the sclera of an eye, advancing a shaft configured to hold an intraocular shunt across an anterior chamber of an eye and through the sclera to create a second opening in the sclera, retracting the shaft through the second opening to within the sclera (i.e., the intrascleral space), deploying the shunt from the shaft such that the shunt forms a passage from the anterior chamber of the eye to the intrascleral space of the eye, such that an outlet of the shunt is positioned so that at least some of the fluid that exits the shunt flows through the second opening in the sclera, and withdrawing the shaft from the eye. The first opening in the sclera may be made in any manner. In certain embodiments, the shaft creates the first opening in the sclera. In other embodiments, a tool other than the shaft creates the first opening in the sclera.

In certain embodiments, some embodiments of the methods disclosed herein can generally involve inserting into the eye a hollow shaft configured to hold an intraocular shunt. In certain embodiments, the hollow shaft is a component of a deployment device that may deploy the intraocular shunt. The shunt is then deployed from the shaft into the eye such that the shunt forms a passage from the anterior chamber into the sclera (i.e., the intrascleral space). The hollow shaft is then withdrawn from the eye.

Figure 24:
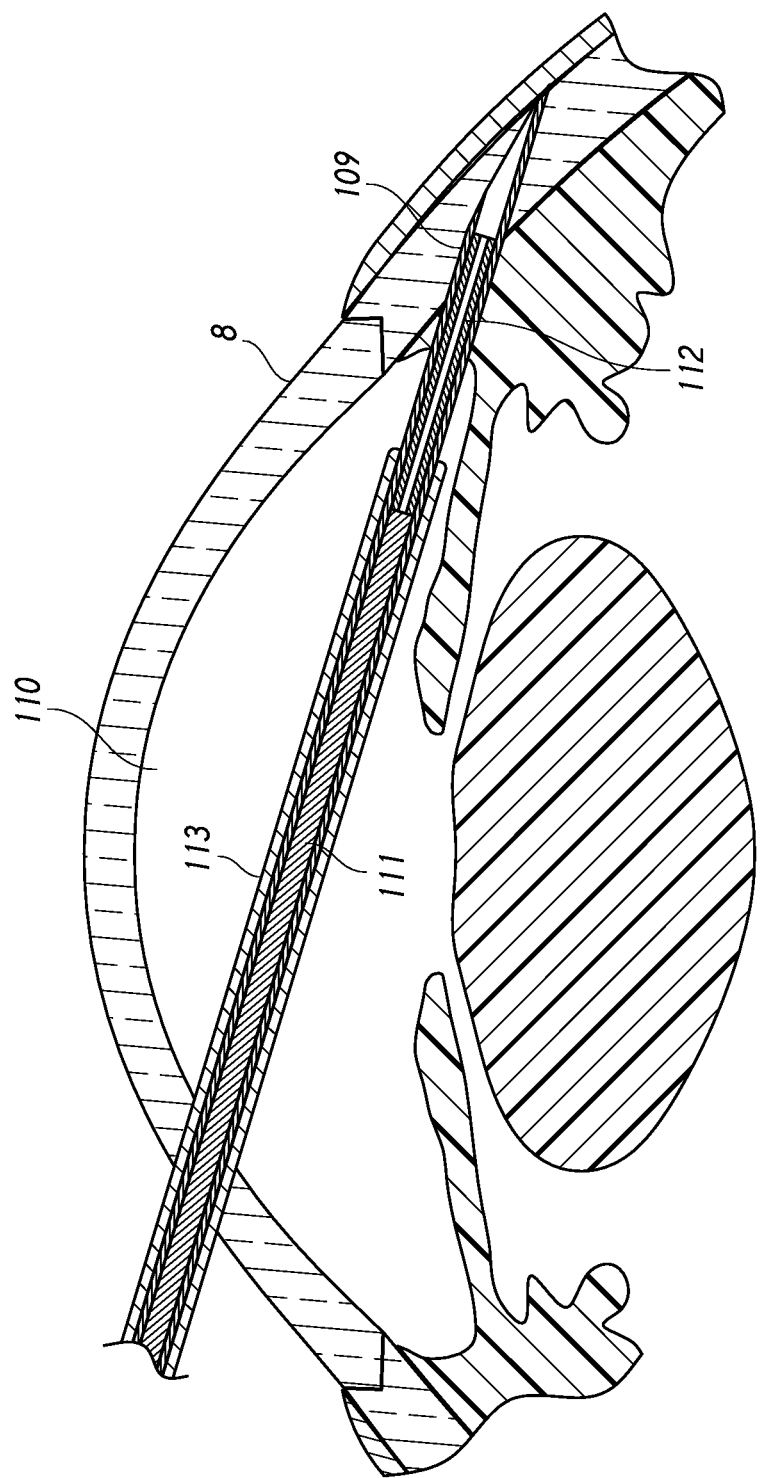
Figure 25:
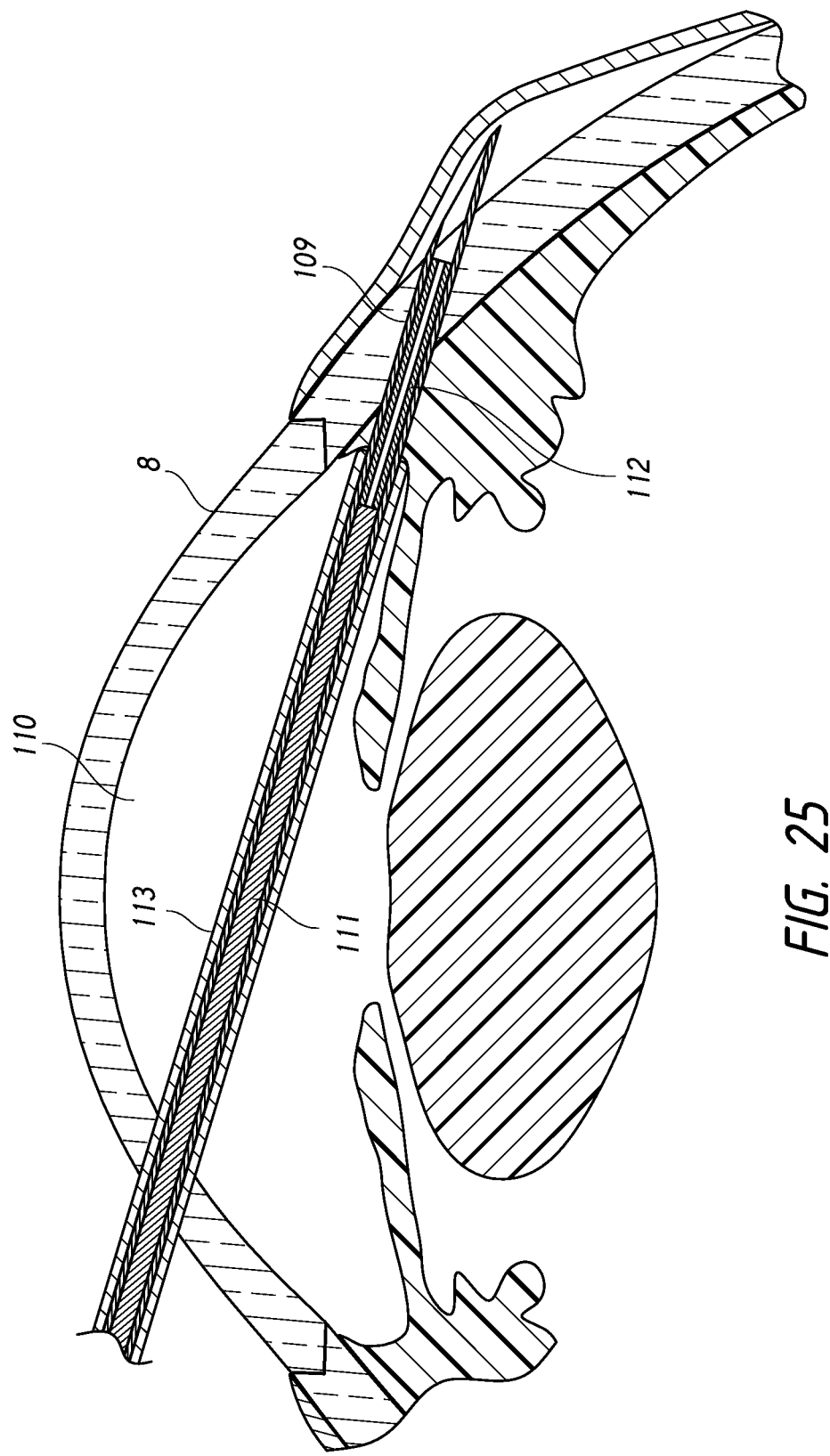
Figure 26:
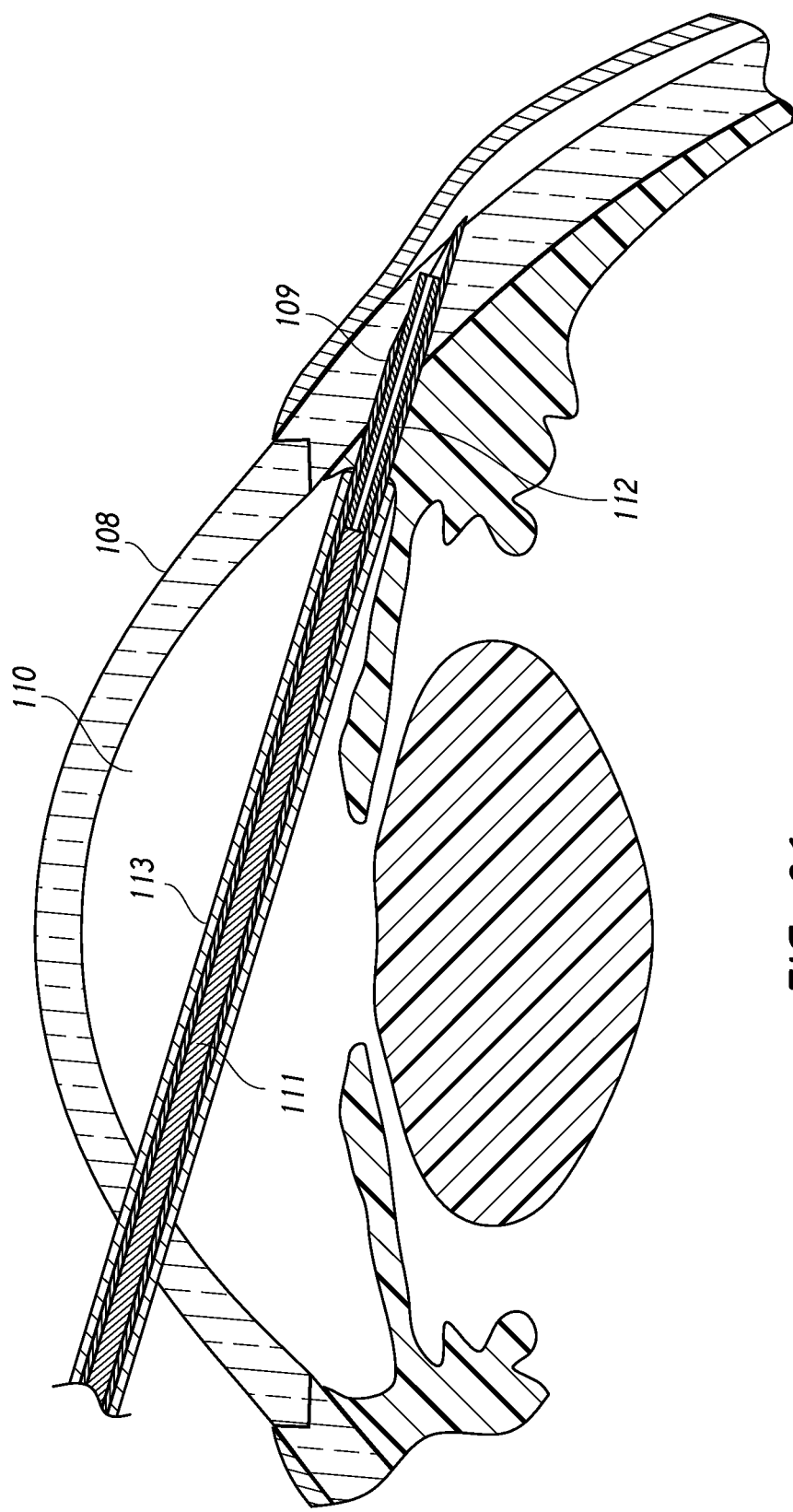
Figure 27:
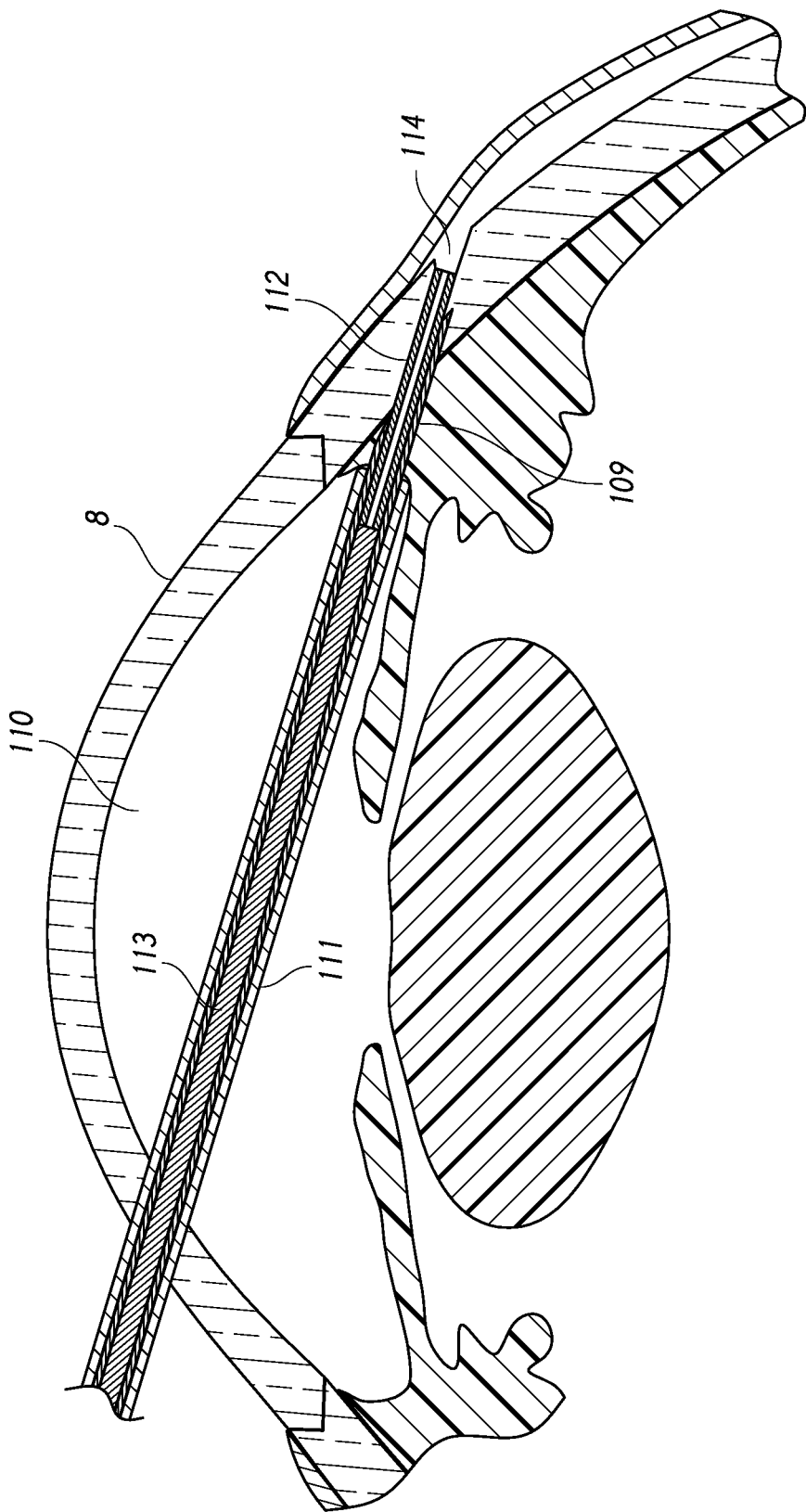
Figure 28:
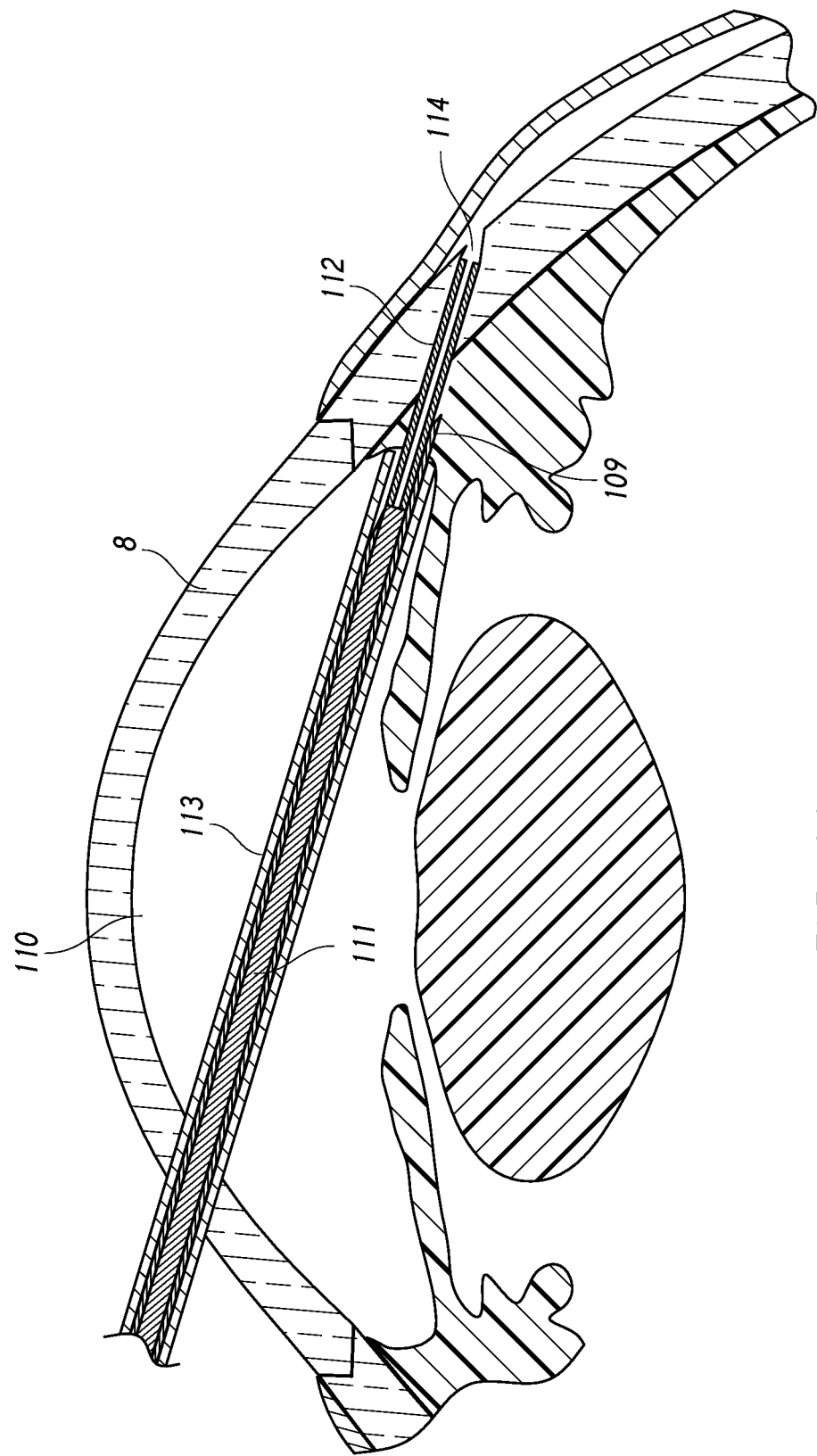
Figure 29:
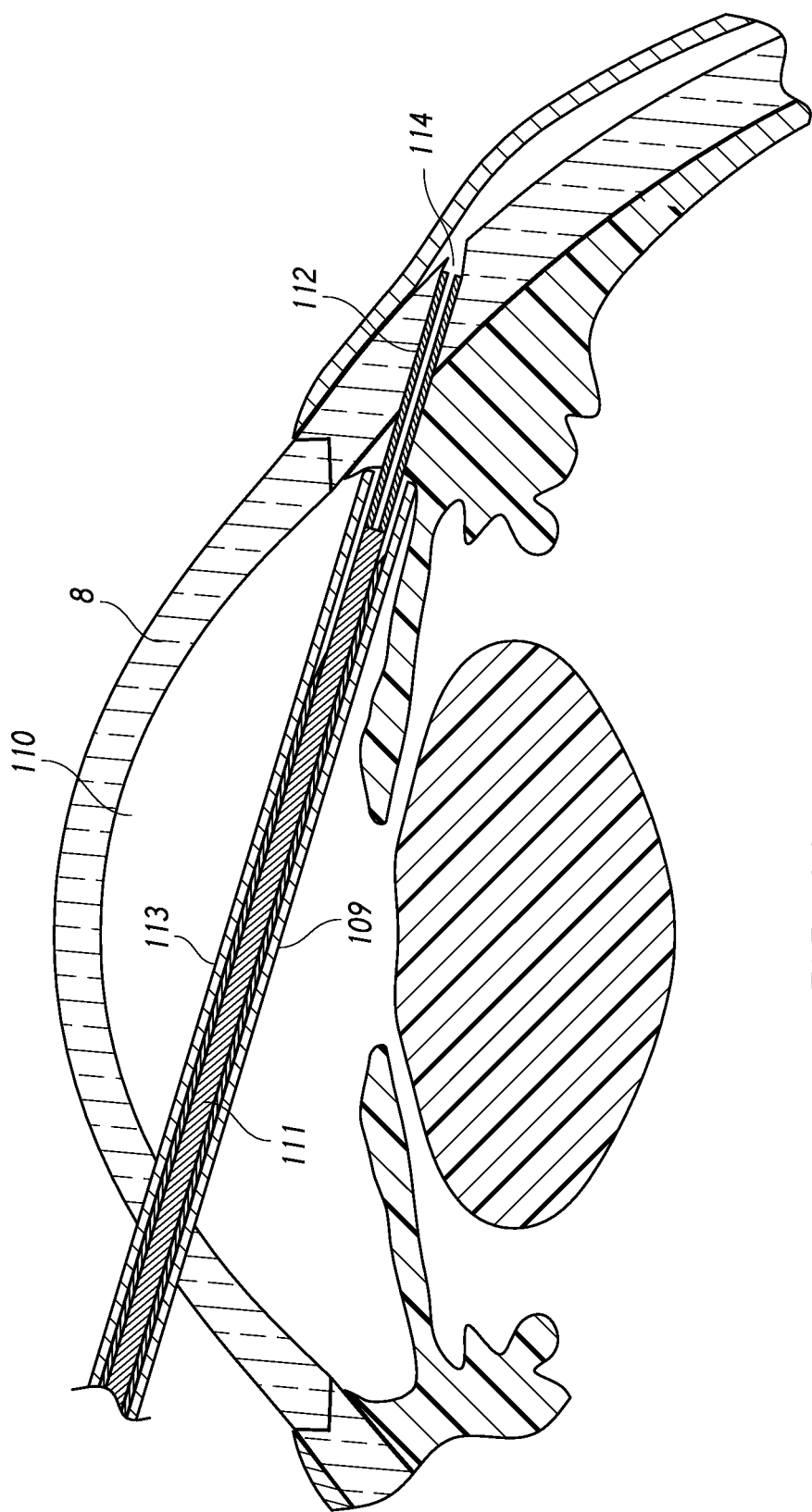
Figure 30:
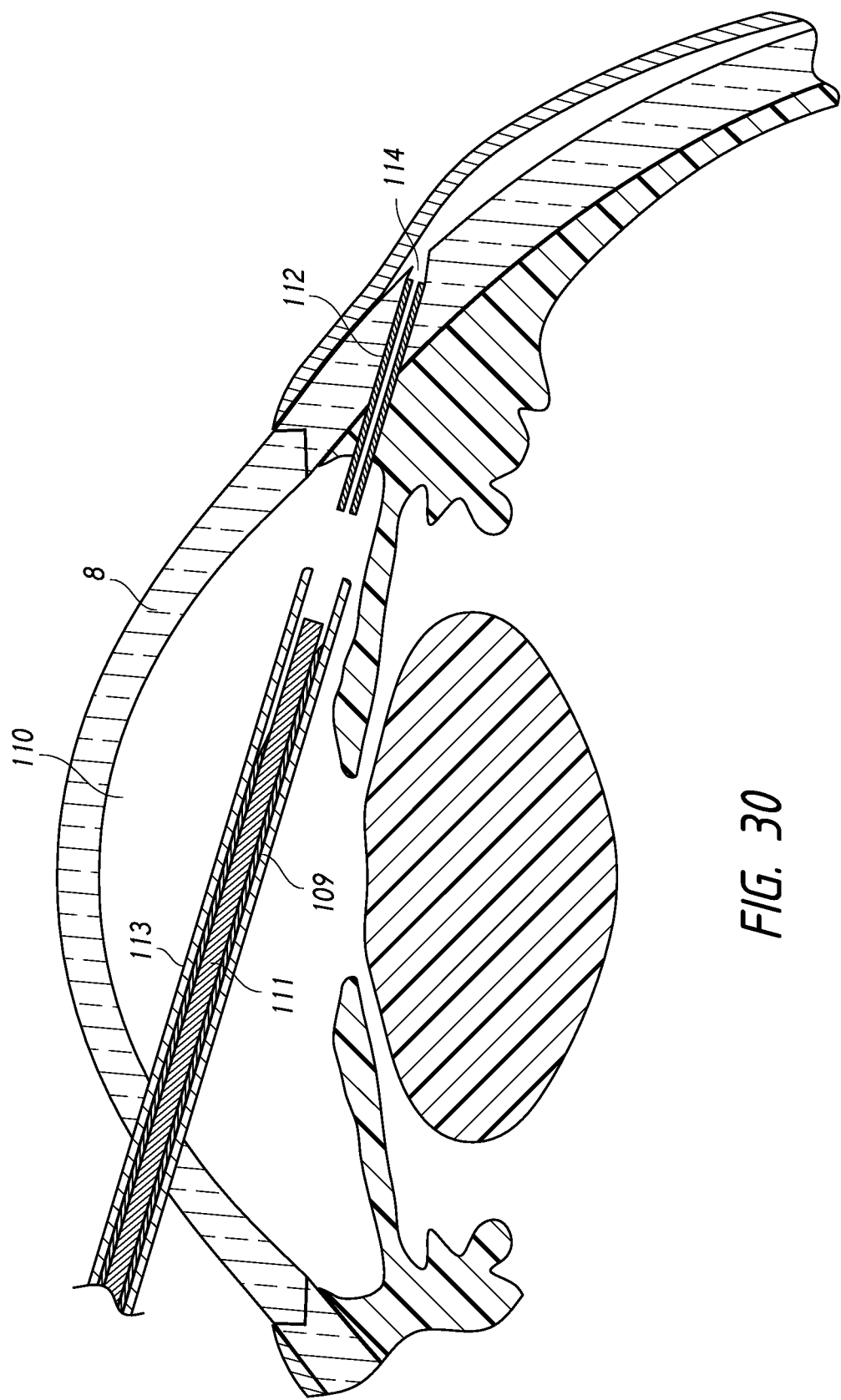

To place the shunt within the eye, a surgical intervention to implant the shunt is performed that involves inserting into the eye a deployment device that holds an intraocular shunt, and deploying at least a portion of the shunt within intrascleral space. FIGS. 23-30 provide an exemplary sequence for ab interno shunt placement. In certain embodiments, a hollow shaft 109 of a deployment device holding the shunt 112 enters the eye through the cornea (ab interno approach, FIG. 23). The shaft 109 is advanced across the anterior chamber 110 in what is referred to as a transpupil implant insertion. The shaft 109 is advanced through the anterior angle tissues of the eye and into the sclera 8 and further advanced until it passes through the sclera 8, thereby forming a second opening in the sclera 8 (FIGS. 24-25). Once the second opening in the sclera 8 is achieved, the shaft 109 is retracted all the way back through the sclera 8 and into the anterior chamber 110 of the eye (FIGS. 26-29). During this shaft retraction, the shunt 112 is held in place by a plunger rod 111 that is positioned behind the proximal end of the shunt 112. After the shaft 109 has been completely withdrawn from the sclera 8, the plunger rod 111 is withdrawn as well and the shunt implantation sequence is complete (FIG. 30). This process results in an implanted shunt 112 in which a distal end of the shunt 112 is proximate a passageway 114 through the sclera 8. Once fully deployed, a proximal end of shunt 112 resides in the anterior chamber 110 and a distal end of shunt 112 resides in the intrascleral space. Preferably a sleeve 113 is used around the shaft 112 and designed in length such that the sleeve 113 acts as a stopper for the scleral penetration of the shaft and also determines the longitudinal placement of the proximal end of the shunt.

Insertion of the shaft of the deployment device into the sclera 8 produces a long scleral channel of about 2 mm to about 5 mm in length. Withdrawal of the shaft of the deployment device prior to deployment of the shunt 112 from the device produces a space in which the shunt 112 may be deployed. Deployment of the shunt 112 allows for aqueous humor 3 to drain into traditional fluid drainage channels of the eye (e.g., the intrascleral vein, the collector channel, Schlemm's canal, the trabecular outflow, and the uveoscleral outflow to the ciliary muscle. The deployment is performed such that an outlet of the shunt is positioned proximate the opening in the sclera so that at least some of the fluid that exits the shunt flows through the opening in the sclera, thereby ensuring that the intrascleral space does not become overwhelmed with fluid output from the shunt.

Figure 4:
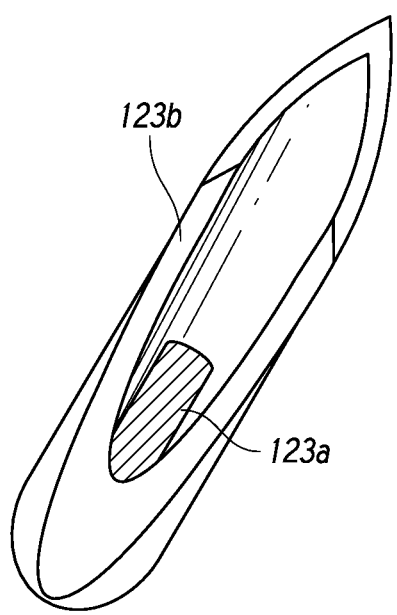
FIG. 4 depicts an intraocular shunt at least partially disposed within a hollow shaft of a deployment device, according to some embodiments.
Figure 32:
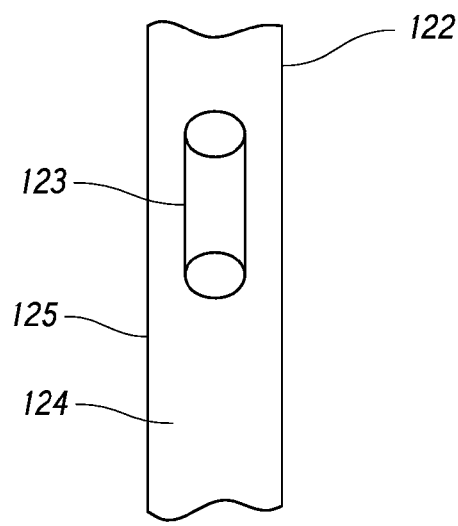
FIG. 32 depicts an example of a hollow shaft configured to hold an intraocular shunt fully within the shaft, according to some embodiments.

FIG. 32 provides an exemplary schematic of a hollow shaft for use in accordance with some embodiments of the methods disclosed herein. This figure shows a hollow shaft 122 that is configured to hold an intraocular shunt 123. The shaft may hold the shunt within the hollow interior 124 of the shaft, as is shown in FIG. 32. Alternatively, the hollow shaft may hold the shunt on an outer surface 125 of the shaft. In some embodiments, the shunt is held completely within the hollow interior of the shaft 124, as is shown in FIG. 32. In other embodiments, a shunt 123a is only partially disposed within a hollow shaft 123b, as shown in FIG. 4. Generally, in one embodiment, the intraocular shunts are of a cylindrical shape and have an outside cylindrical wall and a hollow interior. The shunt may have an inside diameter of about 10 μm to about 250 μm, an outside diameter of about 100 μm to about 450 μm, and a length of about 1 mm to about 12 mm. In some embodiments, the shunt has a length of about 2 mm to about 10 mm and an outside diameter of about 150 μm to about 400 μm. The hollow shaft 122 is configured to at least hold a shunt of such shape and such dimensions. However, the hollow shaft 122 may be configured to hold shunts of different shapes and different dimensions than those described above, and some embodiments can encompass a shaft 122 that may be configured to hold any shaped or dimensioned intraocular shunt.

Preferably, some embodiments of the methods disclosed herein are conducted by making an incision in the eye prior to insertion of the deployment device. In some embodiments of the methods disclosed herein may be conducted without making an incision in the eye prior to insertion of the deployment device. In certain embodiments, the shaft that is connected to the deployment device has a sharpened point or tip. In certain embodiments, the hollow shaft is a needle. Exemplary needles that may be used are commercially available from Terumo Medical Corp. (Elkington Md.). In some embodiments, the needle has a hollow interior and a beveled tip, and the intraocular shunt is held within the hollow interior of the needle. In another embodiment, the needle has a hollow interior and a triple ground point or tip.

Some embodiments of the methods disclosed herein are preferably conducted without needing to remove an anatomical portion or feature of the eye, including but not limited to the trabecular meshwork, the iris, the cornea, or aqueous humor. Some embodiments of the methods disclosed herein are also preferably conducted without inducing substantial ocular inflammation, such as subconjunctival blebbing or endophthalmitis. Such methods can be achieved using an ab interno approach by inserting the hollow shaft configured to hold the intraocular shunt through the cornea, across the anterior chamber, through the trabecular meshwork and into the sclera. However, some embodiments of the methods disclosed herein may be conducted using an ab externo approach.

When some embodiments of the methods disclosed herein are conducted using an ab interno approach, the angle of entry through the cornea as well as the up and downward forces applied to the shaft during the scleral penetration affect optimal placement of the shunt in the intrascleral space. Preferably, the hollow shaft is inserted into the eye at an angle superficial to the corneal limbus, in contrast with entering through or deep to the corneal limbus. For example, the hollow shaft is inserted about 0.25 mm to about 3.0 mm, preferably about 0.5 mm to about 2.5 mm, more preferably about 1.0 mm to about 2.0 mm superficial to the corneal limbus, or any specific value within said ranges, e.g., about 1.0 mm, about 1.1 mm, about 1.2 mm, about 1.3 mm, about 1.4 mm, about 1.5 mm, about 1.6 mm, about 1.7 mm, about 1.8 mm, about 1.9 mm, or about 2.0 mm superficial to the corneal limbus.

Figure 31:
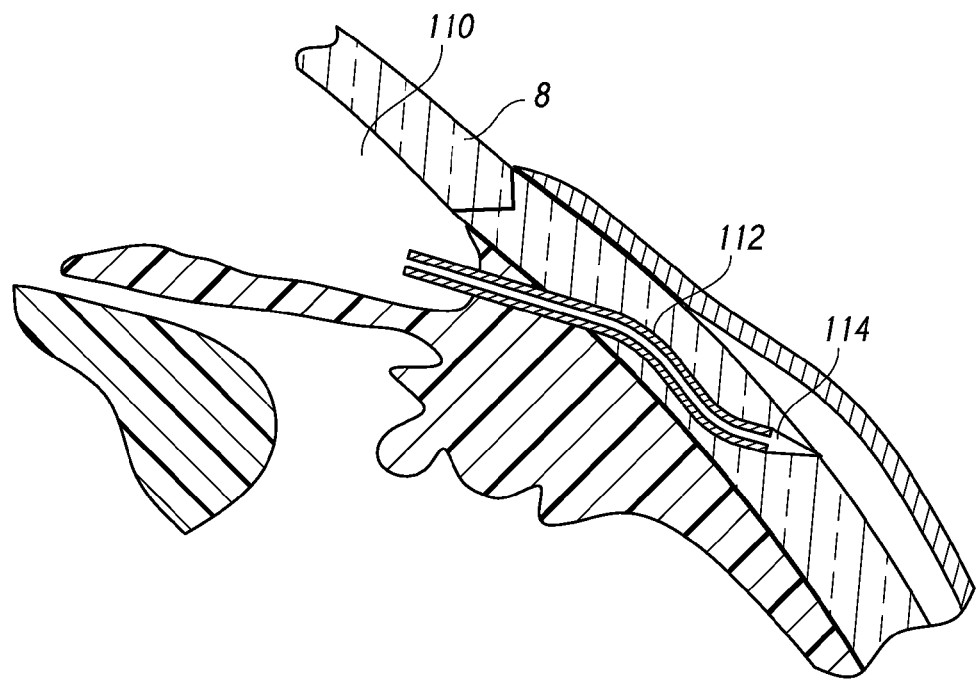
FIG. 31 depicts an implanted shunt in an S-shaped scleral passageway, according to some embodiments.

Without intending to be bound by any theory, placement of the shunt farther from the limbus at the exit site, as provided by an angle of entry superficial to the limbus, as well as an S-shaped scleral tunnel (FIG. 31) due to applied up or downward pressure during the scleral penetration of the shaft is believed to provide access to more lymphatic channels for drainage of aqueous humor, such as the episcleral lymphatic network, in addition to the conjunctival lymphatic system.

Ab Externo Approach

In other embodiments, an ab externo approach is employed. Ab externo implantation approaches are shown for example in Nissan et al. (U.S. Pat. No. 8,109,896), Tu et al. (U.S. Pat. No. 8,075,511), and Haffner et al. (U.S. Pat. No. 7,879,001), the content of each of which is incorporated by reference herein in its entirety. An exemplary ab externo approach avoids having to make a scleral flap. In this preferred embodiment, a distal end of the deployment device is used to make an opening into the eye and into the sclera. For example, a needle is inserted from ab externo through the sclera and exits the anterior angle of the eye. The needle is then withdrawn, leaving a scleral slit behind. A silicone tube with sufficient stiffness is then manually pushed through the scleral slit from the outside so that the distal tube ends distal to the Trabecular Meshwork in the anterior chamber of the eye. Towards the proximal end, the tube exits the sclera, lays on top of it, and connects on its proximal end to a plate that is fixated by sutures to the outside scleral surface far away (>10 mm) from the limbus.

Figure 33:
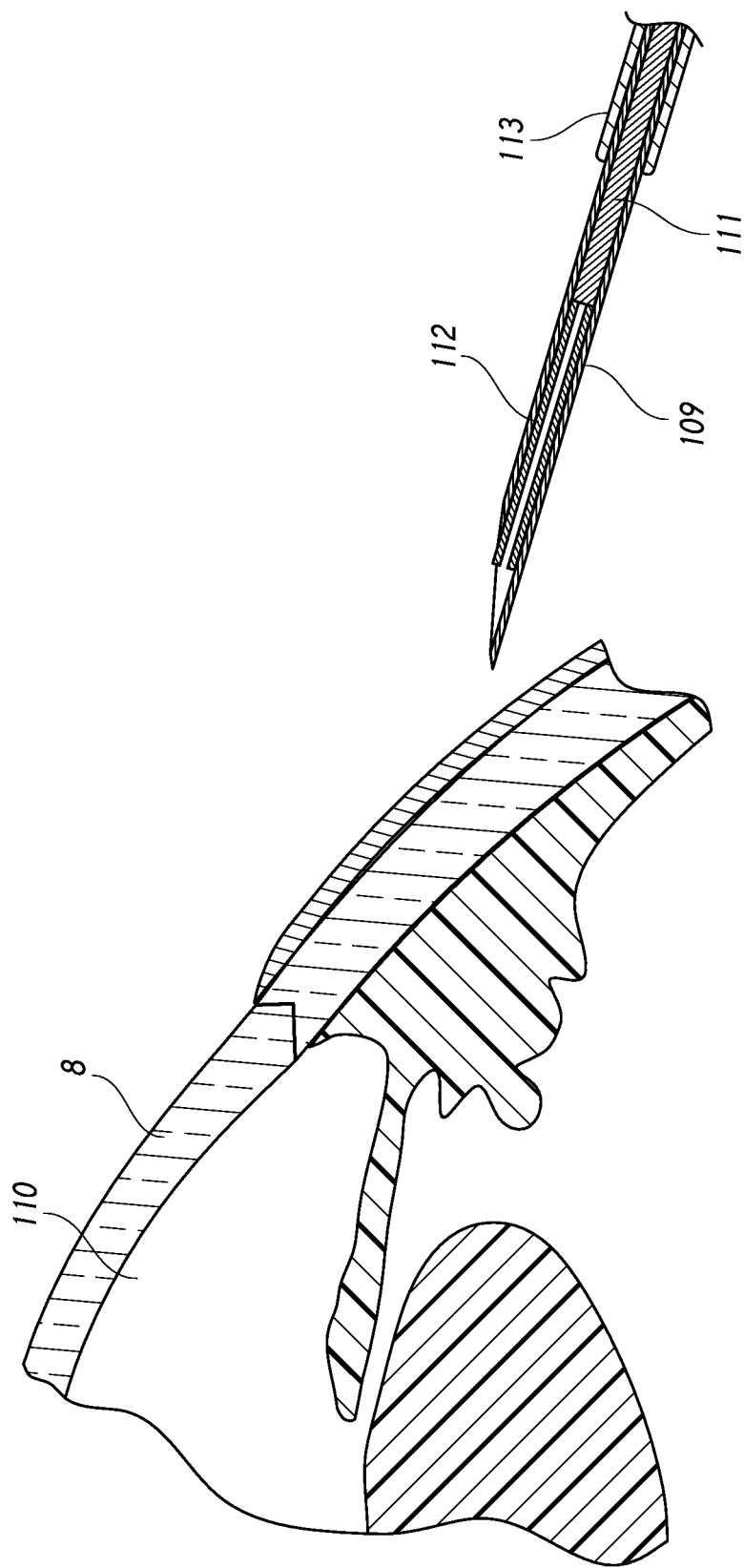
FIGS. 33-39 depict a sequence for ab externo shunt placement, according to some embodiments.
Figure 34:
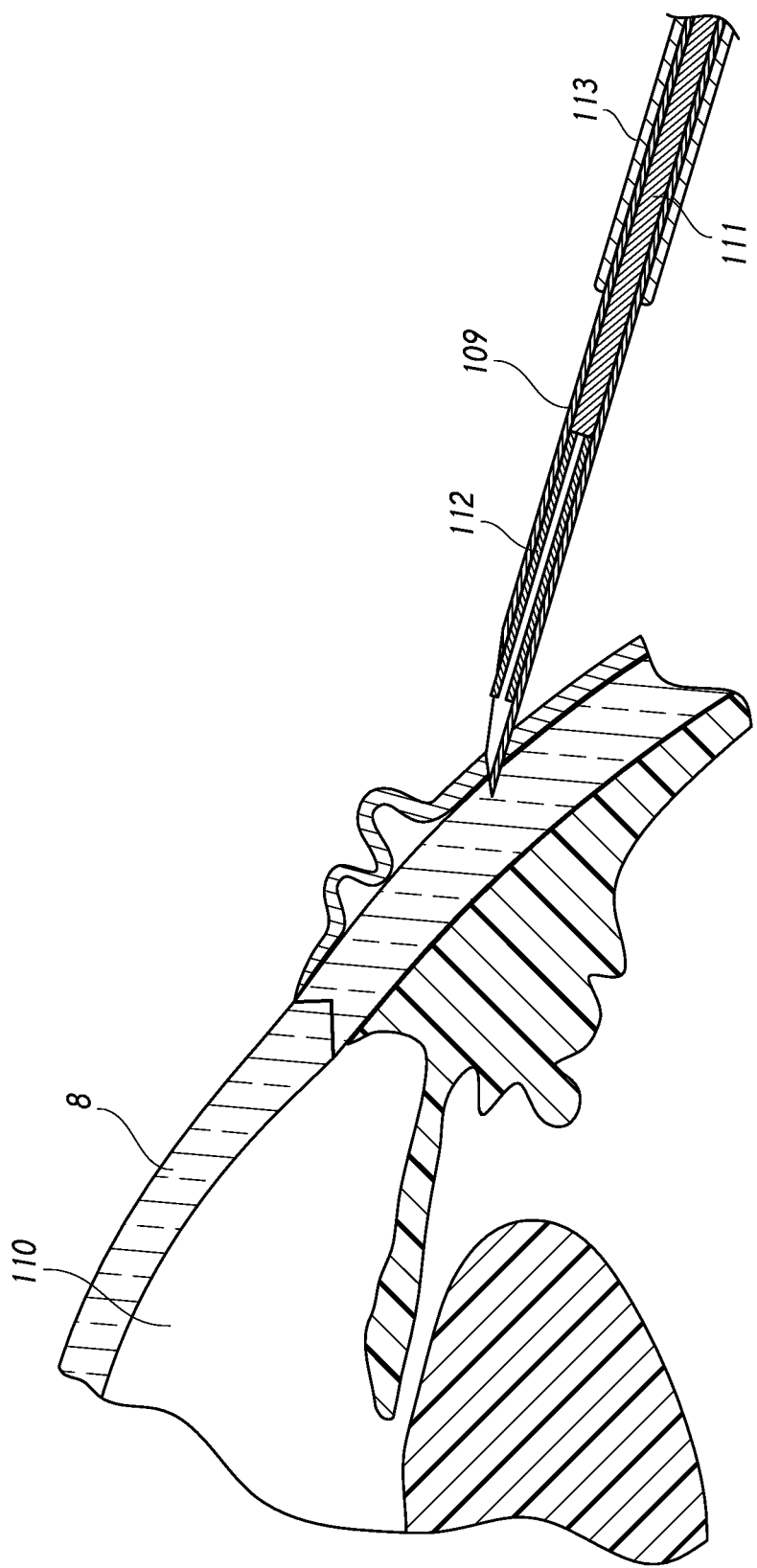
Figure 35:
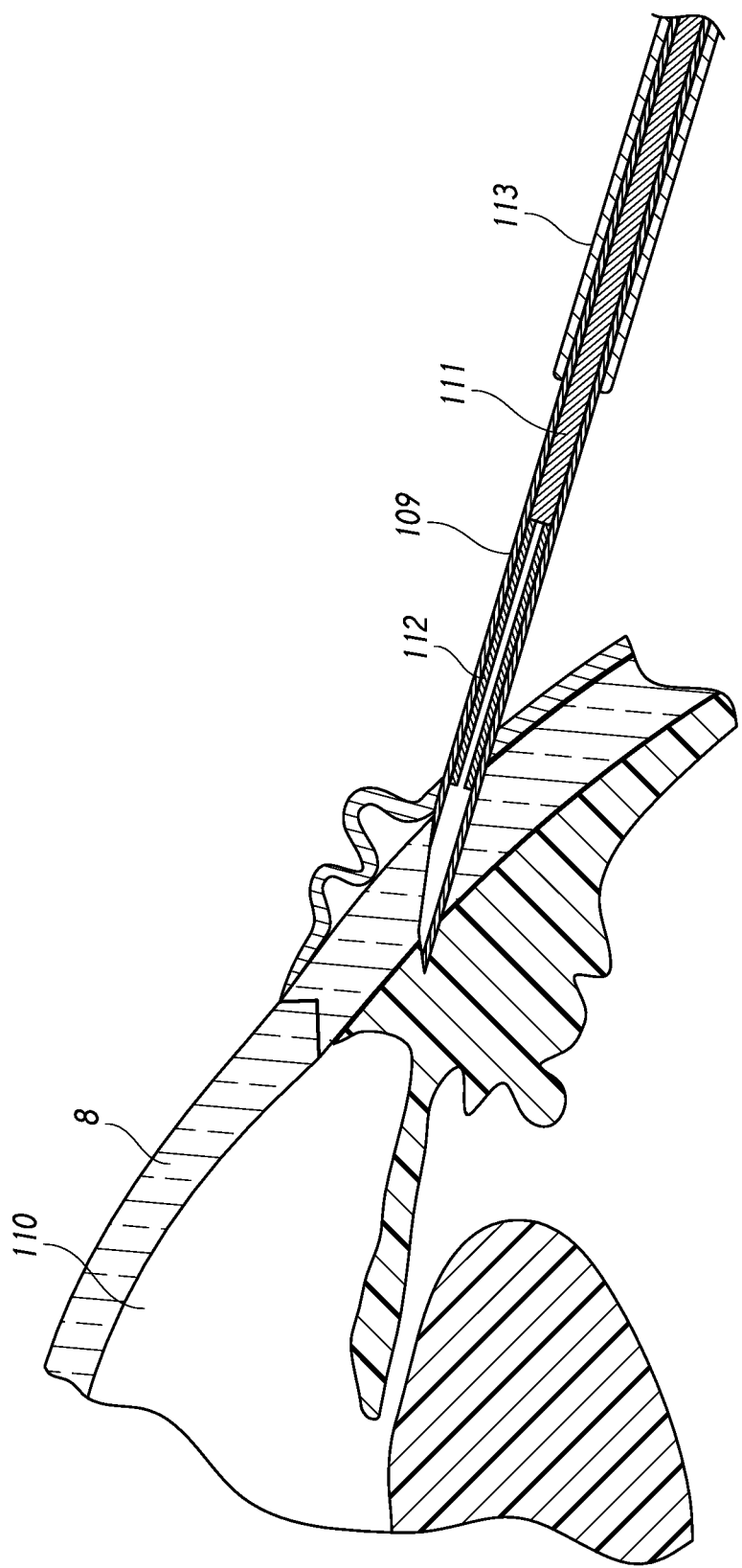
Figure 36:
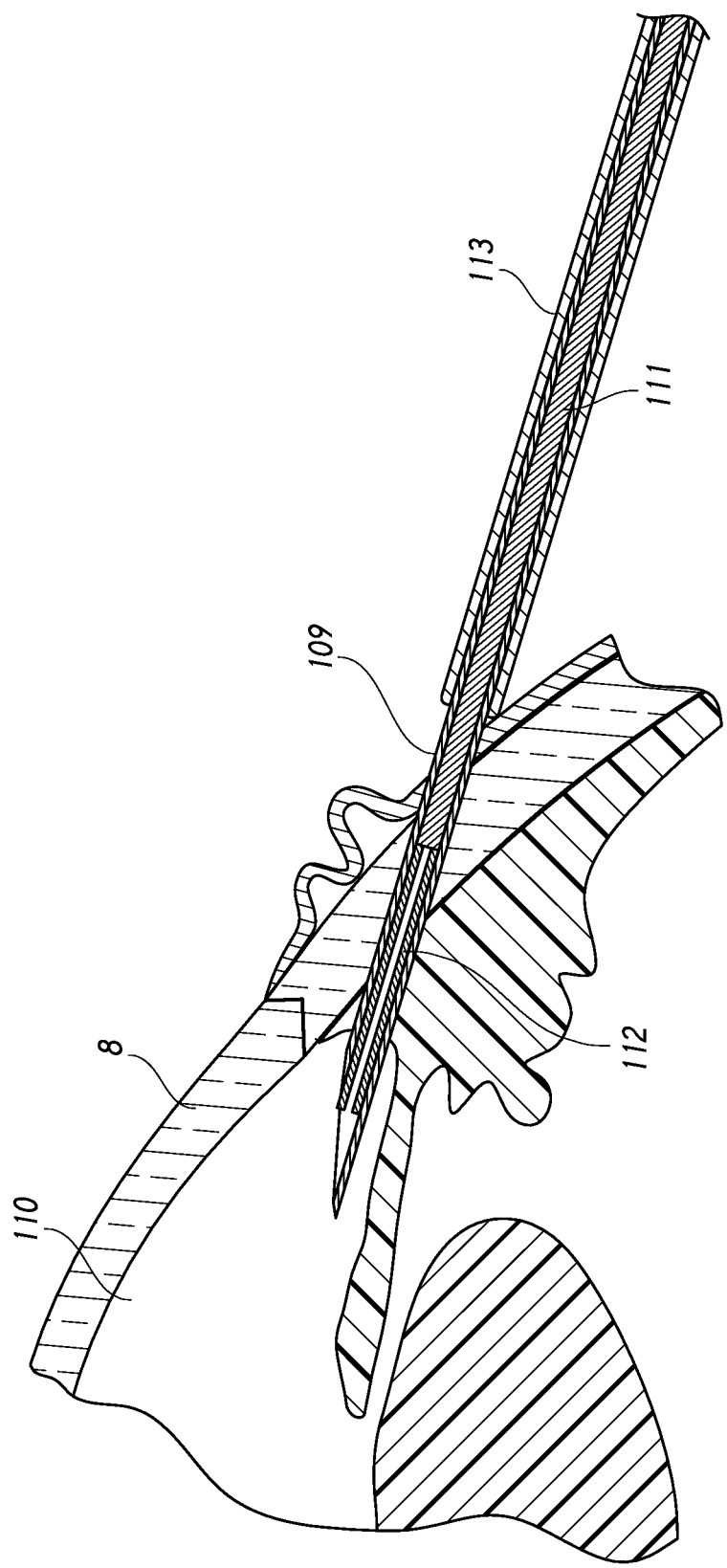
Figure 37:
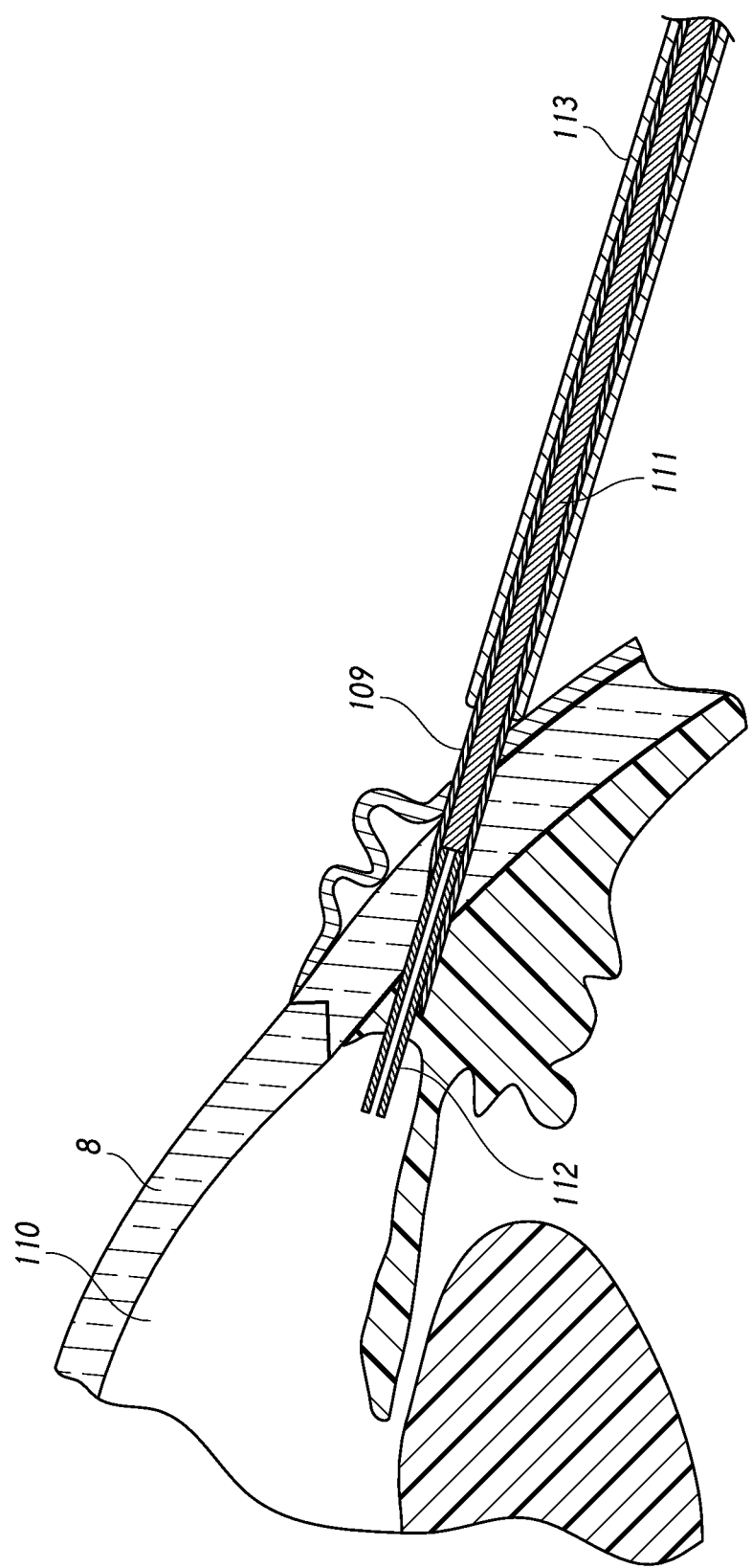
Figure 38:
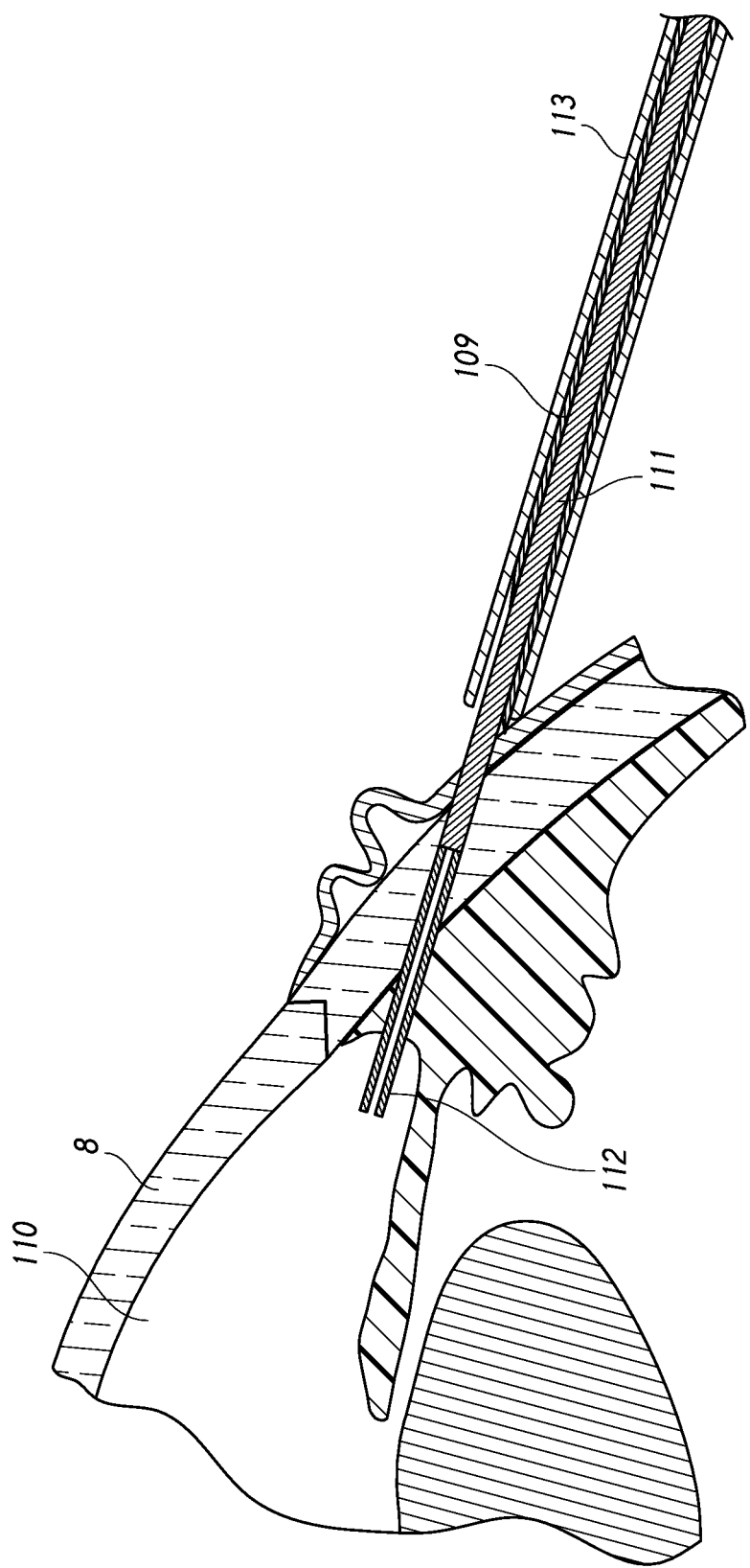
Figure 39:
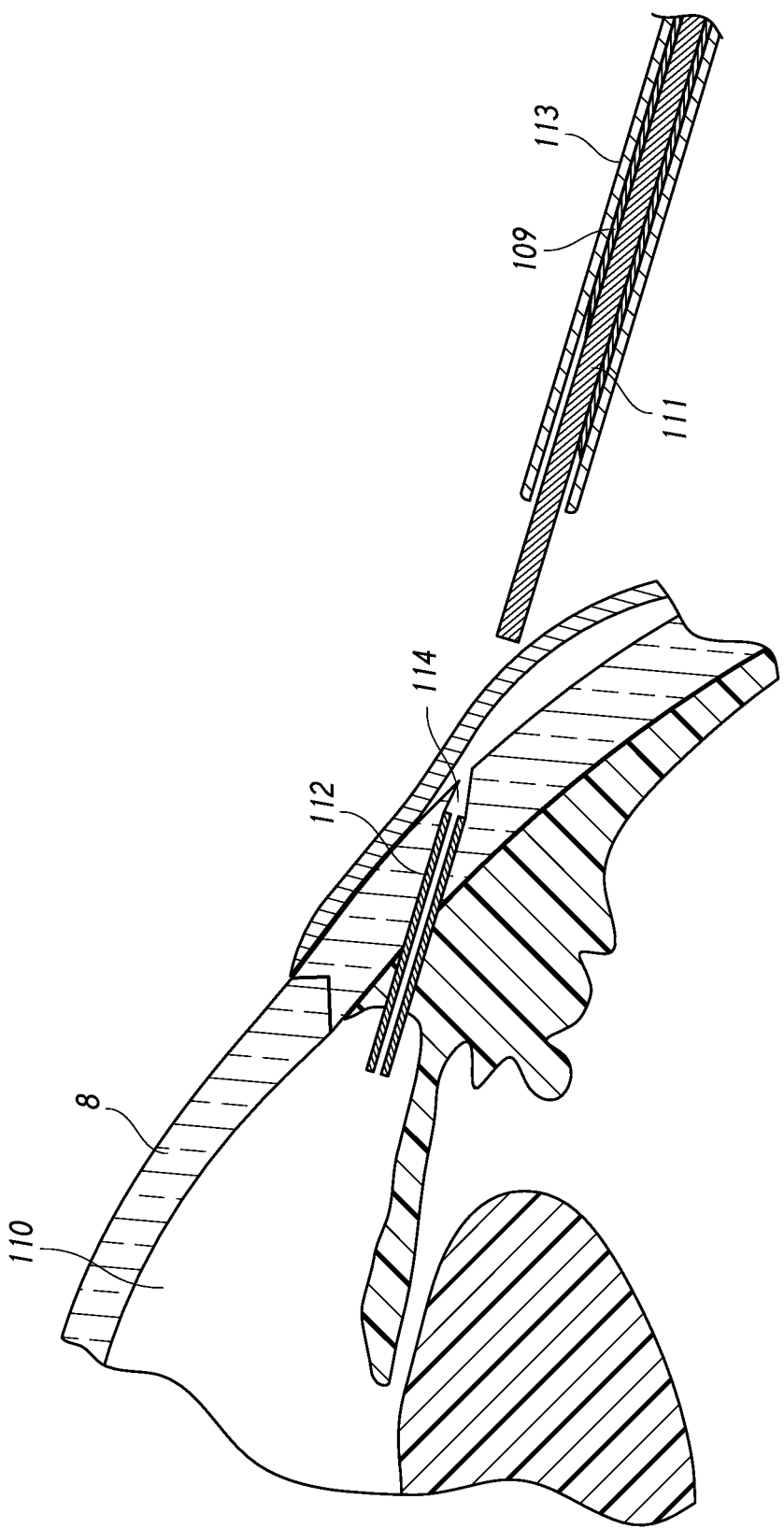

FIGS. 33-39 describes another ab externo method that uses a deployment device. In this method, a distal portion of the deployment device includes a hollow shaft 109 that has a sharpened tip (FIG. 33). A shunt 112 resides within the shaft 109. The distal shaft 109 is advanced into the eye and into the sclera 8 until a proximal portion of the shaft resides in the anterior chamber 110 and a distal portion of the shaft 109 is inside the scleral 8 (FIGS. 34-36). Deployment of the shunt 112 that is located inside the shaft 109 is then accomplished by a mechanism that withdraws the shaft 109 while the shunt 112 is held in place by a plunger 111 behind the proximal end of the shunt 112 (FIGS. 37-39). As the implantation sequence progresses, the shaft 109 is completely withdrawn from the sclera 8. After that, the plunger 111 is withdrawn from the sclera 8, leaving the shunt 112 behind with its distal end inside the sclera 8, its proximal end inside the anterior chamber 110, and a passageway 114 through the sclera 8. In a preferred embodiment the shaft 109 is placed inside a sleeve 113 that is dimensioned in length relative to the shaft 109 such that it will act as stopper during the penetration of the shaft 109 into the eye and at the same time assures controlled longitudinal placement of the shunt 112 relative to the outer surface of the eye. The sleeve 113 may be beveled to match the anatomical angle of the entry site surface.

The shaft penetrates the conjunctival layer before it enters and penetrates the sclera. This causes a conjunctival hole that could create a fluid leakage after the shunt placement has been completed. To minimize the chance for any leakage, a small diameter shaft is used that results in a self-sealing conjunctival wound. To further reduce the chance for a conjunctival leak, a suture can be placed in the conjunctiva around the penetration area after the shunt placement.

Figure 40:
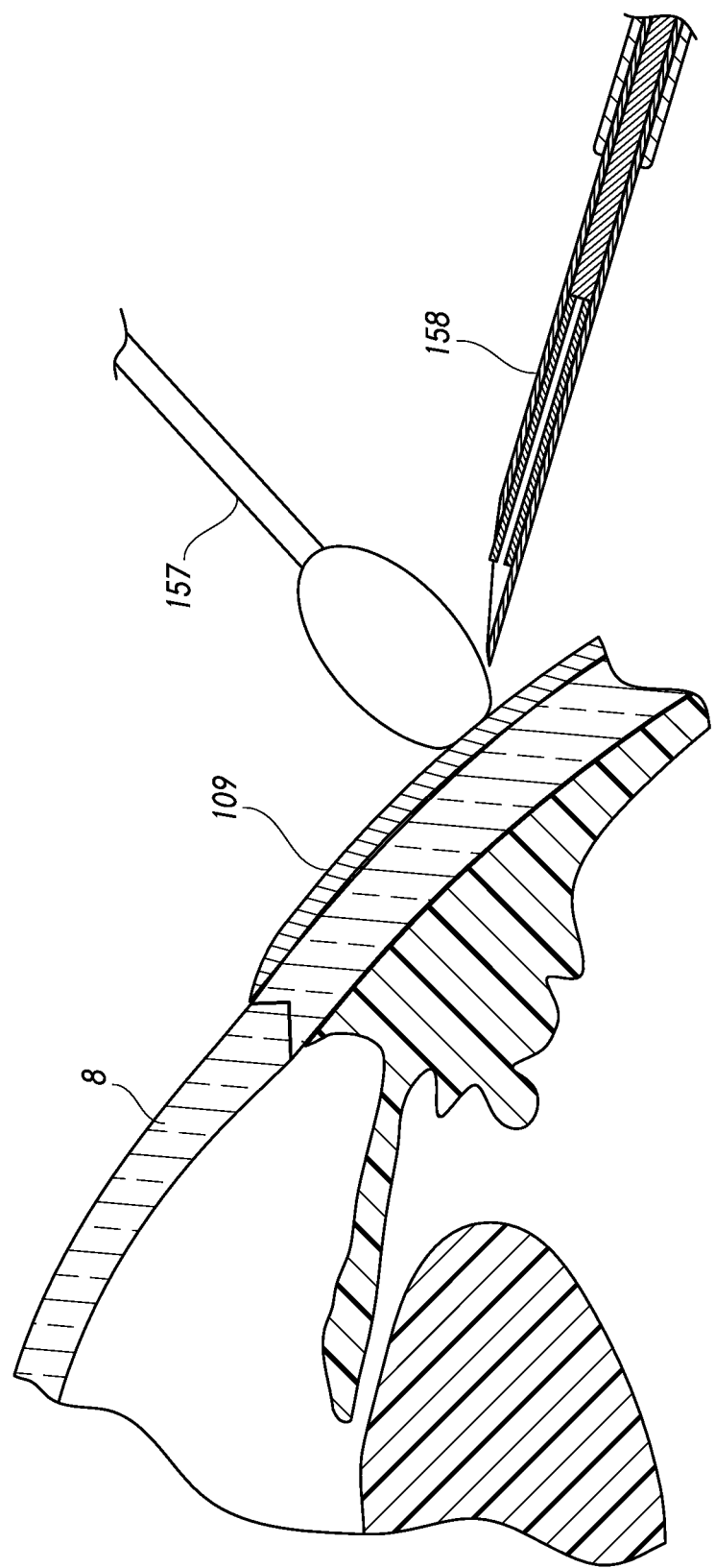
FIGS. 40-41 depict a sequence for ab externo insertion of a shaft of a deployment device using an applicator, according to some embodiments.
Figure 41:
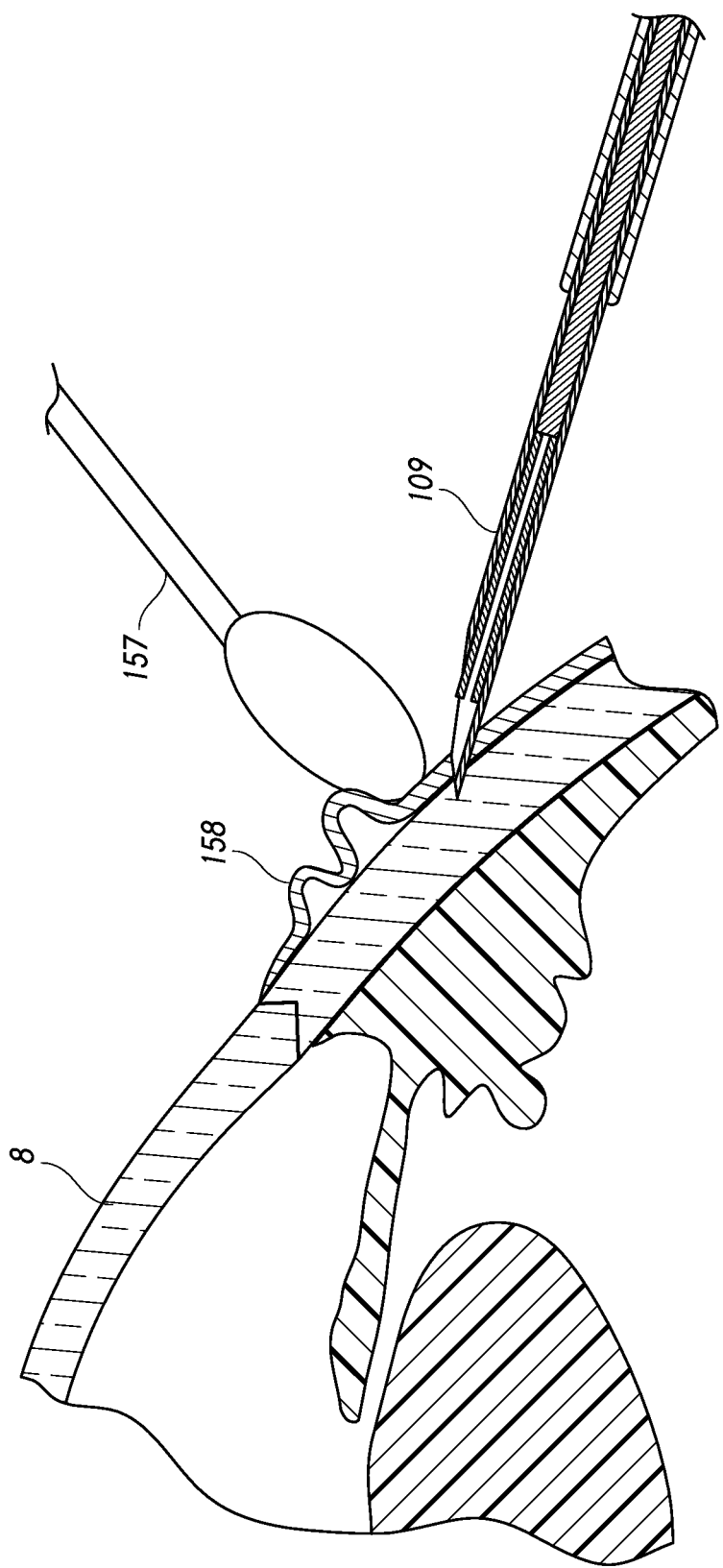

Furthermore the preferred method of penetrating the conjunctiva is performed by shifting the conjunctival layers from posterior to the limbus towards the limbus, using e.g. an applicator such as a Q-tip, before the shaft penetration is started. This is illustrated in FIGS. 40-41. That figure shows that an applicator 157 is put onto the conjunctiva 158, about 6 mm away from the limbus. The loose conjunctiva layer is then pushed towards the limbus to create folding tissue layers that are about 2 mm away from the limbus. The device shaft 109 is now inserted through the conjunctiva and sclera 8 starting about 4 mm away from the limbus. After the shunt placement has been completed, the Q-tip is released and the conjunctival perforation relaxes back from about 4 mm to about 8 mm limb at distance. This can cause the conjunctival perforation to be 4 mm away from the now slowly starting drainage exit. This distance will reduce any potential for leakage and allows for a faster conjunctival healing response. Alternative to this described upward shift, a sideway shift of the conjunctiva or anything in between is feasible as well. In another embodiment of the ab externo method, a conjunctival slit is cut and the conjunctiva is pulled away from the shaft entry point into the sclera. After the shunt placement is completed, the conjunctival slit is closed again through sutures.

In certain embodiments, since the tissue surrounding the trabecular meshwork is optically opaque, an imaging technique, such as ultrasound biomicroscopy (UBM), optical coherence tomography (OCT) or a laser imaging technique, can be utilized. The imaging can provide guidance for the insertion of the deployment device and the deployment of the shunt. This technique can be used with a large variety of shunt embodiments with slight modifications since the trabecular meshwork is punctured from the scleral side, rather than the anterior chamber side, in the ab externo insertion.

In another ab externo approach, a superficial flap may be made in the sclera and then a second deep scleral flap may be created and excised leaving a scleral reservoir under the first flap. Alternatively, a single scleral flap may be made with or without excising any portion of the sclera.

A shaft of a deployment device is inserted under the flap and advanced through the sclera and into an anterior chamber. The shaft is advanced into the sclera until a proximal portion of the shaft resides in the anterior chamber and a distal portion of the shaft is in proximity to the trabecular outflow. The deployment is then performed such that an outlet of the shunt is positioned proximate the second opening in the sclera so that at least some of the fluid that exits the shunt flows through the first opening in the sclera, thereby ensuring that the intrascleral space does not become overwhelmed with fluid output from the shunt. At the conclusion of the ab externo implantation procedure, the scleral flap may be sutured closed. The procedure also may be performed without suturing.

Figure 42:
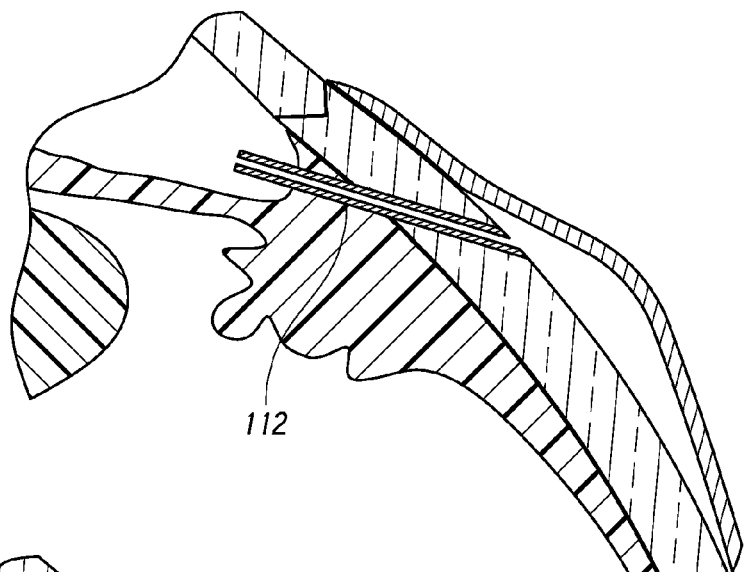
FIG. 42 depicts deployment of the shunt in the intra scleral space where a distal end of the shunt is flush with the sclera surface, according to some embodiments.
Figure 43:
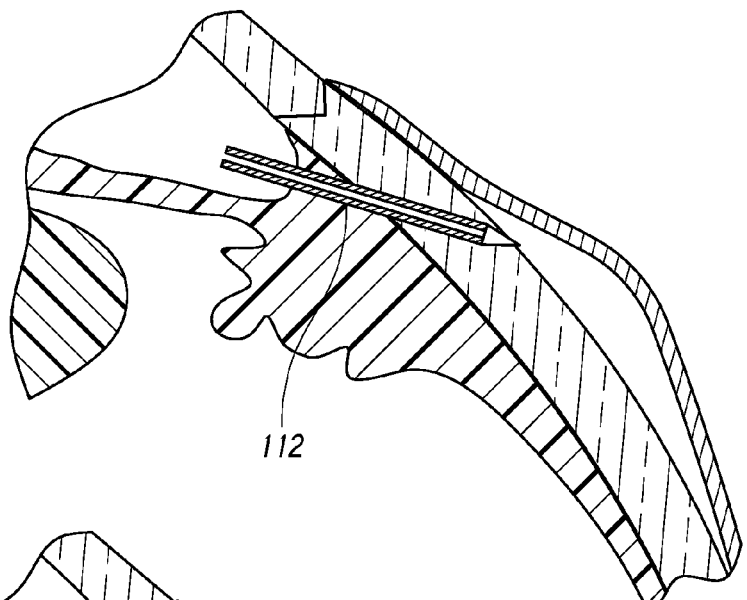
FIG. 43 depicts deployment of the shunt in the intra scleral space where a distal end of the shunt is about 200-500 micron behind the scleral exit, according to some embodiments.
Figure 44:
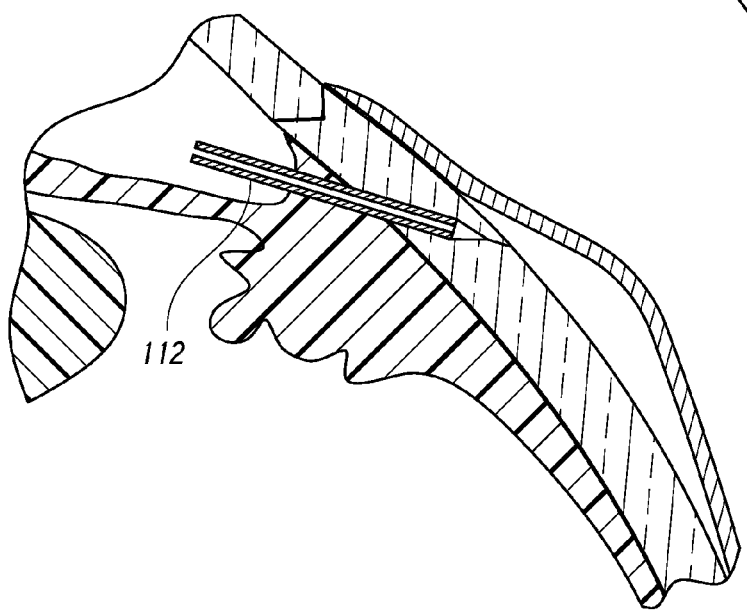
FIG. 44 depicts deployment of the shunt in the intra scleral space where a distal end of the shunt is more than about 500 micron behind the scleral exit, according to some embodiments.

Regardless of the implantation method employed, some embodiments of the methods disclosed herein recognize that the proximity of the distal end of the shunt to the scleral exit slit affects the flow resistance through the shunt, and therefore affects the intraocular pressure in the eye. For example, if the distal end of the shunt 112 is flush with the sclera surface then there is no scleral channel resistance (FIG. 42). In this embodiment, total resistance comes from the shunt 112 alone. In another embodiment, if the distal end of the shunt 112 is about 200 μm to about 500 μm behind the scleral exit, then the scleral slit closes partially around the exit location, adding some resistance to the outflow of aqueous humor (FIG. 43). In another embodiments, if the distal end of the shunt 112 is more than about 500 micron behind the scleral exit, than the scleral slit closes completely around the exit location with no backpressure and opens gradually to allow aqueous humor to seep out when the intraocular pressure raises e.g. above 10 mmHg (FIG. 44). The constant seepage of aqueous humor keeps the scleral slit from scaring closed over time.

Effectively, shunt placement according to some embodiments of the methods disclosed herein achieve a valve like performance where the scleral slit in front of the distal shunt end acts like a valve. The opening (cracking) pressure of this valve can be adjusted by the outer shunt diameter and its exact distal end location relative to the scleral exit site. Typical ranges of adjustment are 1 mmHg to 20 mmHg. This passageway distance can be controlled and adjusted through the design of the inserting device as well as the shunt length and the deployment method. Therefore a specific design can be chosen to reduce or prevent hypotony (<6 mmHg) as a post-operative complication.

FIGS. 45-51 illustrates placement of a shunt in various locations of the eye, according to some embodiments. In these figures, the first end of a shunt is positioned in the region of lower pressure and a second end of the shunt is positioned in a region of high pressure. For example, in FIG. 45, an end of a shunt 300 is shown extending into the anterior chamber 1.

According to some embodiments of the methods disclosed herein, the shunt can access the region of lower pressure by extending through the anterior chamber angle tissue. Thus, whether the shunt is targeting supraciliary space, suprachoroidal space, the intrascleral space, intra-Tenon's adhesion space, or subconjunctival space, the shunt can be placed through the anterior chamber angle tissue.

Figure 45:
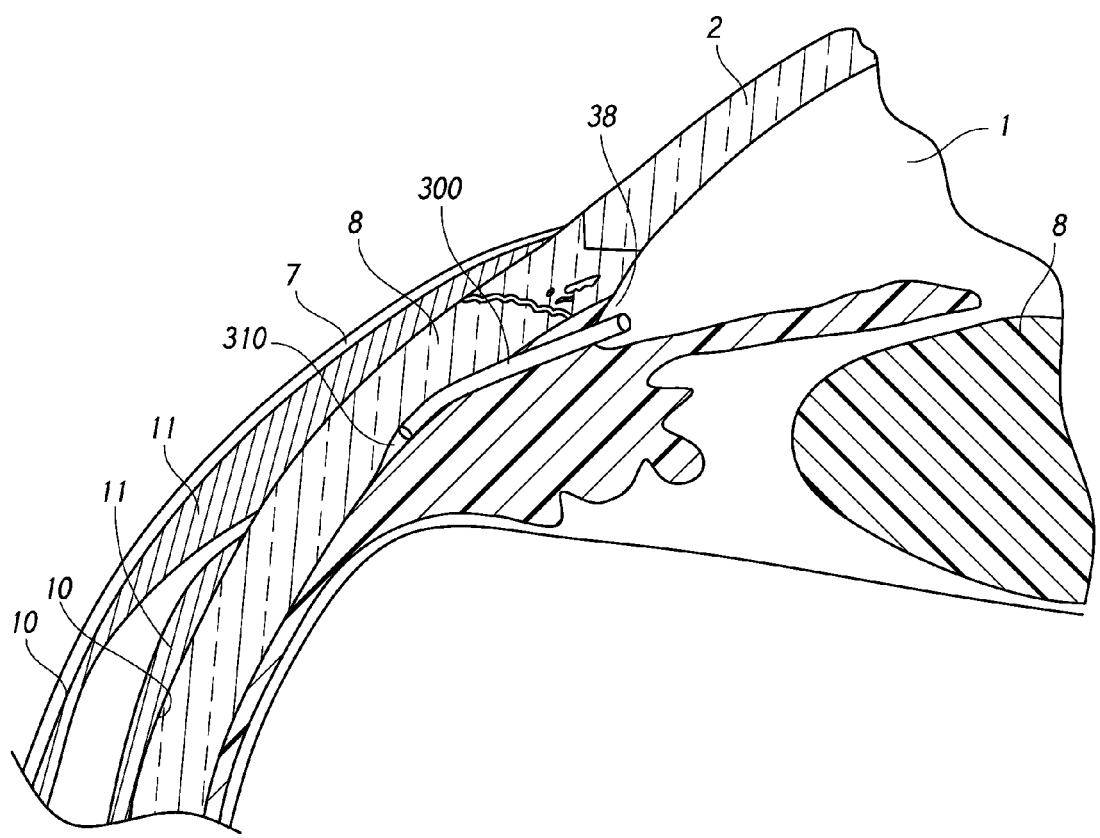
FIG. 45 depicts placement of a shunt in the supraciliary space, according to some embodiments.
Figure 46:
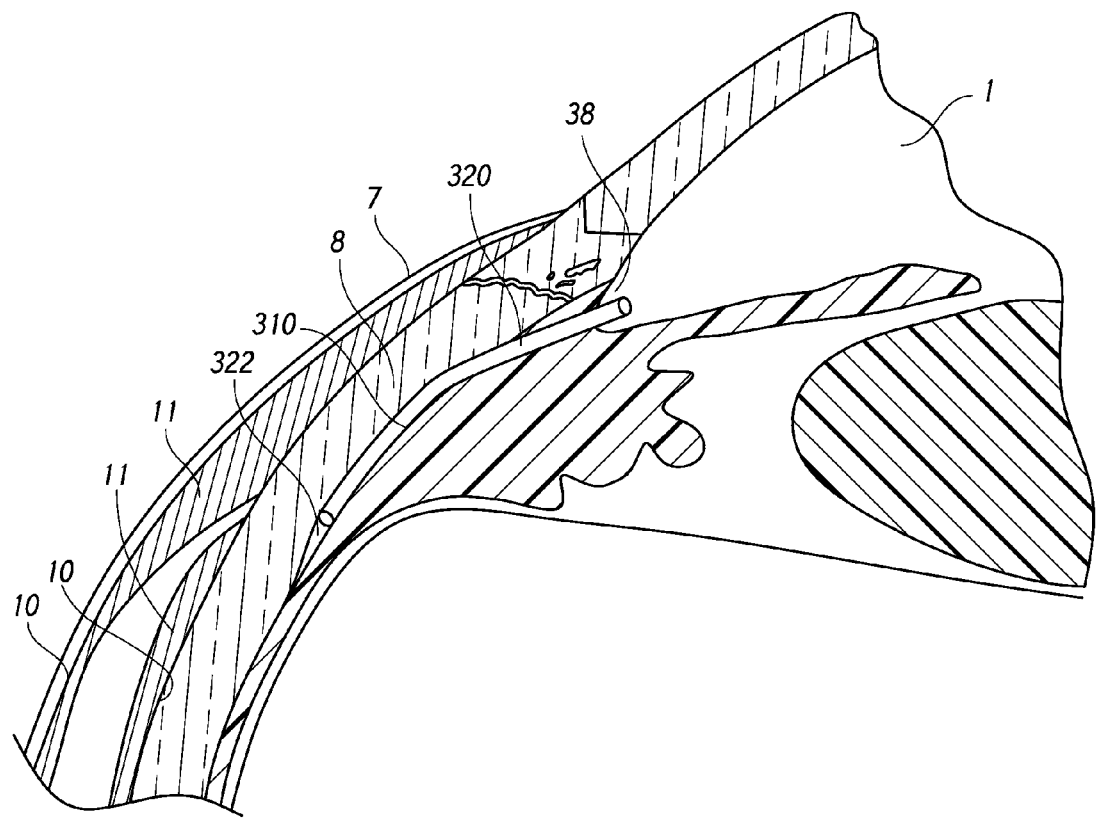
FIG. 46 depicts placement of a shunt in the suprachoroidal space, according to some embodiments.

FIG. 45 illustrates supraciliary placement of a shunt 300. As shown, the shunt 300 extends from the anterior chamber 1 to the supraciliary space 310. FIG. 46 illustrates suprachoroidal placement of a shunt 320. As shown, the shunt 320 extends from the anterior chamber 1 to a suprachoroidal space 322. As discussed above, the supraciliary space 310 can be continuous with the suprachoroidal space 322.

Figure 47:
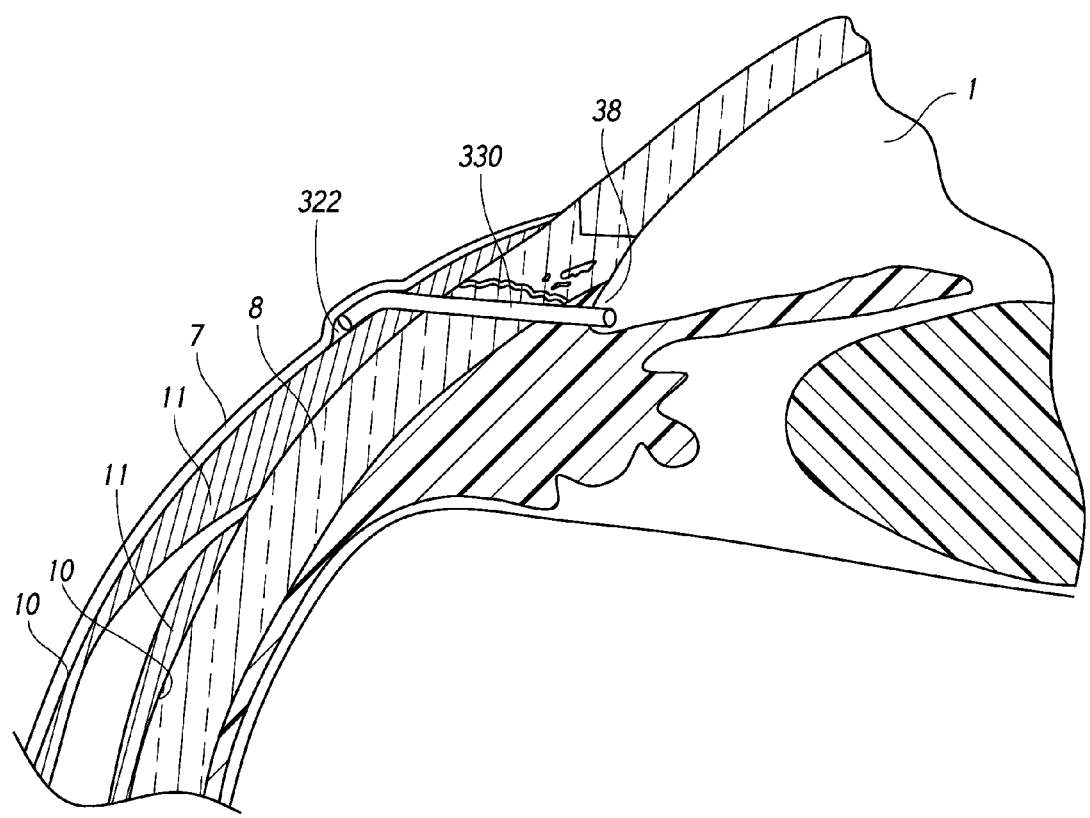
FIG. 47 depicts placement of a shunt in the subconjunctival space, according to some embodiments.
Figure 48:
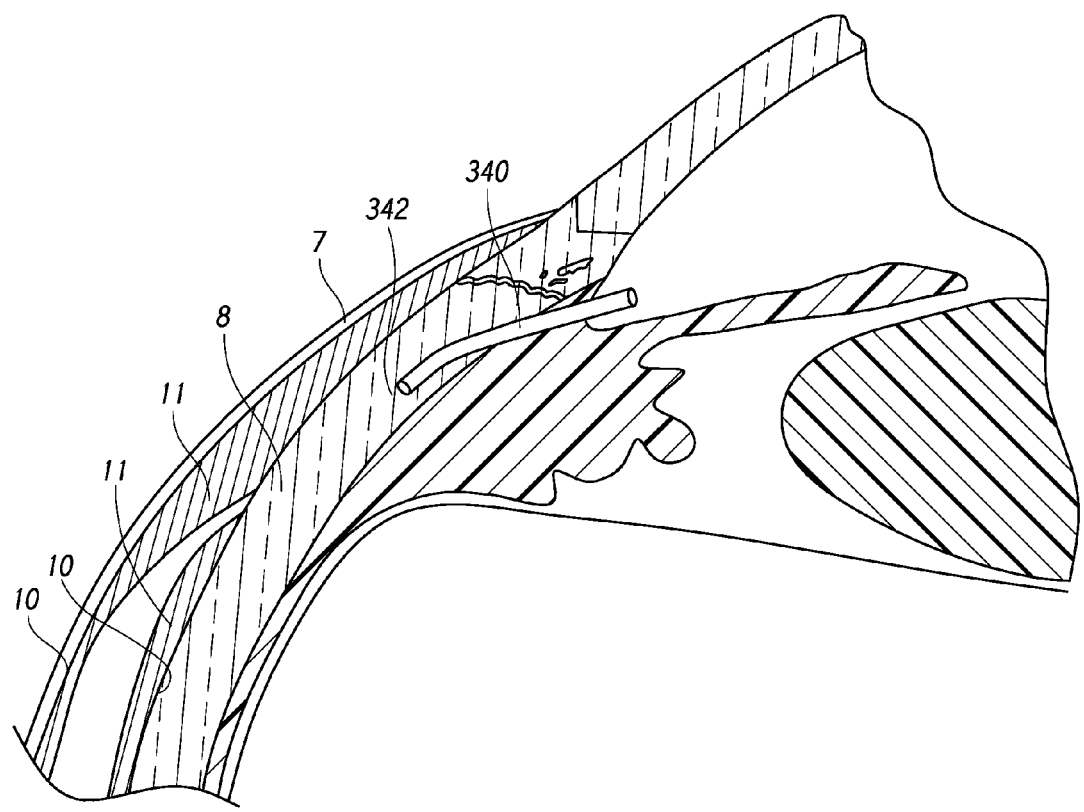
FIG. 48 depicts placement of a shunt in the intrascleral space, according to some embodiments.

FIG. 47 illustrates subconjunctival placement of a shunt 330. As shown, the shunt 330 extends from the anterior chamber 1 to the subconjunctival space 332. FIG. 48 illustrates intrascleral placement of a shunt 340. As shown, the shunt 340 extends from the anterior chamber 1 to the intrascleral space 342.

Figure 49:
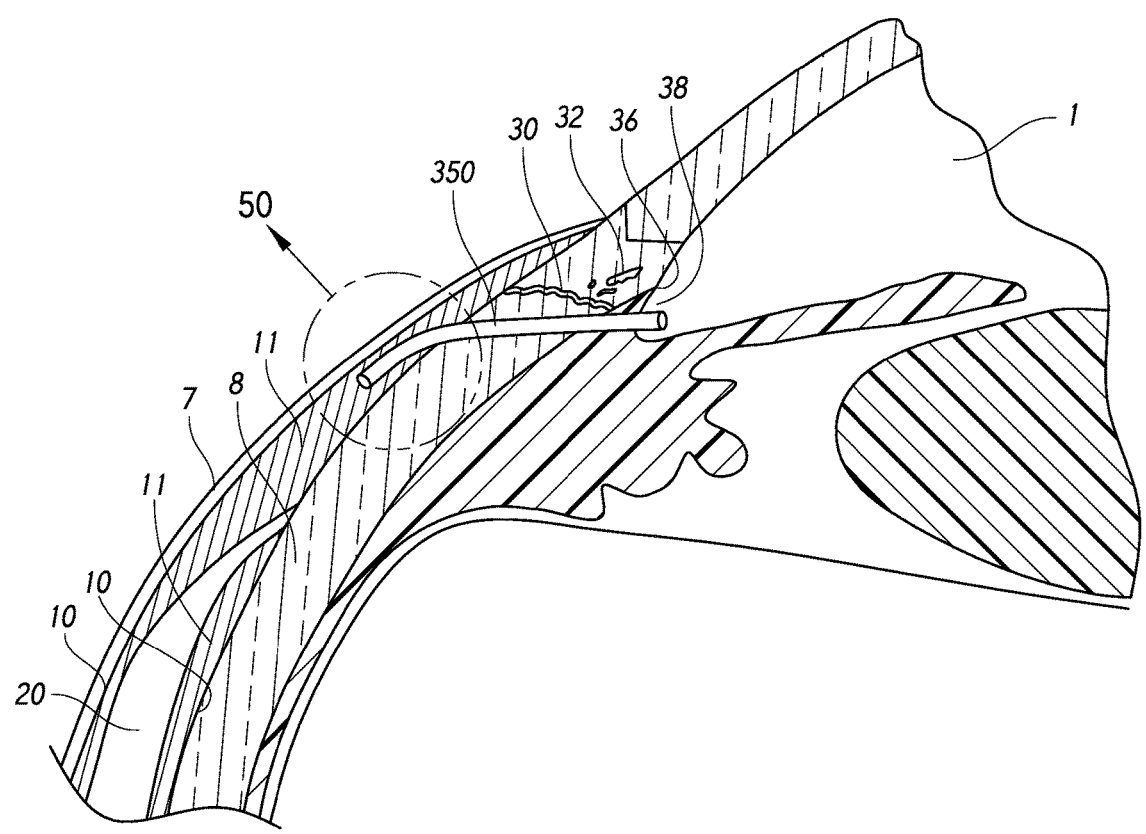
FIG. 49 depicts placement of a shunt in the intra-Tenon's adhesion space, according to some embodiments.

FIG. 49 depicts placement of a shunt 350 in the intra-Tenon's adhesion space 11 of Tenon's capsule 10, according to some embodiments. As shown, the shunt 350 extends from the anterior chamber 1 to the intra-Tenon's adhesion space 11. The shunt 350 can be passed through the sclera 8. In some embodiments, the shunt 350 can extend at least partially through Schlemm's canal 30 and/or the trabecular meshwork 32. Further, the shunt 350 can extend through the trabecular meshwork 32 without passing through Schlemm's canal 30. Furthermore, the shunt 350 can extend entirely through the sclera 8 without passing through Schlemm's canal 30 or the trabecular meshwork 32. This may be accomplished by passing through the sclera in a location posterior to Schlemm's canal 34 anterior to the trabecular meshwork 32, above the scleral spur 36. In accordance with some embodiments, the shunt 350 can access the intra-Tenon's adhesion space 11 in a location anterior to the rectus muscle 20. For example, a distal end of the shunt 350 can be positioned between the layers of intra-Tenon's adhesion space 11 anterior to the rectus muscle 20.

Figure 50:
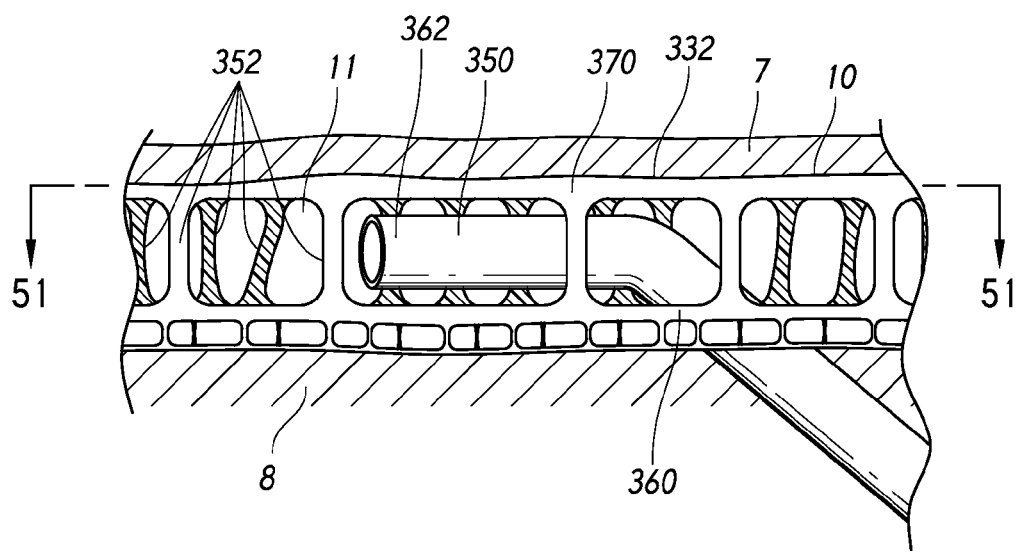
FIG. 50 is an enlarged schematic cross-sectional view taken along section 50 of FIG. 49.

FIG. 50 is an enlarged schematic cross-sectional view taken along section lines 50-50 of FIG. 49. As illustrated in FIG. 50, the shunt 350 extends through the intra-Tenon's adhesion space 11. As shown, the intra-Tenon's adhesion space 11 comprises spongy, porous tissue (adhesions 352) that can facilitate drainage of aqueous humor from the anterior chamber.

When placing the shunt 350 into the intra-Tenon's adhesion space 11, some embodiments of the methods disclosed herein can comprise accessing the intra-Tenon's adhesion space 11 by inserting a needle through a deep layer 360 of Tenon's capsule 10 and positioning a distal end 362 of the shunt 350 into the intra-Tenon's adhesion space 11.

For example, the shunt 350 can enter intra-Tenon's adhesion space 11 and, while maintaining the position of the needle (to avoid further advancement of the needle into the intra-Tenon's adhesion space 11), the shunt 350 can then be urged distally into the intra-Tenon's adhesion space 11 in order to preserve the adhesions 352 that extend between a superficial layer 370 and the deep layer 360 of the Tenon's capsule 10.

Figure 51:
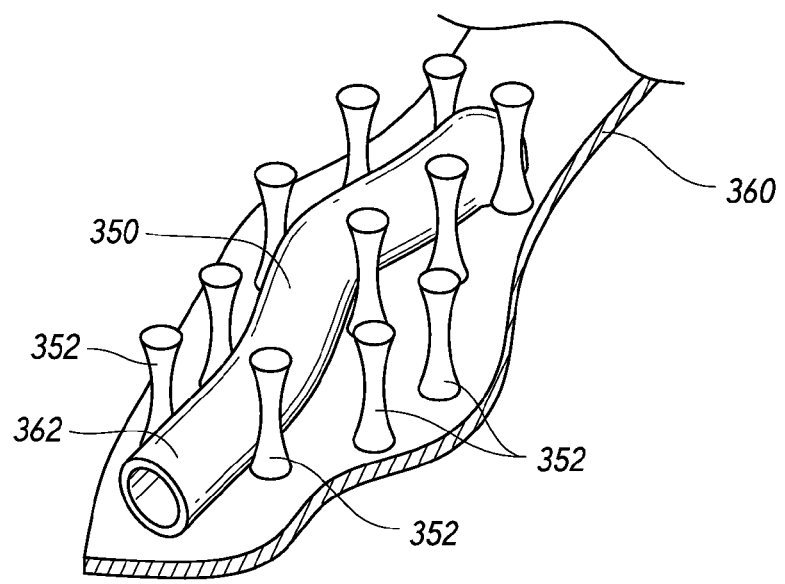
FIG. 51 is a perspective view taken along section lines 51-51 of FIG. 50.

In some embodiments, when the deep layer 360 is pierced, the shunt 350 can be at least partially exposed beyond a distal tip of a needle and urged distally using a pusher component such that the shunt moves distally out of the needle while maintaining the needle in a generally stationary position. For example, FIG. 51 illustrates that the distal end 362 of the shunt 350 can be urged distally such that the distal end 362 passes between adjacent adhesions 352, which may cause the shunt 350 to deflect, bend, and/or curve within the intra-Tenon's adhesion space 11. Embodiments of such methods can thus be performed to allow non-destructive access to the intra-Tenon's adhesion space 11.

Deployment Device Motion Sequences

According to some embodiments, the deployment device can be operated to release a shunt within the eye using a variety of motion sequences. The motion sequences can be performed manually or automatically, with a device. In some embodiments of the sequences discussed below, the operator or clinician can perform a procedure using only two discrete motions: advancing the device into the eye until reaching a final stop position and then, after the shunt has been implanted into the tissue, retracting the device from the eye. However, in accordance with some embodiments of the sequences discussed below, the operator or clinician can also exert a rotational force on one or more components of the device or on the device as a whole, to control advancement and release of the shunt. Further, in some embodiments of the sequences discussed below, the operator or clinician can perform the procedure using more than two discrete axial motions, such as: advancing the device into the eye until reaching a preliminary stop position, and while implanting the shunt into the tissue, advancing the device toward a final stop position; thereafter, when the shunt is implanted into the tissue, the device can be proximally withdrawn from the tissue. Additionally, in some embodiments of the sequences discussed below, the operator or clinician can exert axial and rotational forces on the device to facilitate placement and release of the shunt.

Various procedures for releasing a shunt into the eye are discussed below with respect to FIGS. 52A-54E and aspects of this discussion can be applied to more than one of the embodiments of the procedures discussed herein. Such procedures allow a clinician to use a deployment device to place the shunt precisely within the eye while minimizing any trauma to the surrounding eye tissue.

As shown, FIGS. 52A-52E illustrate placement of a shunt into the subconjunctival space. However, as discussed herein, the desired location can be one of various anatomical locations within the eye, including, but not limited to the intrascleral space, the subconjunctival space, and/or the intra-Tenon's adhesion space. According to some embodiments, the shunt can be positioned such that one or more drainage outlets of the shunt extends within one or more anatomical locations within the eye, such as a single anatomical location, or across multiple anatomical locations, thereby providing drainage to either a single or multiple locations.

Further, according to some embodiments, the deployment device can comprise a shaft that has a hard tip (e.g., to pierce the sclera for placing the shunt, e.g., in the intrascleral space, the subconjunctival space, and/or the intra-Tenon's adhesion space) or a softer tip (e.g., to advance the shunt, e.g., for placing the shunt in the supracilliary space and/or suprachoroidal space). Thus, although the embodiments illustrated in FIGS. 52A-55E illustrate that placement of a shunt can be through or in sclera, other embodiments of an implantation procedure can be performed such that the shunt is placed deep to a deep layer of the sclera.

According to some embodiments, a shunt can be loaded into the shaft such that a distal end portion of the shunt is positioned at the distal end of the shaft 410 (see e.g., FIGS. 23-30 and FIGS. 33-41).

FIGS. 52A-52E illustrate steps of a method in which a deployment device 400 can be inserted into the eye 402 and provide a visual indication or guide for an operator during shunt placement. The device 400 can be advanced across the anterior chamber 404 of the eye 402 until a needle or shaft 410 of the device 400 pierces the tissue at the anterior chamber angle 412, referred to as anterior chamber angle tissue. The device 400 can also comprise a sleeve 414 having a lumen in which the shaft 410 is disposed. The sleeve 414 can comprise a distal end 416 that can be visible within the anterior chamber 404 of the eye 402. According to some embodiments, a mark or reference point on the sleeve 414, for example, the distal end 416 of the sleeve 414, can provide a visual indication or guide for an operator during placement of the shunt, so as to locate or assess a final longitudinal position of the shunt.

For example, in some embodiments, such as those illustrated in FIGS. 52A-52E and 54A-54E, the deployment device 400 can be configured such that when the shunt is being released from the device 400, a pusher component or plunger of the device 400 can distally advance the shunt relative to the shaft 410 until the proximal end of the shunt is approximately longitudinally adjacent to the distal end 416 of the sleeve 414. Thus, after the pusher component has been advanced to a desired position (e.g., to a position in which a distal end of the pusher component is proximal to, coextensive with, or distal to a distal end of the shaft 410) within the shaft 410, proximal retraction of the shaft 410 (while maintaining the sleeve 414 in a desired location) will release the shunt from the device 400 with the proximal end of the shunt being finally positioned about where the distal end 416 of the sleeve 414 is positioned. While the relative positions of the distal end 416 of the sleeve 414 and the fully extended pusher component can vary according to some embodiments (e.g., contrast the embodiment shown in FIGS. 53A-53E), the visualization of the position of the distal end 416 (or another marked aspect of the sleeve 414) can facilitate precise longitudinal placement of the shunt within the eye tissue.

According to some embodiments, the mark or reference point of the sleeve 414 can comprise the distal end 416 or a line extending crosswise on the sleeve 414 (proximal to the distal end 416). The mark or reference point can comprise a high contrast element or color to facilitate visualization or discernment of the location of the marker reference point when the sleeve 414 is inserted into or toward an aspect of the eye, such as the anterior chamber 404 or anterior chamber angle 412.

Further, although a clinician can, in some embodiments, verify initial placement of the device 400 with reference only to a mark, reference point, or position of the distal end 416 of the sleeve 414 relative to an aspect of the eye, such as the anterior chamber angle tissue or anterior chamber angle 412 itself, the initial placement or position of the device 400 can also be based on the position of the shaft 410 within the eye tissue. For example, for subconjunctival placement of the shunt 420, as the shaft 410 is advanced through the sclera, a bevel 418 of the shaft 410 will eventually be seen through the conjunctiva (which is translucent) as the bevel 418 exits the sclera. The clinician, based on the visual confirmation of the location of the bevel below 418 the conjunctiva, can thereby determine that the shaft 410 has been advanced sufficiently. To avoid further advancement, which could result in piercing or damaging the conjunctiva, the clinician can use the distal end 416 of the sleeve 414 to provide a visual indication or guide whereby the clinician can maintain the position of the device 400 steady within the eye. Thus, the bevel 418 can be maintained in a position adjacent to or opening to the subconjunctival space.

In some embodiments, such as that illustrated in FIGS. 52A-52E, as the device 400 is moved through the anterior chamber 404 and into initial position within the eye tissue, the shaft 410 can be positioned relative to the sleeve 414 such that the bevel 418 is spaced about 3 mm to about 7 mm, about 4 mm to about 6 mm, or about 5 mm from the distal end 416 of the sleeve 414. Such spacing can allow the distal end 416 of the sleeve 414 to be spaced apart from the anterior chamber angle tissue when the bevel 418 emerges from the sclera to become visible under the conjunctiva. Thus, the clinician can advantageously confirm proper initial placement of the device 400 by verifying bevel emergence from the sclera if it would otherwise be difficult to visually verify a relative positioning of the distal end 416 of the sleeve 414 and the anterior chamber angle tissue or anterior chamber angle 412. This provides freedom to allow for variability in the anatomy and/or trajectory of the advancing shaft 410 (e.g., for differences in the thickness of sclera from patient to patient).

After the device 400 has been advanced through the anterior chamber 404 and the needle or shaft 410 has pierced the anterior chamber angle tissue at the anterior chamber angle 412, the shunt 420 can be advanced such that a distal end portion 422 of the shunt 420 is moved into or positioned at a desired location within the eye 402 (here shown as the subconjunctival space 430).

Figure 52A:
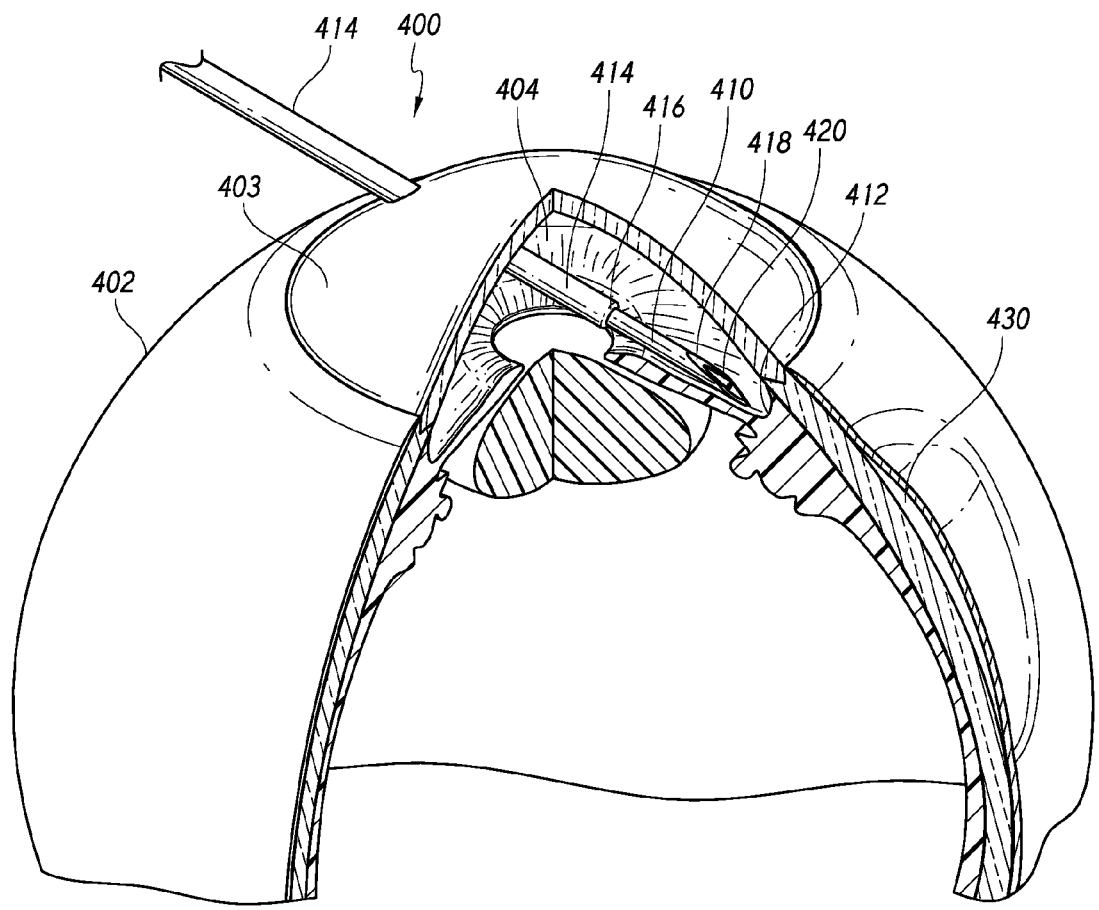
FIGS. 52A-52E depict an intraocular shunt being deployed within the eye, according to another embodiment.
Figure 52B:
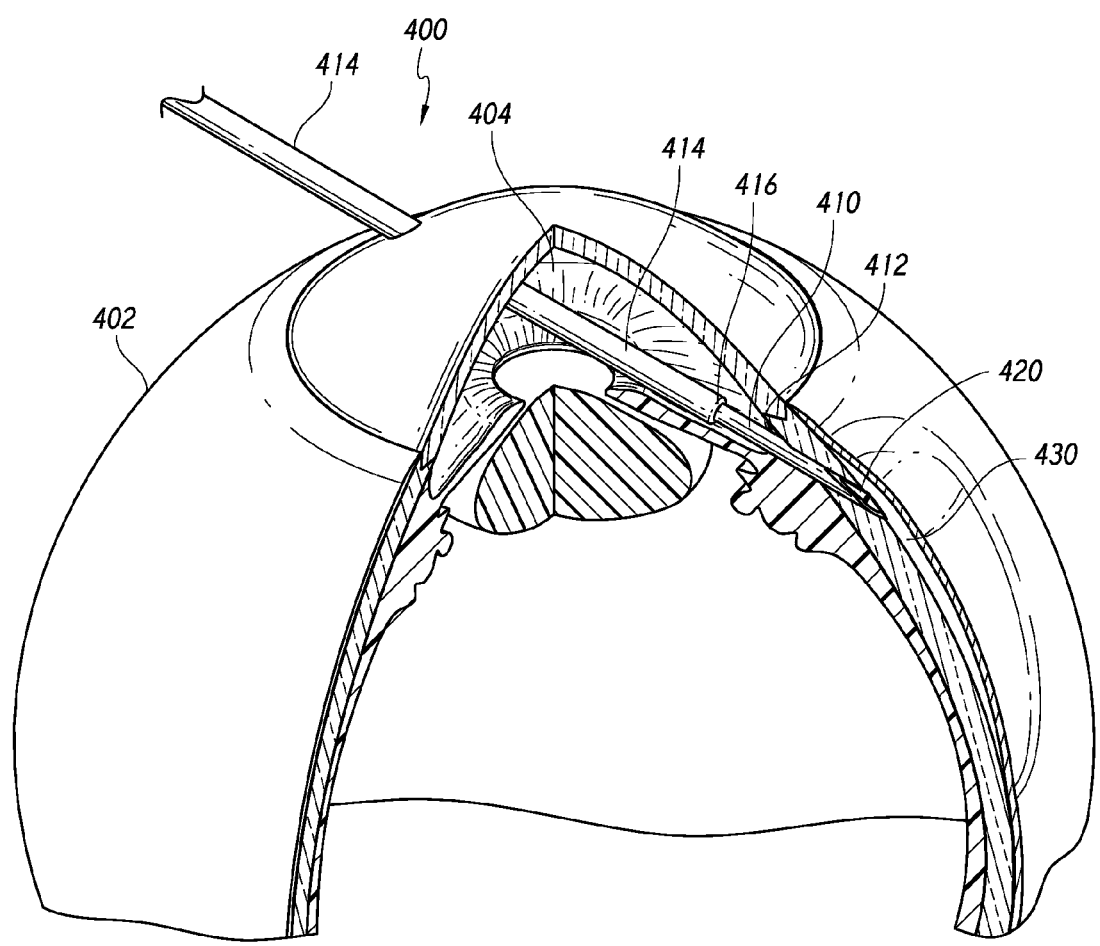
Figure 52C:
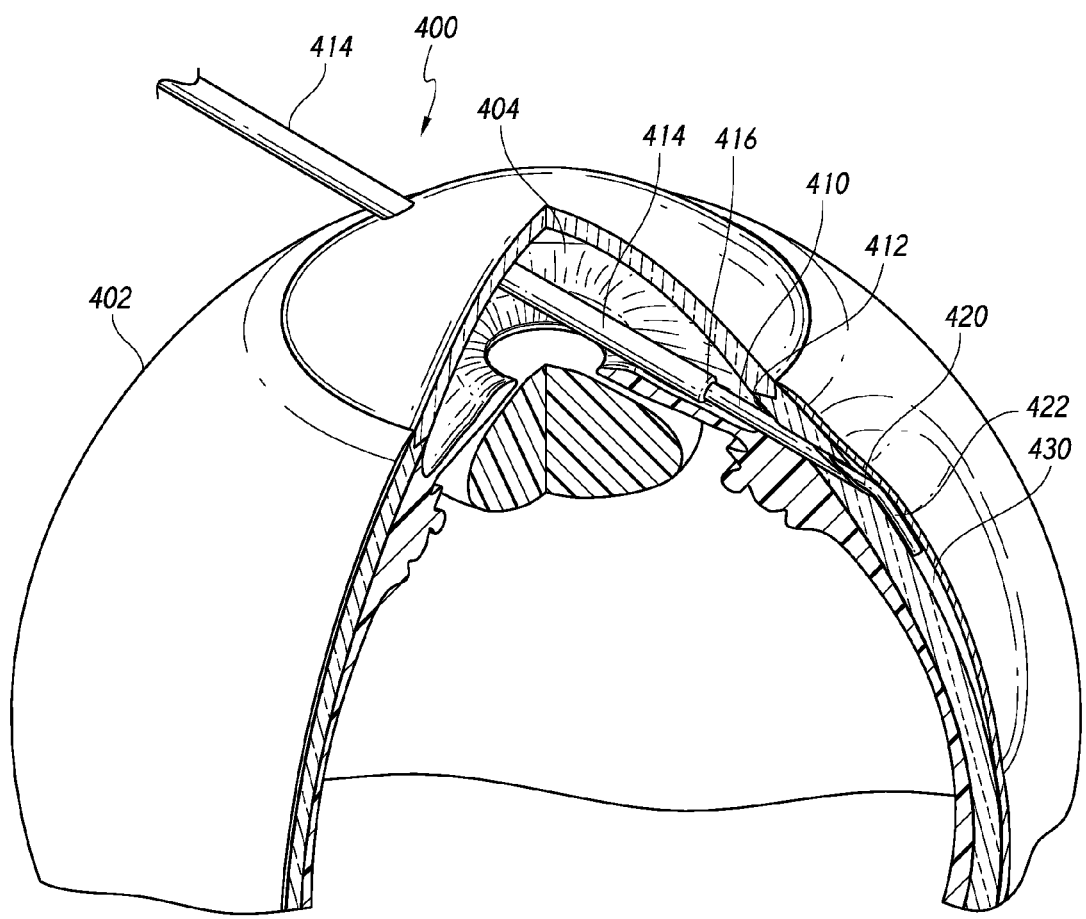
Figure 52D:
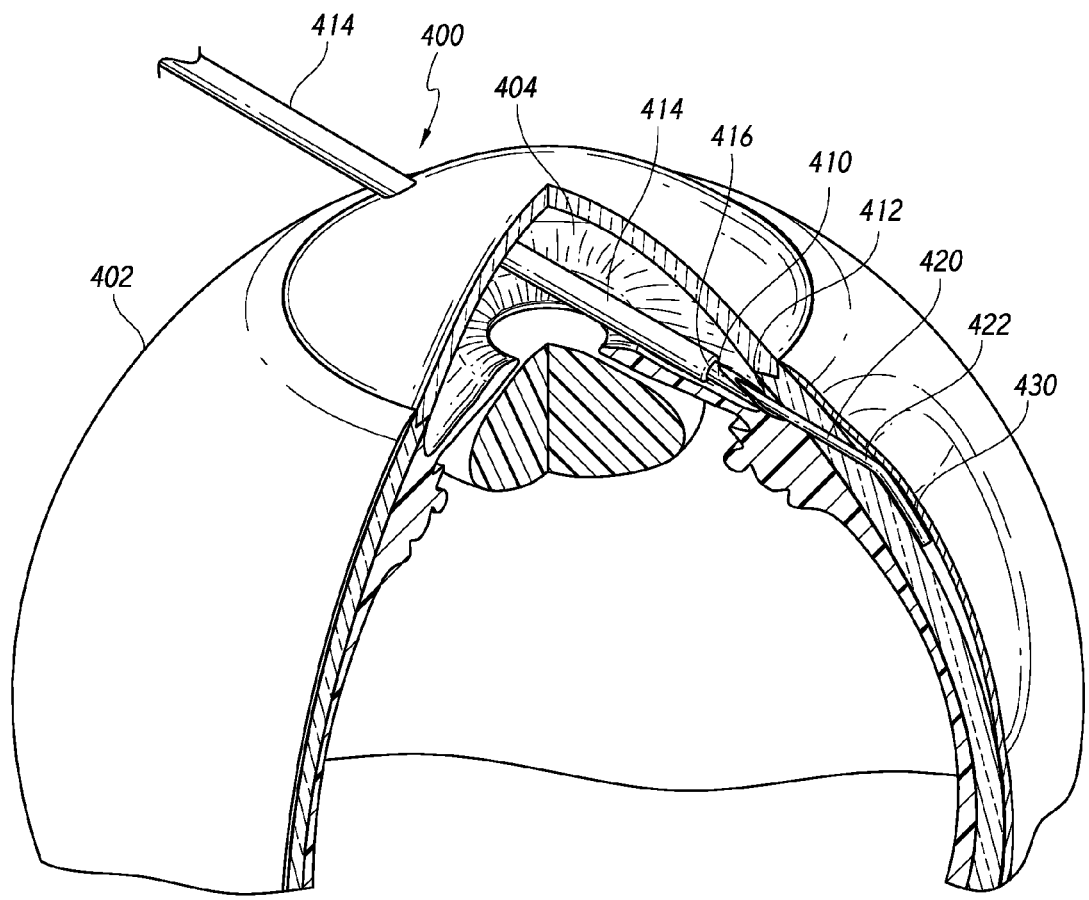

The advancement of the distal end portion 422 of the shunt 420 into the desired location of the eye 402 can be performed by advancing the pusher component (not shown) relative to the shaft 410 while maintaining the shaft 410 and the sleeve 414 steady, at a generally constant position or location, until the distal end portion 422 has been fully advanced into the desired location, as illustrated in FIGS. 52B-52C. Thereafter, as shown in FIG. 52D, the shaft 410 can be proximally withdrawn relative to the shunt 420. In some embodiments, the shaft 410 can also be proximally withdrawn relative to the sleeve 414 and the pusher component while maintaining the sleeve 414 steady, at a generally constant position or location relative to the tissue. As the shaft 410 is proximally withdrawn from the tissue of the eye 402, the pusher component maintains the longitudinal position of the shunt 420 in order to ensure that the distal end portion 422 remains embedded at the desired location. Accordingly, proximal withdrawal of the shaft 410, while maintaining the position of the shunt 420 in the eye 402, allows further exposure of the shunt 422 surrounding tissue.

Figure 52E:
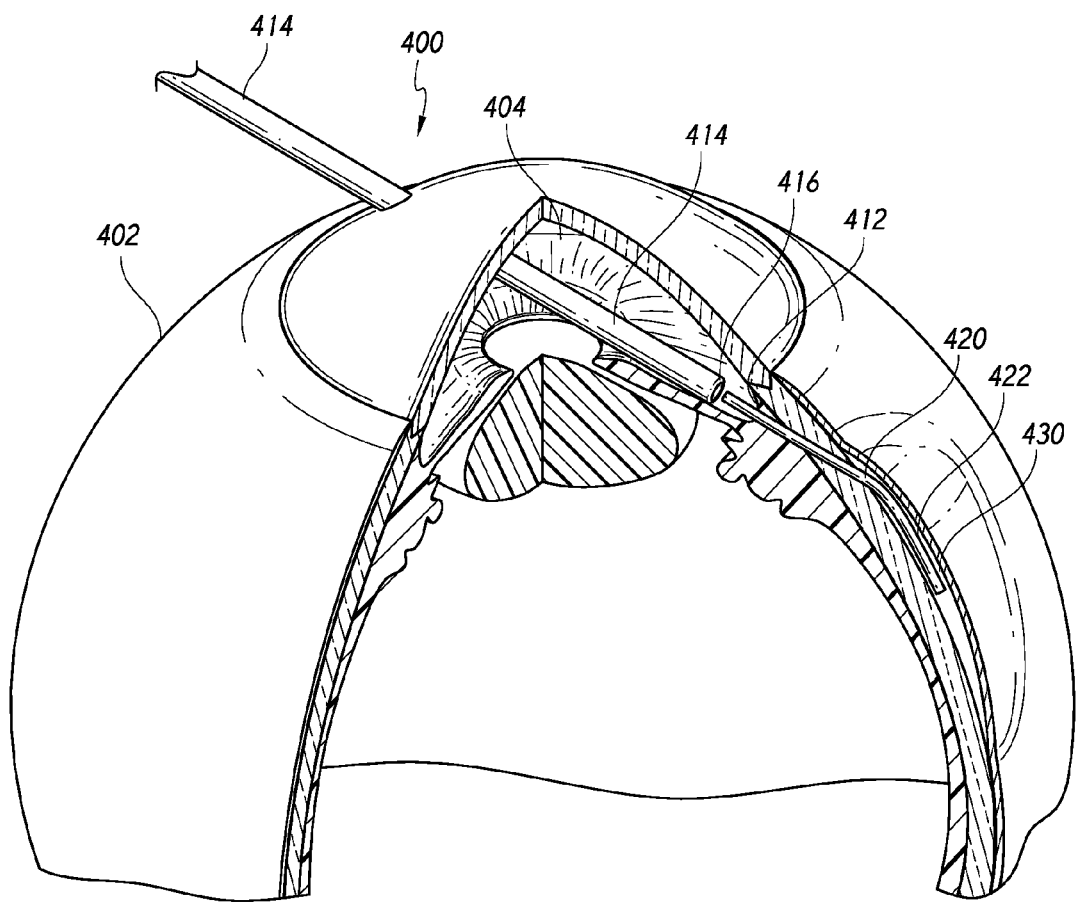

Eventually, after the shunt 420 is released or embedded within the eye tissue, the shaft 410 can be fully withdrawn from covering or enclosing the shunt 420, as shown in FIG. 52E. Further, in some embodiments, the shaft 410 can be completely retracted into the lumen of the sleeve 414, as also illustrated in FIG. 52E. The shaft 410 and the pusher component can be further withdrawn or retracted together into the lumen of the sleeve 414, as necessary. Thereafter, the device 400 can be proximally withdrawn from the eye 402 and the procedure can be completed.

In accordance with some embodiments, the device 400 can also deliver the shunt 420 by allowing the distal end 416 of the sleeve 414 to contact or abut tissue within the eye. For example, the distal end 416 of the sleeve 414 can comprise one or more blunt structures, such as an edge, protrusion, and/or an annular, enlarged portion, that can be abutted with tissue of the eye 402, such as the anterior chamber angle tissue.

For example, referring to FIGS. 53A-53E, after the device 400 is advanced into the anterior chamber 404, as discussed above with respect to FIG. 52A, the needle or shaft 410 can pierce the anterior chamber angle tissue. According to some embodiments, the device 400 can be advanced until the distal end 416 of the shaft 414 abuts the anterior chamber angle tissue of the anterior chamber angle 412. This abutment can provide resistance feedback to an operator, indicating that no further advancement of the device 400 is necessary. As discussed herein, the device 400 can comprise a blunt structure to prevent the shaft 410 from accidentally being pushed too far through the eye tissue.

In some embodiments, such as that illustrated in FIGS. 53A-53E, as the device 400 is moved through the anterior chamber 404 and into initial position within the eye tissue, the shaft 410 can be positioned relative to the sleeve 414 such that the bevel 418 is spaced about 2 mm to about 6 mm, about 3 mm to about 5 mm, or about 4 mm from the distal end 416 of the sleeve 414. Such spacing can tend to ensure that the distal end 416 of the sleeve 414 is able to contact the anterior chamber angle tissue as the bevel 418 emerges from the sclera, but avoid piercing of the sclera.

Figure 53A:
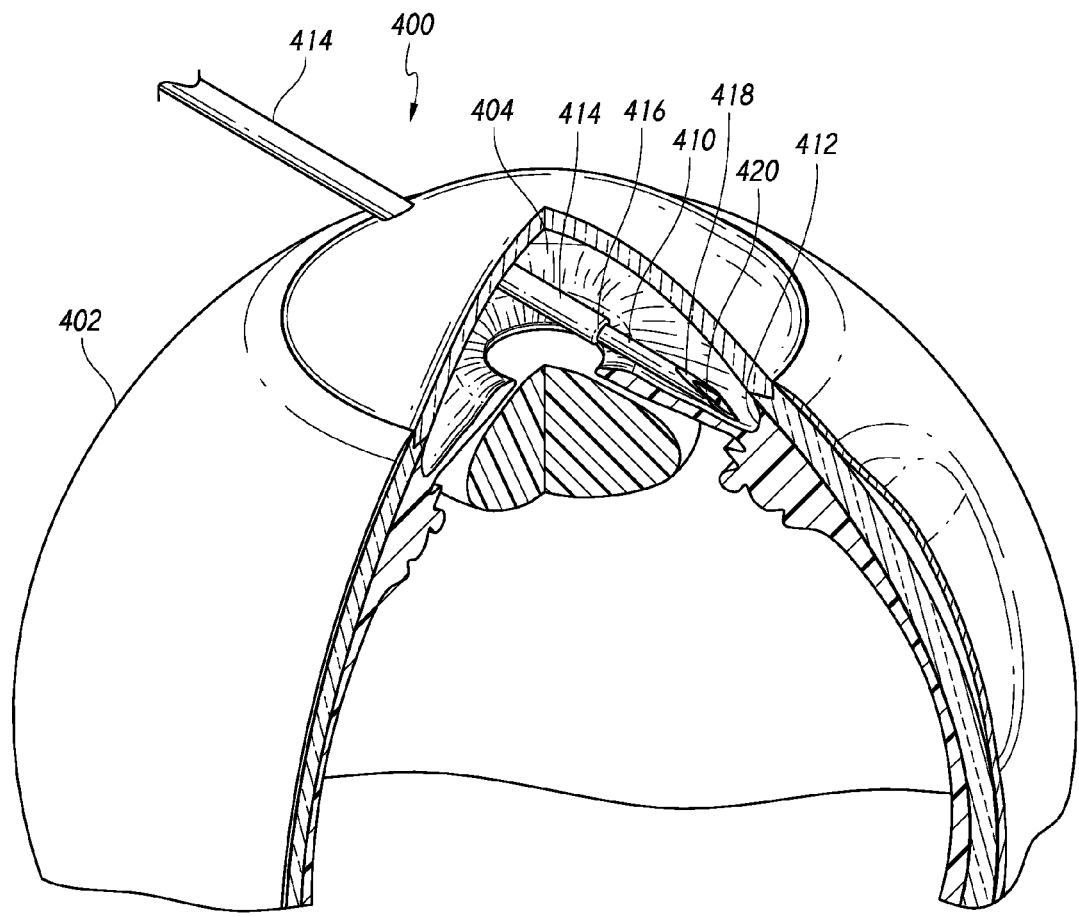
FIGS. 53A-53E depict an intraocular shunt being deployed within the eye, according to yet another embodiment.
Figure 53B:
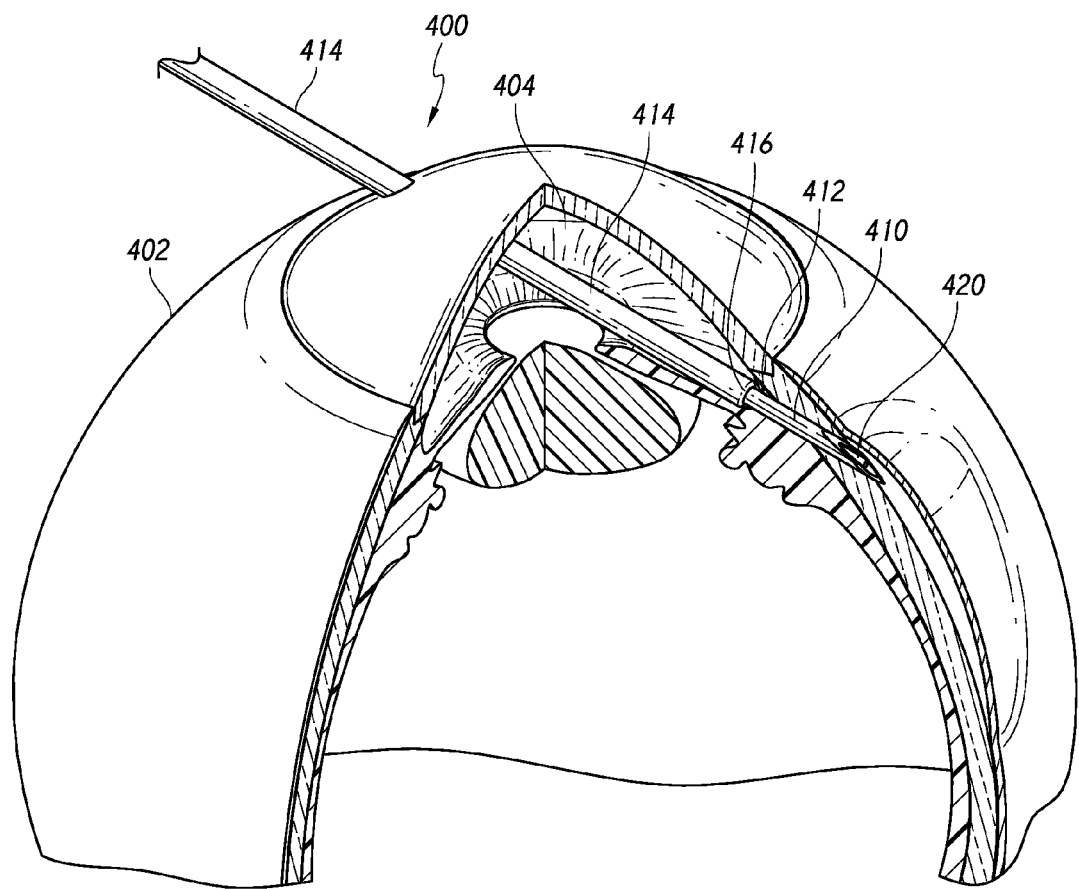
Figure 53C:
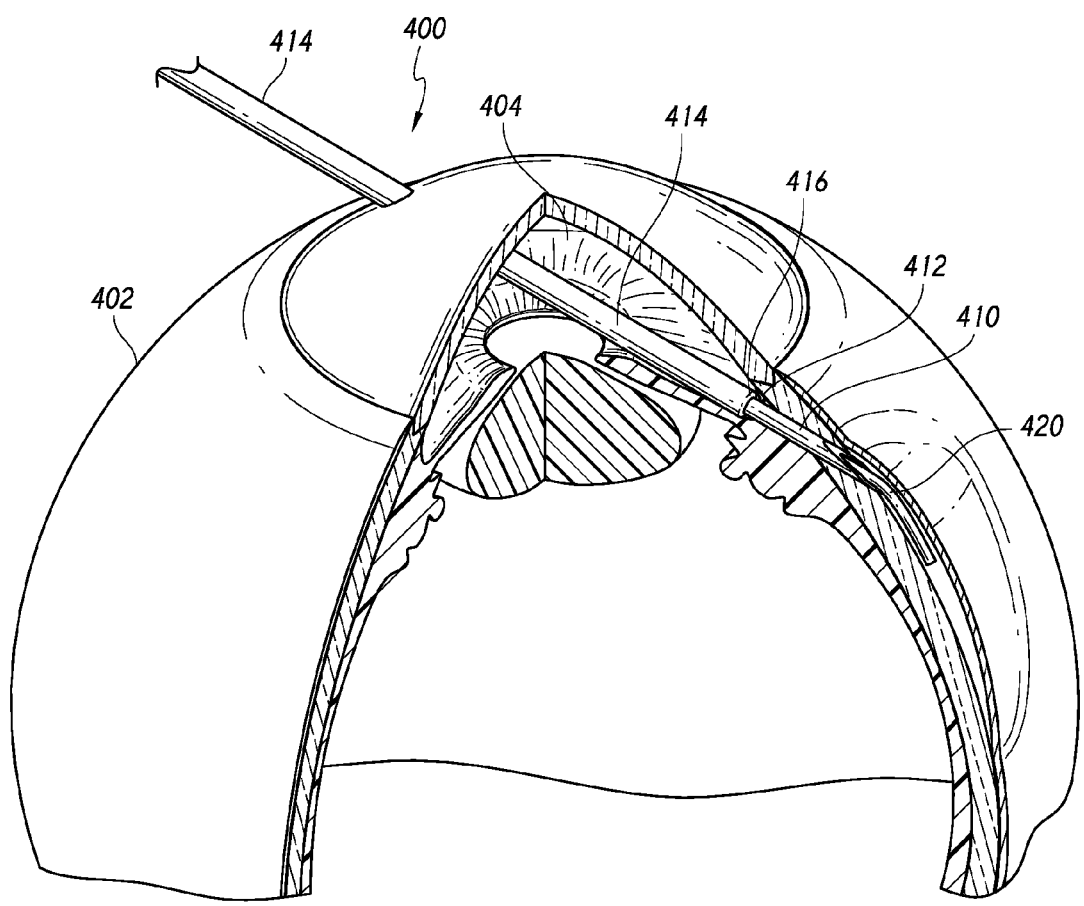

Once the distal end 416 of the sleeve 414 is positioned abutting the tissue of the eye 402, the shunt 420 can be advanced distally, e.g., by using a pusher component (not shown), until a distal end portion 430 of the shunt 420 is positioned at the desired location, as shown in FIG. 53C. In some embodiments, such as that shown in FIGS. 53A-53E, the position of the distal end 416 of the sleeve 414 relative to the fully extended pusher component can be configured such that a maximum distal displacement or maximum distal position of the pusher component is longitudinally proximal to the sleeve distal end 416 when the pusher component is advanced within the shaft (see also FIGS. 23-30). For example, the pusher component can have a distalmost position of between about 0 mm and about 8 mm, about 0 mm and about 4 mm, about 0 mm and about 2 mm, or about 0 mm and about 1 mm proximal to the sleeve distal end.

Figure 53D:
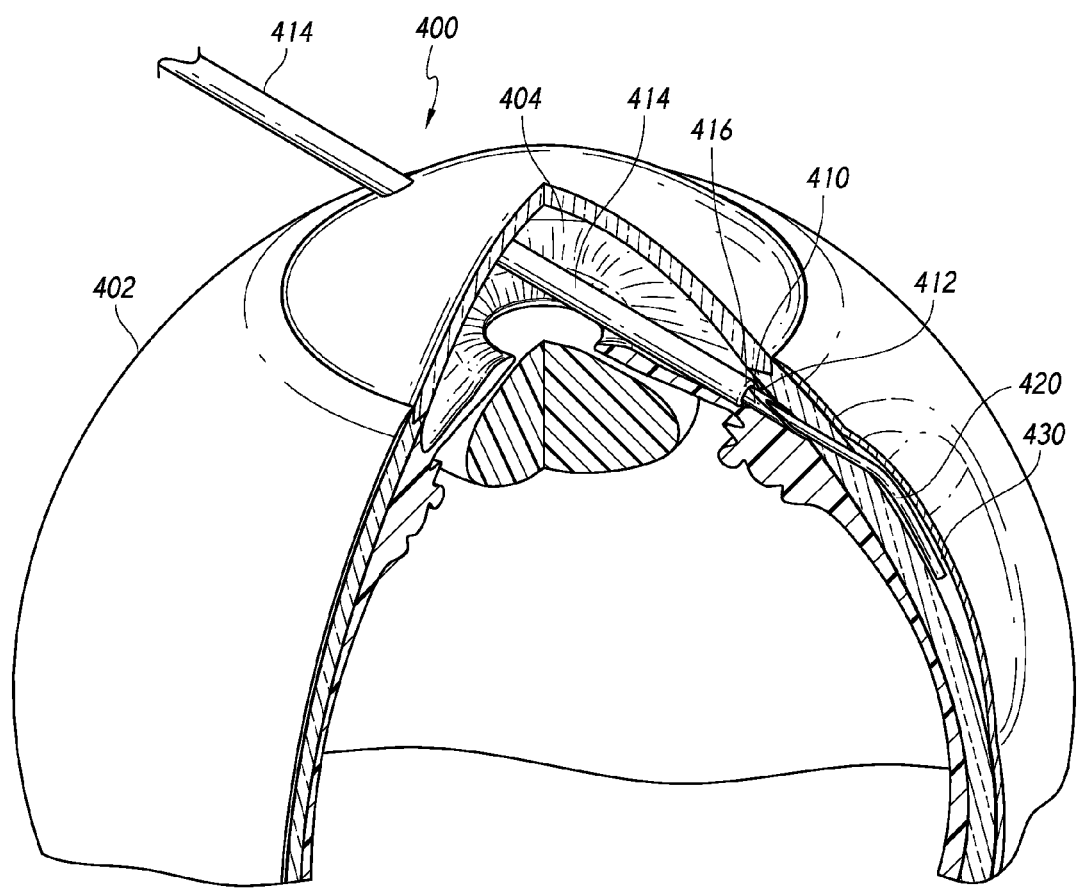
Figure 53E:
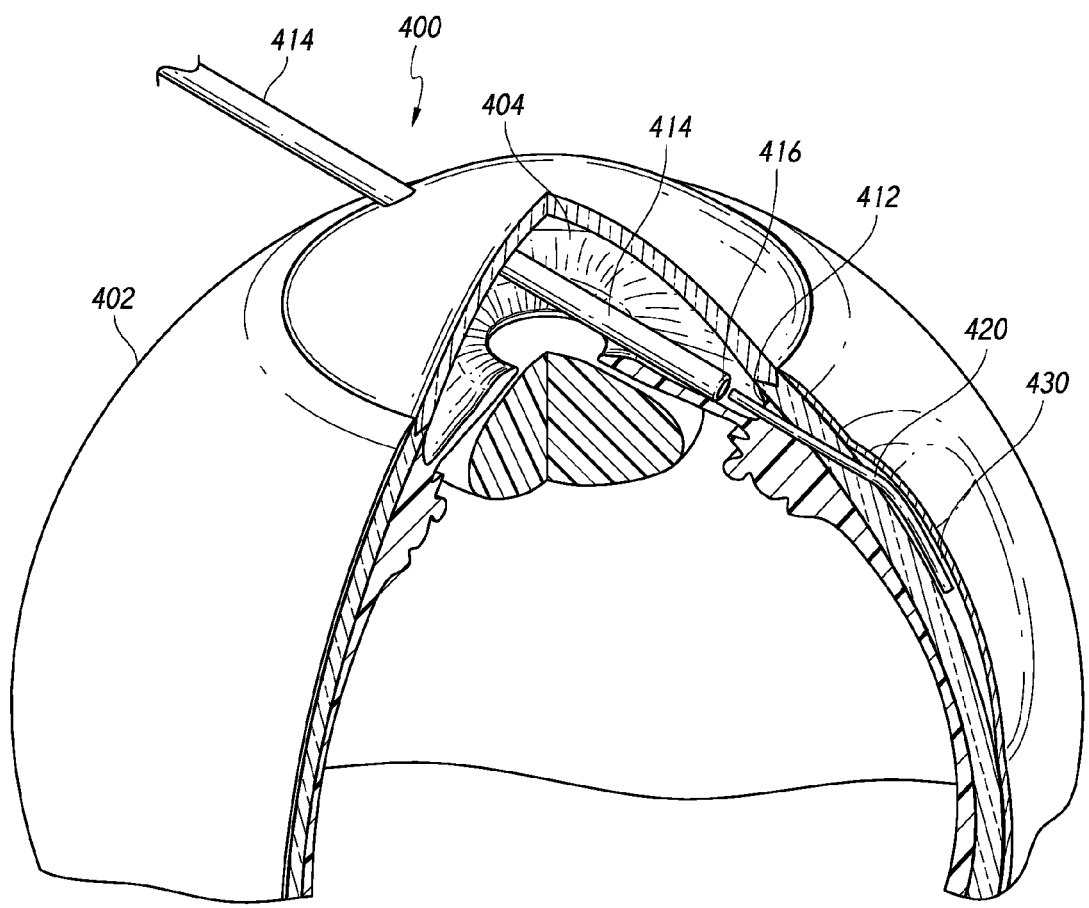

Thereafter, once the shunt 420 is advanced to its final position, as shown in FIG. 53D, the shaft 410 can be proximally withdrawn relative to the sleeve 414 to further expose the shunt 420 to surrounding tissue. Additionally, as shown in FIG. 53E, and as discussed above, the shaft 410 can be fully withdrawn into the sleeve 414. Finally, the device 400 can be removed from the eye and the procedure can be completed.

Further, in the embodiment illustrated in FIGS. 54A-54E, the device 400 can be advanced through the anterior chamber 404 and the shaft 410 can pierce and enter eye tissue. The device 400 can be advanced until a distal end 416 of the sleeve 414 is positioned adjacent to or spaced apart from, but not abutting, the anterior chamber angle tissue or is positioned within the anterior chamber angle 412 (a similar initial position to that of FIG. 52B). Such a position can be a preliminary stop position, as mentioned above, at which the clinician can cease advancement of the device 400.

In such embodiments, after the device 400 has been initially placed in the anterior chamber angle tissue or anterior chamber angle 412, the shunt 420 can be released by a motion sequence in which the shaft 410 is maintained steady within the tissue while the distal end 416 of the sleeve 414 is advanced to abut the anterior chamber angle tissue, as discussed below. Such a motion can, in some embodiments, require that the operator or clinician further advance the device 400 axially until reaching a final stop position, achieved when the distal end 416 of the sleeve 414 abuts the anterior chamber angle tissue. However, the device 400 can also be configured to allow the sleeve 414 to move relative to a housing of the device, thereby allowing the operator or clinician to maintain the device 400 stationary relative to the face of the patient as the sleeve 414 is advanced further toward the anterior chamber angle tissue.

Figure 54A:
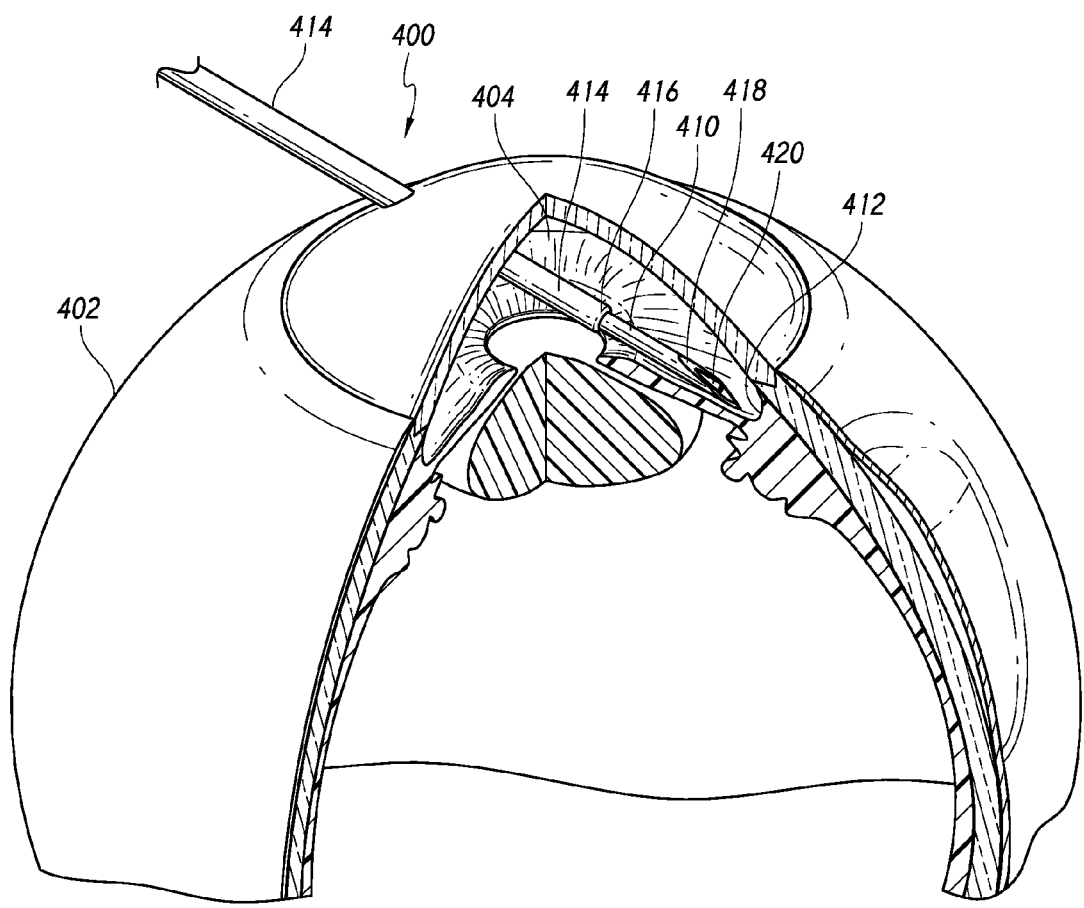
FIGS. 54A-54E depict an intraocular shunt being deployed within the eye, according to yet another embodiment.
Figure 54B:
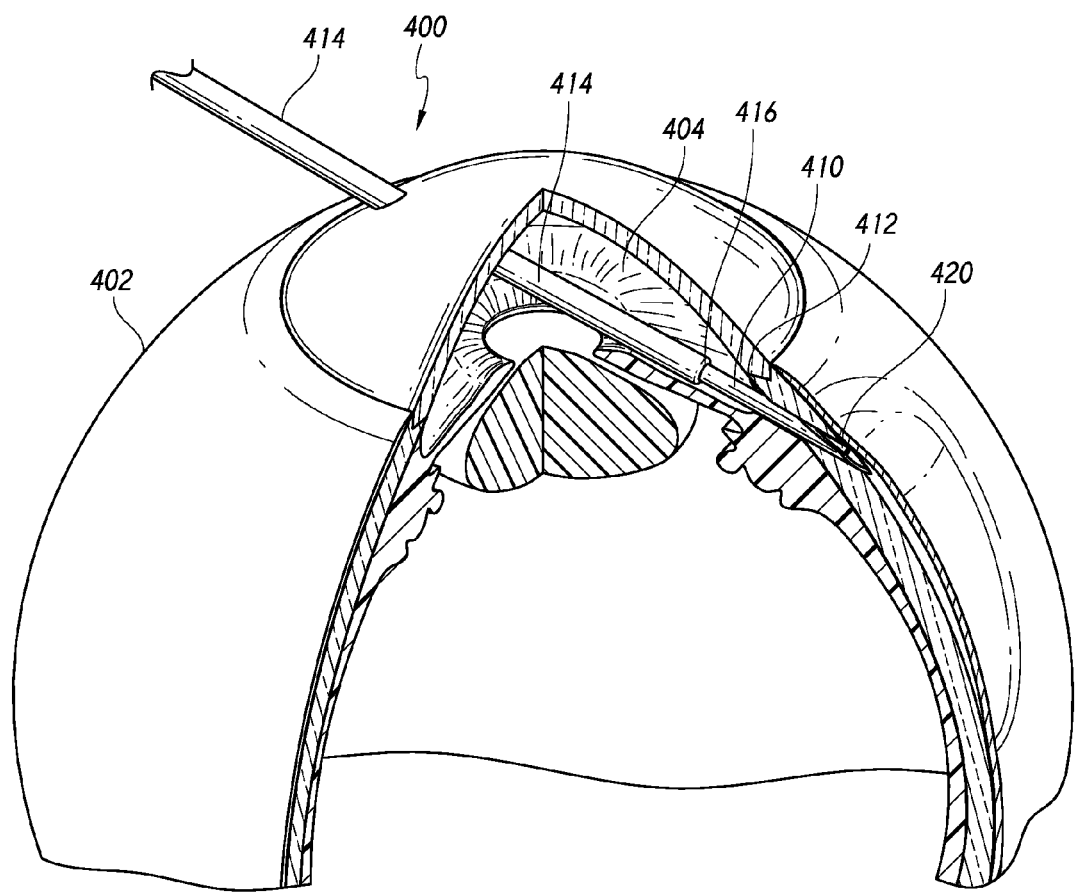

As illustrated in FIGS. 54A-54B, the device 400 initially enters the anterior chamber 404 and is advanced until the shaft 410 pierces the anterior chamber angle tissue. The distal end 416 of the sleeve 414 can be maintained or held spaced apart from the eye tissue or anterior chamber angle 412, at an initial placement or position such as that discussed above with respect to FIG. 52B. Although a clinician can, in some embodiments, verify initial placement of the device 400 with reference only to the position of the distal end 416 of the sleeve 414 relative to the anterior chamber angle tissue or anterior chamber angle 412, the initial placement or position of the device 400 can also be based on the position of the shaft 410 within the eye tissue.

For example, as similarly discussed above, for subconjunctival placement of the shunt 420, the shaft 410 (and hence, the sleeve 414) will be at its proper location when a bevel 418 of the shaft 410 has exited or emerged from the sclera, but has not penetrated the conjunctiva. This emergence can be visually verified because the bevel 418 can be seen through or below the conjunctiva (which is translucent). Thereafter, the position of the device 400 within the eye 402 can be maintained steady such that the bevel 418 remains positioned adjacent to or opening to the subconjunctival space.

In such embodiments, such as that illustrated in FIGS. 54A-54E, as the device 400 is moved through the anterior chamber 404 and into initial position within the eye tissue, the shaft 410 can be positioned relative to the sleeve 414 such that the bevel 418 is spaced about 1 mm to about 5 mm, about 2 mm to about 4 mm, or about 3 mm from the distal end 416 of the sleeve 414. Such spacing can allow the distal end 416 of the sleeve 414 to be spaced apart from the eye tissue or anterior chamber angle 412 when the bevel 418 emerges from the sclera. Thus, the clinician can advantageously confirm proper initial placement of the device 400 by verifying bevel emergence from the sclera if it would otherwise be difficult to visually verify a relative positioning of the distal end 416 of the sleeve 414 and the tissue or anterior chamber angle 412. This provides freedom to allow for variability in the anatomy and/or trajectory of the advancing shaft 410.

Once initial placement of the device 400 is proper, the motion sequence can continue by initiating relative movement between the shaft 410, the sleeve 414, and pusher component (not shown) to begin releasing the shunt 420.

Figure 54C:
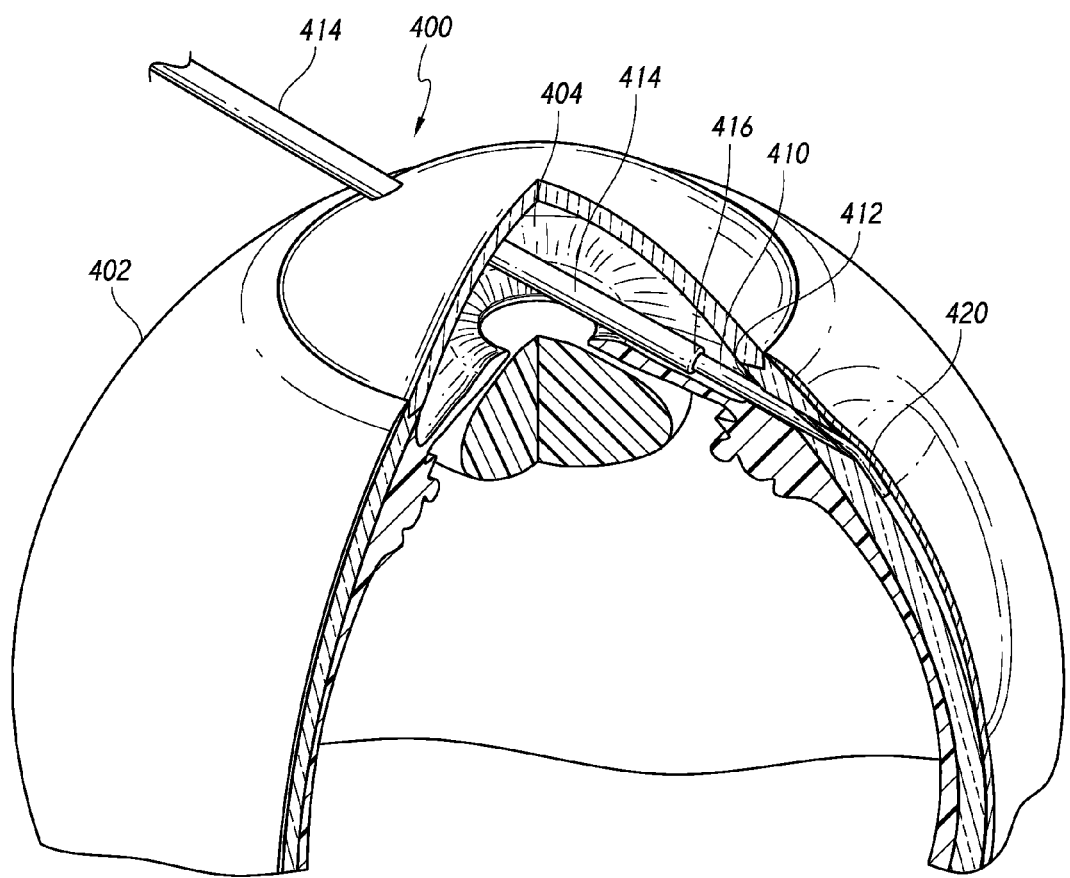
Figure 54D:
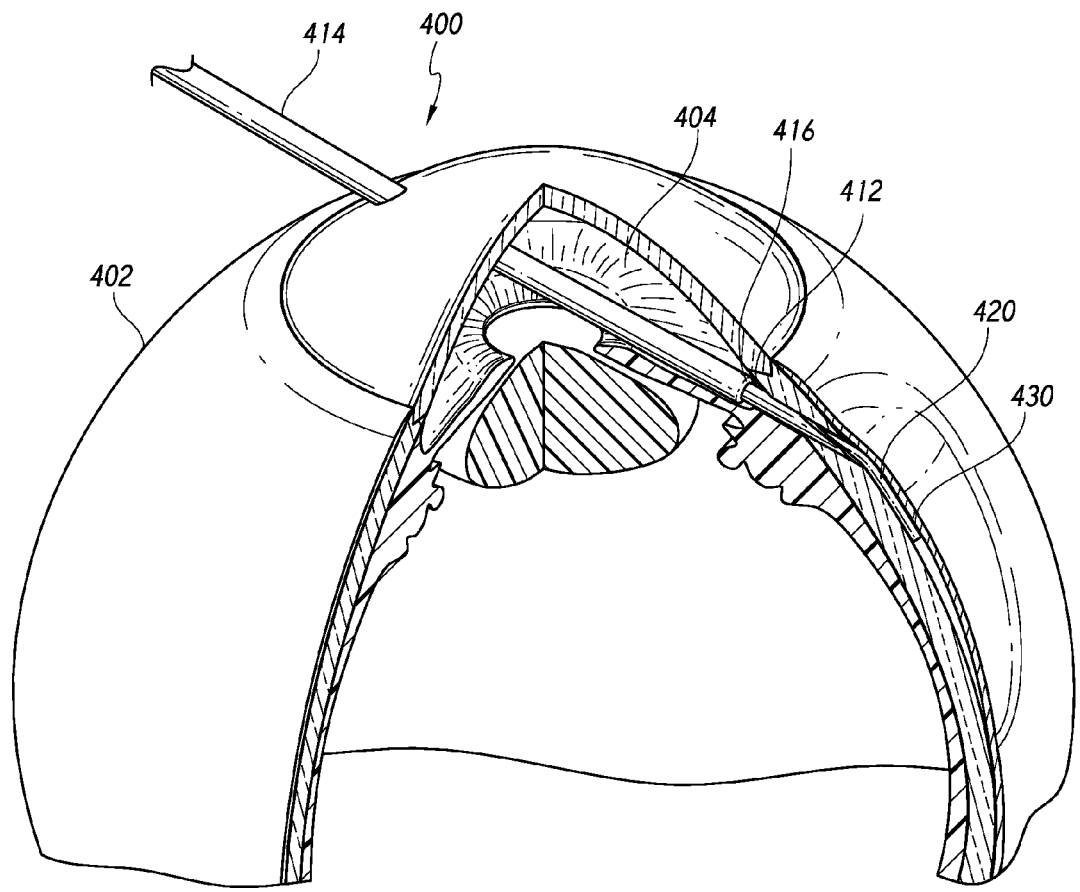

As illustrated in FIGS. 54C-54D, after the device 400 reaches the initial position, the shunt 420 can be distally advanced into the tissue until a distal end portion 430 reaches the desired location. The advancement of the distal end portion 422 of the shunt 420 into the desired location of the eye 402 can be performed by advancing the pusher component (not shown) relative to the shaft 410 while maintaining the shaft 410 and the sleeve 414 steady, at a generally constant position or location Further, as illustrated in FIG. 54D, the shaft 410 can be proximally withdrawn into the sleeve 414. However, instead of maintaining the sleeve 414 at a generally constant position or location relative to the eye while the shaft 410 is withdrawn into the sleeve 414 (and in contrast to the embodiments discussed in FIGS. 52A-53E), the shaft 410 can be obtained at a generally constant position relative to the eye tissue while the sleeve 414 moves relative to the eye tissue.

For example, the relative movement between the sleeve 414 and the shaft 410 while the shaft 410 remains at a constant position relative to the eye tissue causes the sleeve 414 to be longitudinally advanced along the shaft 410, distally toward the eye tissue or anterior chamber angle 412. Thus, the sleeve 414 can move while the shaft 410 is held steady in the eye, at a generally constant position or location within the tissue. Accordingly, the sleeve 414 will be distally advanced toward the anterior chamber angle 412 until the distal end 416 of the sleeve 414 contacts or abuts the eye tissue, such as the anterior chamber angle tissue.

In some embodiments, the sleeve 414 can be advanced distally along the shaft 410 by about 1 mm, about 2 mm, about 3 mm, about 4 mm, about 5 mm, about 6 mm, or more, as necessary, until contacting eye tissue.

For example, the sleeve distal end 416 can be distally advanced between about 1 mm to about 4 mm or between about 2 mm to about 3 mm. The sleeve can be advanced at a rate of between about 0.15 mm/sec to about 0.85 mm/sec, and in some embodiments, between about 0.25 mm/sec to about 0.65 mm/sec.

Figure 54E:
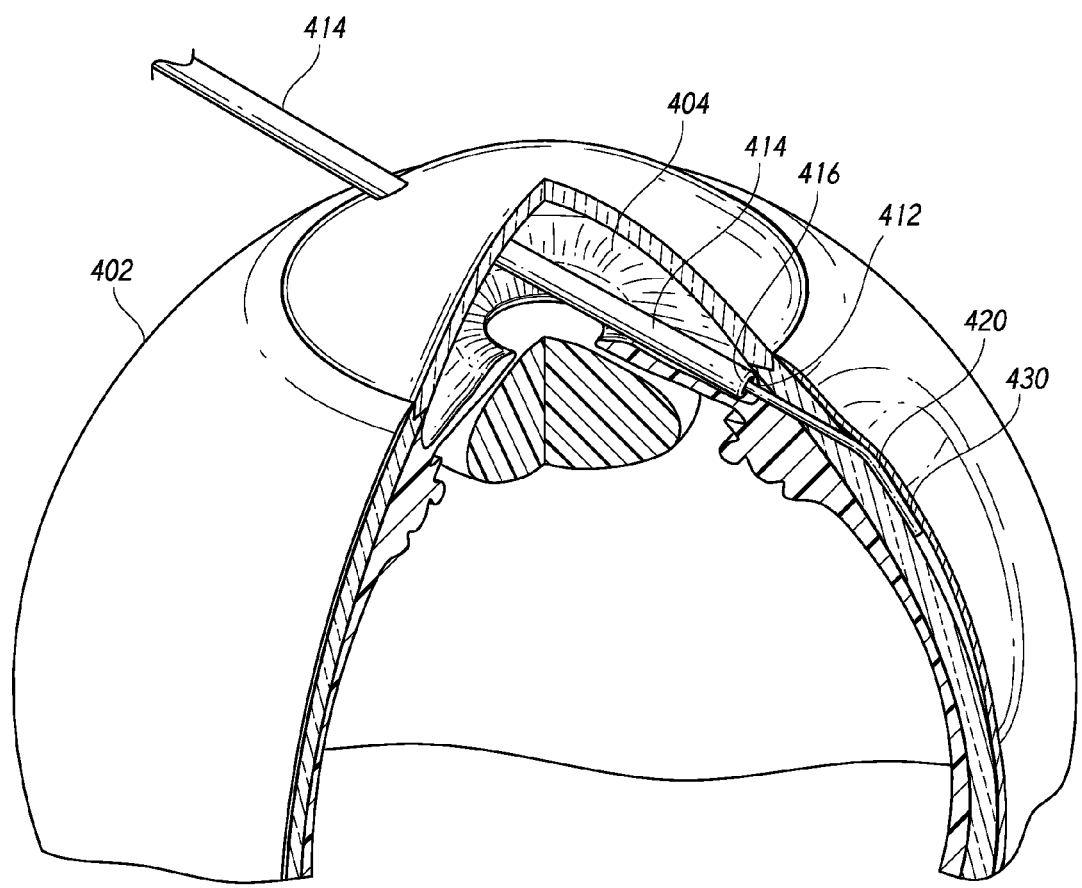

When the distal end 416 abuts the eye tissue, further relative retraction of the shaft 410 into the sleeve 414 will cause the shaft 410 to be proximally withdrawn from the tissue because the distal end 416 of the sleeve 414 has now abutted the anterior chamber angle tissue, as illustrated in FIGS. 54D-54E. Continued retraction or withdrawal of the shaft 410 can cause the shaft 410 to be fully withdrawn into the lumen of the sleeve 414.

Aspects of the procedures discussed herein, including those discussed with respect to FIGS. 52A-54E, can be implemented in various embodiments of a procedure for implanting an intraocular shunt. The deployment device can operate according to the features of any of the embodiments disclosed herein.

In any of the procedures discussed above with respect FIGS. 52A-54E, when the bevel 418 has been advanced through the sclera toward the subconjunctival space, it may be necessary to further actuate the bevel 418 in order to ensure that the subconjunctival space has been reached and can be easily accessed by the shunt.

First, some clinicians may tend to conservatively advance the bevel 418 within the sclera and fail to reach the subconjunctival space such that the bevel 418 is placed between the sclera and the conjunctiva. In such situations, when the bevel 418 has been advanced to a position shy of the subconjunctival space within the sclera, the bevel 418 can be rotated within the sclera to permit the bevel 418 to "crack" the sclera and ensure that the subconjunctival space has been accessed. The rotation of the bevel 418 can cause the oblong or oval shape of the bevel 418 to rotate from a flat position to an upright position, thereby pushing, breaking, or otherwise breaching the top surface of the sclera so that the lumen of the shaft 410 opens to the subconjunctival space to allow the shunt 420 to be advanced therefrom.

Second, in order to ensure that the subconjunctival space can be easily accessed by the shunt, even when the sclera has been breached in the subconjunctival space has been accessed, rotating the bevel 418 can cause the conjunctiva to become "tented" or spaced apart from the top surface of the sclera. This "tenting" of the conjunctiva can create a pocket within the subconjunctival space. When advancing the shunt 420, the pocket will provide little frictional resistance or threat of impeding travel of the shunt 420 within the subconjunctival space. Accordingly, the shunt 420 can more readily begin its entry into the subconjunctival space, thus avoiding kinking or bending of the shunt 420 due to high frictional resistance that would otherwise be present absent the creation of the pocket within the subconjunctival space.

Further teachings regarding the rotation or actuation of the bevel 418 within the sclera are disclosed in Applicant's copending U.S. patent application Ser. No. 12/946,556, filed Nov. 15, 2010, the entirety of which is incorporated herein by reference.

Further, the relative positioning of a shunt within the shaft and the range of movement of the pusher component within the shaft can be selectively modified to optimize the position of the shunt end portions when performing the motion sequences of the deployment device. In particular, to ensure proper placement of the distal end portion of the shunt, the maximum distal or fully advanced position of the pusher component relative to the sleeve distal end can be optimized.

For example, as noted above, the pusher component can have a maximum distal displacement or maximum distal position that results in the pusher component being positioned at least longitudinally adjacent to (longitudinally coextensive with) the sleeve distal end or distally beyond the sleeve distal end when the distal end of the sleeve distal end is maintained spaced apart from the eye tissue (e.g., spaced apart from the anterior chamber angle tissue), when the pusher component is advanced within the shaft (see FIGS. 33-41, FIGS. 52B-52C, and FIGS. 54B-54C). For example, the pusher component can have a distalmost position of between 0 mm and about 8 mm, about 0 mm and about 4 mm, about 0 mm and about 2 mm, or about 0 mm and about 1 mm beyond or distal to the sleeve distal end.

Further, as noted above, the pusher component can have a maximum distal displacement or maximum distal position that results in the pusher component being positioned longitudinally proximal to the sleeve distal end when the pusher component is advanced within the shaft (see FIGS. 23-30 and FIGS. 53B-53C). For example, the pusher component can have a distalmost position of between about 0 mm and about 8 mm, about 0 mm and about 4 mm, about 0 mm and about 2 mm, or about 0 mm and about 1 mm proximal to the sleeve distal end.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the inventions have been described, these have been presented by way of example only, and are not intended to limit the scope of the inventions. Indeed, the novel methods and systems described herein may be embodied in a variety of other forms without departing from the spirit thereof. The accompanying claims and their equivalents are intended to cover such forms or modifications as would fall within the scope and spirit of the inventions.

What is claimed is:

1. A method of treating glaucoma comprising:
    inserting a shaft of an inserter device into eye tissue, the device supporting an intraocular shunt and comprising a sleeve that extends about at least a portion of the shaft;
    advancing the shaft until reaching a first position at which (i) a bevel of the shaft is in a space adjacent to Tenon's capsule and (ii) a distal end of the sleeve is spaced apart from the eye tissue;
    releasing the shunt from the shaft such that an inflow end of the shunt is positioned in an anterior chamber of the eye and an outflow end of the shunt is positioned in a space in contact with Tenon's capsule;
advancing the sleeve distally over the shaft until the sleeve distal end contacts the eye tissue; and
withdrawing the shaft and sleeve from the eye.

2. The method of claim 1, wherein the inserting further comprises introducing the shunt into the eye through a cornea of the eye.

3. The method of claim 1, wherein the inserting comprises advancing the shaft into sclera until reaching and no further than the first position.

4. The method of claim 3, wherein after reaching the first position, the releasing comprises advancing a pusher component of the device such that the shunt is pushed distally out of the shaft.

5. The method of claim 4, wherein the advancing the pusher component comprises pushing less than an entire length of the shunt distally out of the shaft.

6. The method of claim 4, wherein the inserting further comprises advancing the pusher component to a distalmost position at which a distal end of the pusher component is positioned longitudinally proximal to the sleeve distal end.

7. The method of claim 4, wherein the sleeve comprises a lumen, the shaft being disposed within the lumen.

8. The method of claim 7, wherein the inserting further comprises advancing the pusher component until a distal end of the pusher component is positioned longitudinally adjacent to the sleeve distal end.

9. The method of claim 1, wherein the sleeve distal end is spaced apart from anterior chamber angle tissue in the first position.

10. The method of claim 1, wherein the advancing the sleeve occurs while maintaining the shaft fixed relative to the eye tissue.

11. The method of claim 10, wherein after the sleeve distal end contacts the eye tissue, the releasing further comprises proximally withdrawing the shaft from the eye tissue until the bevel is received within the sleeve.

12. The method of claim 1, wherein at the first position, the bevel of the shaft is positioned between layers of Tenon's capsule to position the shunt outflow end between the layers of Tenon's capsule.

13. The method of claim 1, wherein the releasing comprises positioning the shunt outflow end deep to Tenon's capsule.

14. The method of claim 1, wherein the releasing comprises positioning the shunt outflow end in a subconjunctival space.

15. The method of claim 1, wherein the device further comprises a plunger disposed within a lumen of the shaft to abut the shunt, and wherein the releasing further comprises, while maintaining the bevel stationary relative to the eye tissue, advancing the sleeve and the plunger relative to the shaft until the sleeve distal end contacts the eye tissue.

16. A method of treating glaucoma comprising:
advancing a shaft of a device into eye tissue until a bevel of the shaft reaches a target area and a sleeve of the device is spaced apart from the eye tissue, the shaft supporting an intraocular shunt;
advancing the shunt from the shaft into the target area;
while maintaining the bevel stationary relative to the target area, advancing the sleeve distally over the shaft until a distal end of the sleeve contacts the eye tissue; and
upon contacting the sleeve distal end with the eye tissue, proximally withdrawing the shaft from the eye tissue.

17. The method of claim 16, further comprising, while maintaining the bevel stationary relative to the target area, advancing a plunger within the shaft to advance the shunt from the bevel until the shunt extends into the target area.

18. The method of claim 17, wherein the advancing the plunger further comprises pushing less than an entire length of the shunt distally out of the shaft.

19. The method of claim 17, wherein the advancing the plunger further comprises advancing the plunger until a distal end of the plunger is positioned longitudinally adjacent to the sleeve distal end.

20. The method of claim 16, wherein the advancing the shaft comprises introducing the shaft through a cornea of the eye.

21. The method of claim 16, wherein the target area comprises supraciliary space, suprachoroidal space, a space between layers of sclera, a space between layers of Tenon's capsule, or subconjunctival space.

22. The method of claim 16, wherein the advancing the sleeve comprises advancing the sleeve between about 1 mm to about 4 mm.

23. The method of claim 22, wherein the advancing the sleeve comprises advancing the sleeve between about 2 mm to about 3 mm.

24. The method of claim 16, wherein the device further comprises a plunger disposed within a lumen of the shaft to abut the shunt, and wherein the advancing comprises advancing the sleeve and the plunger relative to the shaft until the sleeve distal end contacts the eye tissue.

* * * * *